US009550829B2

(12) United States Patent
French et al.

(10) Patent No.: US 9,550,829 B2
(45) Date of Patent: Jan. 24, 2017

(54) COMPOSITIONS AND METHODS FOR DIAGNOSIS AND TREATMENT OF HEPATIC CANCERS

(71) Applicant: Genentech, Inc., South San Francisco, CA (US)

(72) Inventors: Dorothy French, San Carlos, CA (US); Erik Huntzicker, South San Francisco, CA (US); Christian W. Siebel, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/208,523

(22) Filed: Mar. 13, 2014

(65) Prior Publication Data

US 2014/0314749 A1 Oct. 23, 2014

Related U.S. Application Data

(60) Provisional application No. 61/789,475, filed on Mar. 15, 2013.

(51) Int. Cl.

| | |
|---|---|
| ***A61K 39/395*** | (2006.01) |
| ***C07K 16/18*** | (2006.01) |
| ***C07K 16/22*** | (2006.01) |
| ***C07K 16/30*** | (2006.01) |
| ***C07K 16/28*** | (2006.01) |
| ***A61K 47/48*** | (2006.01) |
| *C07K 14/475* | (2006.01) |
| *C07K 14/52* | (2006.01) |
| *A61K 39/00* | (2006.01) |

(52) U.S. Cl.

CPC ........... *C07K 16/28* (2013.01); *A61K 39/3955* (2013.01); *A61K 47/48561* (2013.01); *C07K 16/2896* (2013.01); *A61K 39/39558* (2013.01); *A61K 2039/505* (2013.01); *C07K 16/18* (2013.01); *C07K 16/22* (2013.01); *C07K 16/30* (2013.01); *C07K 2316/96* (2013.01); *C07K 2317/33* (2013.01); *C07K 2317/55* (2013.01); *C07K 2317/565* (2013.01); *C07K 2317/567* (2013.01); *C07K 2317/73* (2013.01); *C07K 2317/75* (2013.01); *C07K 2317/76* (2013.01)

(58) Field of Classification Search

CPC ..................... A61K 39/3955; A61K 39/39558; A61K 2039/505; C07K 16/18; C07K 16/22; C07K 16/30; C07K 16/00; C07K 2317/76; C07K 2317/56; C07K 2317/565; C07K 2317/73; C07K 2316/96

See application file for complete search history.

(56) References Cited

U.S. PATENT DOCUMENTS

| | | | |
|---|---|---|---|
| 6,703,489 B1 | 3/2004 | Ish-Horowicz | |
| 7,754,206 B2 | 7/2010 | Clarke | |
| 2004/0101847 A1 | 5/2004 | Freier et al. | |
| 2008/0317760 A1 | 12/2008 | Gurney | |
| 2009/0081238 A1 | 3/2009 | Siebel | |
| 2010/0080808 A1 | 4/2010 | Siebel et al. | |
| 2010/0111958 A1 | 5/2010 | Gurney et al. | |
| 2010/0196385 A1 | 8/2010 | Bedian | |
| 2014/0314749 A1 | 10/2014 | French et al. | |
| 2015/0232568 A1* | 8/2015 | Siebel ................ | C07K 16/2896 424/139.1 |

FOREIGN PATENT DOCUMENTS

| | | |
|---|---|---|
| WO | 2004/019921 A2 | 3/2004 |
| WO | 2006/135949 | 12/2006 |
| WO | 2008/057144 A2 | 5/2008 |
| WO | 2008/140826 A1 | 11/2008 |
| WO | 2009/124931 A2 | 10/2009 |
| WO | 2010005566 | 1/2010 |
| WO | WO 2010/005566 A2 | 1/2010 |
| WO | 2010039832 | 4/2010 |
| WO | WO 2011/063237 A2 | 5/2011 |
| WO | WO 2013/052155 A1 | 4/2013 |
| WO | WO 2013/052155 A9 | 4/2013 |
| WO | 2013/192550 A2 | 12/2013 |
| WO | WO 2014/028446 A1 | 2/2014 |
| WO | 2014/151866 A1 | 9/2014 |

OTHER PUBLICATIONS

Cao et al. Osteopontin as potential biomarker and therapeutic target in gastric and liver cancers. World J Gastroenterol 18(30): 3923-3930, 2012.*
Gotoh et al. Overexpression of osteopontin in hepatocellular carcinoma. Pathol Int 52: 19-24, 2002.*
Ho et al. Hepatology 55(3): 833-845, 2012.*
Shin et al. SPP1 polymorphisms associated with HBV clearance and HCC occurrence. Int J Epidemiol 36: 1001-1008, 2007.*
Yuen et al. Serological markers of liver cancer. Best Pract Res Clin Gastroenterol 19(1): 91-99, 2005.*
Ngo et al. Computational complexitiy, protein structure prediction, and the levinthal paradox. The Protein Folding Problem and Tertiary Structure Prediction, Boston: Birkhauser, 1994; pp. 491-495.*
Andrisani et al. Gene signatures in hepatocellular carcinoma (HCC). Sem Cancer Biol 21: 4-9, 2011.*
Imrich et al. EpCAM and its potential role in tumor-initiating cells. Cell Adhesion Migration 6: 30-38, 2012.*
Pang et al. Cancer stem cell as a potential therapeutic target in hepatocellular carcinoma. Current Cancer Drug Targets 12: 1081-1094, 2012.*
Artavanis-Tsakonas et al., "Choosing a cell fate: a view from the Notch locus" Reviews 7(11-12) ( 1991).
Bork, et al., "Go hunting in sequence databases but watch out for the traps" Trends in Genetics 12(10):425-427 (Oct. 1996).
Bork, "Powers and Pitfalls in Sequence Analysis: The 70% hurdle" Genome Research(10):398-400 ( 2000).

(Continued)

*Primary Examiner* — Bridget E Bunner
(74) *Attorney, Agent, or Firm* — McNeill Baur PLLC

(57) ABSTRACT

The present invention relates to methods of treating liver cancer using a Notch signaling inhibitor. Compositions and methods for the treatment of liver cancers are also provided.

17 Claims, 38 Drawing Sheets

(56) References Cited

OTHER PUBLICATIONS

Brenner, "Errors in genome annotation" Trends in Genetics 15(4):132-133 ( 1999).
Brorson, "Mutational analysis of avidity and fine specificity of anti-levan antibodies" J Immunol (added article title info), 163:6694-6701 (Dec. 1999).
Brummell et al. et al., "Probing the combining site of an anti-carbohydrate antibody by saturation-mutagenesis: role of the heavy-chain CDR3 residues" Biochemistry 32(4):1180-1187 (Feb. 1993).
Burks, E., et al. et al., "In vitro scanning saturation mutagenesis of an antibody binding pocket" P Natl Acad Sci USA 94:412-417 ( 1997).
Coleman, P.M., "Effects of amino acid sequence changes on anti-body-antigen interactions" Res Immunol 145:33-36 ( 1994).
Darwiche et al., "Inhibition of Notch signaling affects hepatic oval cell response in rat model of 2AAF-PH" Dove Press 3:89-98 ( 2011).
Doerks et al., "Protein annotation: detective work for function prediction" Trends in Genetics 14(6):248-250 ( 1998).
Dorothy French, DVM. PhD, DACVP, "Microarray analysis reveals signaling pathways critical for hepatic progenitor cell survival and self-renewal" Slides ASIP Meeting, pp. 53 ( Apr. 8, 2011).
Fan B et al., "Cholangiocarcinomas can originate from hepatocytes in mice" The Journal of clinical investigation 122(8):2911-2915 ( 2012).
Fiorotto, R. et al., "Progenitor Cell Activation and Liver Repair is Altered in Notch2 and RBP-J kappa-Defective Mice Exposed to Cholestatic Injuries" Journal of Hepatology 52(1):S45 (Apr. 2010).
Gao et al., "Expression of Jagged1 and its association with hepatitis B virus X protein in hepatocellular carcinoma" Biochemical and Biophysical Research Communications 356:341-347 ( 2007).
Gao et al., "Notch1 activation contributes to tumor cell growth and proliferation in human hepatocellular carcinoma HepG2 and SMMC7721 cells" International journal of oncology 41(5):1773-1781 ( 2012).
Geisler et al., "Liver-Specific Inactivation of Notch2, but not Notch1, Compromises Intrahepatic Bile Duct Development in Mice" Live Biology/Pathobiology 48(2):607-616 (Aug. 2008).
Groth et al., "Therapeutic Approaches to Modulating Notch Signaling: Current challenges and future prospects" Seminars in Cell & Development Biology 23:465-472 ( 2012).
Hattori et al., "Expression of the RNA-binding protein Musashi1 in adult liver stem-like cells" Hepatology Research 40:432-437, 2010.
Jang et al., "The structural basis for DNA binding by an anti-DNA autoantibody" Mol Immunol. 35(18):1207-17 (Dec. 1998).
Jensen et al., "Transit-amplifying ductal (oval) cells and their hepatocytic progeny are characterized by a novel and distinctive expression of delta-like protein/preadipocyte factor 1/fetal antigen 1." Am Journal Physiol 164(4):1347-1359 ( 2004).
Kobayashi, H., et al. et al., "Tryptophan H33 plays an important role in pyrimidin (6-4) pyrimidone photoproduct binding by a high-affinity antibody" Protein Eng 12(10):879-884 ( 1999).
Koch et al., "Notch and Cancer: a double-edged sword" Cellular and Molecular Life Sciences 64:2746-2762 ( 2007).
Louvi et al., "Notch and disease: A growing field" Seminars in Cell & Development Biology 23:473-480 ( 2012).
Lozier et al., "Notch signaling regulates bile duct morphogenesis in mice" PLoS One 3(3):e1851 ( 2008).
McCright et al., "A mouse model of Alagille syndrome: Notch2 as a genetic modifier of Jag1 haploinsufficiency" Development 129(4):1075-82 (Feb. 2002).
Mullendore et al., "Ligand-dependent Notch Signaling is Involved in Tumor Initiation and Tumor Maintenance in Pancreatic Cancer" Clinical Cancer Research 15:2291-2301 (Apr. 1, 2009).
Nijjar et al., "Notch receptor expression in adult human liver: a possible role in bile duct formation and hepatic neovascularization" Hepatology 34:1184-1192 ( 2001).
Nishina et al., "Restored expression of the tumor suppressor gene RUNX3 reduces cancer stem cells in hepatocellular carcinoma by suppressing Jagged1-Notch signaling" Oncology Reports 26:523-531 ( 2011).
Oda et al., "Mutations in the human Jagged1 gene are responsible for Alagille syndrome" Nat Genet. 16:235-42 (Jul. 1997).
Piccoli et al., "Alagille syndrome and the Jagged1 gene" Semin Liver Dis. 21(4):525-34 ( 2001).
Pikarsky et al., "NF-kb functions as a tumour promotor in inflammation-associated cancer" Nature 43:461-468 (Sep. 23, 2004).
Qi et al., "Notch1 signaling inhibits growth of human hepatocellular carcinoma through induction of cell cycle arrest and apoptosis" Cancer Research(63):8323-8329 (Dec. 1, 2003).
Ryan et al., "Bile duct proliferation in Jag1/fringe heterozygous mice identifies candidate modifiers of the Alagille syndrome hepatic phenotype" Hepatology 48(6):1989-97 ( 2008).
Sakurai et al., "Loss of hepatic NF-kb activity enhances chemical hepatocarcinogenesis throug sustained c-Jun N-terminal kinase 1 activation" PNAS 103(28):10544-10551 (Jul. 11, 2006).
Sekiya et al., "Intrahepatic cholangiocarcinoma can arise from Notch-mediated conversion of hepatocytes" The Journal of Clinical Investigation 122(11):3914-3918 ( 2012).
Shen et al., "GSI-has a better effect in inhibiting hepatocellular carcinoma cell growth than GSI-X, or GSI-XXI" Anticancer Drugs 23:683-690 ( 2012).
Skolnick et al., "From genes to protein structure and function: novel applications of computational approaches in the genomic era" Trends in Biotech. 18(1):34-39 ( 2000).
Smith et al., "The challenges of genome sequence annotation of 'the devil is in the details'" Nature Biotech(15):1222-1223 ( 1997).
Sparks et al., "Notch signaling regulates formation of the three-dimensional architecture of intrahepatic bile ducts in mice" Hepatology 51(4):1391-400 ( 2010).
Tanimizu et al., "Notch signaling control hepatoblast differentiation by altering the expression of liver-enriched transcription factors" J Cell Science 117:3165-3174 ( 2004).
Tchorz et al., "Notch2 Signaling Promotes Biliary Epithelial Cell Fate Specification and Tubulogenesis During Bile Duct Development in Mice" Hepatology 50(3):871-879 (Sep. 2009).
Tokuriki, et al., "Stability effects of mutations and protein evolvability" Current Opinion in Structural Biology 19:596-604 (2009).
Viatour et al., "Notch signaling inhibits hepatocellular carcinoma following inactivation of the RB pathway" The Journal of Experimental Medicine 208(10):1963-1976 (Aug. 29, 2011).
Villanueva et al., "Notch Signaling is Activated in Human Hepatocellular Carcinoma and Induces Tumor Formation in Mice" Gastroenterology 143:1660-1669 ( 2012).
Wakabayashi et al., "Regulation of Notch1 Signaling by Nrf2: Implications for Tissue Regeneration" Science Signaling 3(130):1-11 (Jul. 13, 2010).
Wang et al., "Hepatitis B Virus X protein promotes the growth of hepatocellular carcinoma by modulation of the Notch signaling pathway" Oncology Reports 27:1170-1176 ( 2012).
Wang et al., "Notch1 signaling contributes to the oncogenic effect of HBx on human hepatic cells" Biotechnol. Lett 35:29-37 ( 2012).
Wang et al., "Notch1 signaling sensitizes tumor necrosis factor-related apoptosis-inducing ligand-induced apoptosis in human hepatocellular carcinoma cells by inhibiting Akt/Hdm2-mediated p53 degradation and up-regulating p53-dependent DR5 expression" Journal of Biological Chemistry 284(24):16183-16190 ( 2009).
Wells, "Additivity of Mutational Effects in Proteins" Biochemistry 29:8509-8517 (1990).
Wu et al. et al., "Therapeutic Antibody targeting of individual Notch receptors" Nature 464:1052-1057 ( 2010).
Wu et al., "Notch Signaling and its role in breast cancer" Frontiers in Bioscience 12:4370-4384 ( 2007).
Xu et al., "Yes-Associated Protein is an Independent Prognostic Marker in Hepatocellular Carcinoma" Cancer(115):4576-85 (Oct. 1, 2009).
Zender et al., "Identification and Validation of Oncogenes in Liver Cancer Using an Integrative Oncogenomic Approach" Cell(125):1253-1267 (Jun. 30, 2006).

(56) References Cited

OTHER PUBLICATIONS

Zuener et al., "The Notch2-Jagged1 interaction mediates stem cell factor signaling in erythropoiesis" Cell Death Differ. 18(2):371-80 ( 2011).
Zhou et al., "Downregulation of the Notch signaling pathway inhibits hepatocellular carcinoma cell invasion by inactivation of matrix metalloproteinase-2 and-9 and vascular endothelial growth factor" Oncology reports 28(3):874-882 ( 2012).
Zhou et al., "The Down-Regulation of Notch1 Inhibits the Invasion and Migration of Hepatocellular Carcinoma Cells by Inactivating the Cyclooxygenase-2/Snail/E-cadherin Pathway In Vitro" Dig. Dis Sci ( 2012).
Dill et al., "Constitutive Notch2 Signaling Induces Hepatic Tumors in Mice," Hepatology 57: 1607-1619 (2013).
Ho et al, "Advances in Liver Cancer Antibody Therapies," Biodrugs 25(5): 275-284 (2011).
International Search Report and Written Opinion, mailed Aug. 20, 2014, for International App. No. PCT/US2014/026588, filed Mar. 13, 2014 (23 pages).
Wu et al., "Therapeutic antibody targeting of individual Notch receptors," Nature 464(7291):1052-1057 plus Methods (2 pages) (2010).
Chen et al., "An antibody drug conjugate targeting PMEL17" J. Biol. Chem. (Manuscript M112.361485), (May 21, 2012).
Dooley et al., "Notch Signaling Plays a Critical Role in Experimental and Human Liver Fibrogenesis" J. Hepatol. 52( SUPPL 1):S48 ( 2010).
Huntzicker et al., "Differential Effects of Targeting Notch Receptors in a Mouse Model of Liver Cancer" Hepatology 61:942-952 ( 2015).
International Search Report and Written Opinion for PCT Application No. PCT/US2015/015456, filed Feb. 11, 2015, pp. 13 (mailed May 7, 2015).
International Search Report for International Patent Application No. PCT/US2013/054664, pp. 5 (mailed Dec. 3, 2013).
Litten et al., "Activated NOTCH2 is Overexpressed in Hepatoblastomas: An Immunohistochemical Study" Pediatric Develop. Pathol. 14:378-383 ( 2011).
Orr et al., "Mechanism of Action of the Antifibrogenic Compound Gliotoxin in Rat Liver Cells" Hepatology 40:232-242 ( 2004).
Spee et al., "Chacterisation of the activated liver progenitor cell niche, potential involvement of Wnt and Notch signalling" Gut (abstract only (2 pages)), 59:247-257 ( 2010).
Written Opinion for International Patent Application No. PCT/US2013/054664, pp. 5 (mailed Dec. 3, 2013).

* cited by examiner

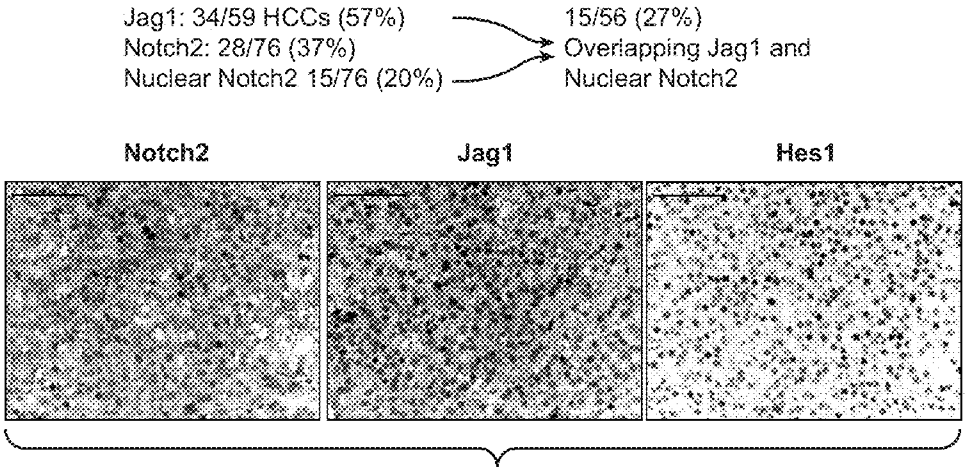

FIG. 7B

Human Notch2 NRR (SEQ ID NO: 73)

PATCLSQYCADKARDGVCDEACNSHACQWDGGDCSLTMENPWANCSSPLPCWDYI
NNQCDELCNTVECLFDNFECQGNSKTCKYDKYCADHFKDNHCDQGCNSEECGWDG
LDCAADQPENLAEGTLVIVVLMPPEQLLQDARSFLRALGTLLHTNLRIKRDSQGELMVY
PYYGEKSAAMKKQRMTRRSLPGEQEQEVAGSKVFLEIDNRQCVQDSDHCFKNTDAA
AALLASHAIQGTLSYPLVSVVSESLTPERTQ

FIG. 8A

Mouse Notch2 NRR (SEQ ID NO: 74)

PATCQSQYCADKARDGICDEACNSHACQWDGGDCSLTMEDPWANCTSTLRCWEYIN
NQCDEQCNTAECLFDNFECQRNSKTCKYDKYCADHFKDNHCDQGCNSEECGWDGL
DCASDQPENLAEGTLIIVVLLPPEQLLQDSRSFLRALGTLLHTNLRIKQDSQGALMVYPY
FGEKSAAMKKQKMTRRSLPEEQEQEQEVIGSKIFLEIDNRQCVQDSDQCFKNTDAAAA
LLASHAIQGTLSYPLVSVFSELESPRNAQ

FIG. 8B

HUMAN Notch2 (SEQ ID NO: 75)

MPALRPALLWALLALWLCCAAPAHALQCRDGYEPCVNEGMCVTYHNGTGYCKCPEGFLGEY
CQHRDPCEKNRCQNGGTCVAQAMLGKATCRCASGFTGEDCQYSTSHPCFVSRPCLNGGTC
HMLSRDTYECTCQVGFTGKECQWTDACLSHPCANGSTCTTVANQFSCKCLTGFTGQKCETD
VNECDIPGHCQHGGTCLNLPGSYQCQCPQGFTGQYCDSLYVPCAPSPCVNGGTCRQTGDFT
FECNCLPGFEGSTCERNIDDCPNHRCQNGGVCVDGVNTYNCRCPPQWTGQFCTEDVDECLL
QPNACQNGGTCANRNGGYGCVCVNGWSGDDCSENIDDCAFASCTPGSTCIDRVASFSCMCP
EGKAGLLCHLDDACISNPCHKGALCDTNPLNGQYICTCPQGYKGADCTEDVDECAMANSNPC
EHAGKCVNTDGAFHCECLKGYAGPRCEMDINECHSDPCQNDATCLDKIGGFTCLCMPGFKGV
HCELEINECQSNPCVNNGQCVDKVNRFQCLCPPGFTGPVCQIDIDDCSSTPCLNGAKCIDHPN
GYECQCATGFTGVLCEENIDNCDPDPCHHGQCQDGIDSYTCICNPGYMGAICSDQIDECYSSP
CLNDGRCIDLVNGYQCNCQPGTSGVNCEINFDDCASNPCIHGICMDGINRYSCVCSPGFTGQR
CNIDIDECASNPCRKGATCINGVNGFRCICPEGPHHPSCYSQVNECLSNPCIHGNCTGGLSGY
KCLCDAGWVGINCEVDKNECLSNPCQNGGTCDNLVNGYRCTCKKGFKGYNCQVNIDECASN
PCLNQGTCFDDISGYTCHCVLPYTGKNCQTVLAPCSPNPCENAAVCKESPNFESYTCLCAPG
WQGQRCTIDIDECISKPCMNHGLCHNTQGSYMCECPPGFSGMDCEEDIDDCLANPCQNGGS
CMDGVNTFSCLCLPGFTGDKCQTDMNECLSEPCKNGGTCSDYVNSYTCKCQAGFDGVHCEN
NINECTESSCFNGGTCVDGINSFSCLCPVGFTGSFCLHEINECSSHPCLNEGTCVDGLGTYRC
SCPLGYTGKNCQTLVNLCSRSPCKNKGTCVQKKAESQCLCPSGWAGAYCDVPNVSCDIAASR
RGVLVEHLCQHSGVCINAGNTHYCQCPLGYTGSYCEEQLDECASNPCQHGATCSDFIGGYRC
ECVPGYQGVNCEYEVDECQNQPCQNGGTCIDLVNHFKCSCPPGTRGLLCEENIDDCARGPH
CLNGGQCMDRIGGYSCRCLPGFAGERCEGDINECLSNPCSSEGSLDCIQLTNDYLCVCRSAFT
GRHCETFVDVCPQMPCLNGGTCAVASNMPDGFICRCPPGFSGARCQSSCGQVKCRKGEQC
VHTASGPRCFCPSPRDCESGCASSPCQHGGSCHPQRQPPYYSCQCAPPFSGSRCELYTAPP
STPPATCLSQYCADKARDGVCDEACNSHACQWDGGDCSLTMENPWANCSSPLPCWDYINN
QCDELCNTVECLFDNFECQGNSKTCKYDKYCADHFKDNHCDQGCNSEECGWDGLDCAADQ
PENLAEGTLVIVVLMPPEQLLQDARSFLRALGTLLHTNLRIKRDSQGELMVYPYYGEKSAAMKK
QRMTRRSLPGEQEQEVAGSKVFLEIDNRQCVQDSDHCFKNTDAAAALLASHAIQGTLSYPLVS
VVSESLTPERTQLLYLLAVAVVIILFIILLGVIMAKRKRKHGSLWLPEGFTLRRDASNHKRREPVG
QDAVGLKNLSVQVSEANLIGTGTSEHWVDDEGPQPKKVKAEDEALLSEEDDPIDRRPWTQQH
LEAADIRRTPSLALTPPQAEQEVDVLDVNVRGPDGCTPLMLASLRGGSSDLSDEDEDAEDSSA
NIITDLVYQGASLQAQTDRTGEMALHLAARYSRADAAKRLLDAGADANAQDNMGRCPLHAAVA
ADAQGVFQILIRNRVTDLDARMNDGTTPLILAARLAVEGMVAELINCQADVNAVDDHGKSALHW
AAAVNNVEATLLLLKNGANRDMQDNKEETPLFLAAREGSYEAAKILLDHFANRDITDHMDRLPR
DVARDRMHHDIVRLLDEYNVTPSPPGTVLTSALSPVICGPNRSFLSLKHTPMGKKSRRPSAKST
MPTSLPNLAKEAKDAKGSRRKKSLSEKVQLSESSVTLSPVDSLESPHTYVSDTTSSPMITSPGIL
QASPNPMLATAAPPAPVHAQHALSFSNLHEMQPLAHGASTVLPSVSQLLSHHHIVSPGSGSAG
SLSRLHPVPVPADWMNRMEVNETQYNEMFGMVLAPAEGTHPGIAPQSRPPEGKHITTPREPL
PPIVTFQLIPKGSIAQPAGAPQPQSTCPPAVAGPLPTMYQIPEMARLPSVAFPTAMMPQQDGQ
VAQTILPAYHPFPASVGKYPTPPSQHSYASSNAAERTPSHSGHLQGEHPYLTPSPESPDQWSS
SSPHSASDWSDVTTSPTPGGAGGGQRGPGTHMSEPPHNNMQVYA

*FIG. 8C*

HUMAN Notch2 (SEQ ID NO: 76)

MPDLRPAALRALLWLWLCGAGPAHALQCRGGQEPCVNEGTCVTYHNGTGFCRCPEGFLGEY
CQHRDPCEKNRCQNGGTCVPQGMLGKATCRCAPGFTGEDCQYSTSHPCFVSRPCQNGGTC
HMLSRDTYECTCQVGFTGKQCQWTDACLSHPCENGSTCTSVASQFSCKCPAGLTGQKCEAD
INECDIPGRCQHGGTCLNLPGSYRCQCGQGFTGQHCDSPYVRGLPCVNGGTCRQTGDFTLE
CNCLPGFEGSTCERNIDDCPNHKCQNGGVCVDGVNTYNCRCPPQWTGQFCTEDVDECLLQP
NACQNGGTCTNRNGGYGCVCVNGWSGDDCSENIDDCAYASCTPGSTCIDRVASFSCLCPEG
KAGLLCHLDDACISNPCHKGALCDTNPLNGQYICTCPQGYKGADCTEDVDECAMANSNPCEH
AGKCVNTDGAFHCECLKGYAGPRCEMDINECHSDPCQNDATCLDKIGGFTCLCMPGFKGVHC
ELEVNECQSNPCVNNGQCVDKVNRFQCLCPPGFTGPVCQIDIDDCSSTPCLNGAKCIDHPNG
YECQCATGFTGILCDENIDNCDPDPCHHGQCQDGIDSYTCICNPGYMGAICSDQIDECYSSPCL
NDGRCIDLVNGYQCNCQPGTSGLNCEINFDDCASNPCMHGVCVDGINRYSCVCSPGFTGQR
CNIDIDECASNPCRKGATCINDVNGFRCICPEGPHHPSCYSQVNECLSNPCIHGNCTGGLSGY
KCLCDAGWVGVNCEVDKNECLSNPCQNGGTCNNLVNGYRCTCKKGFKGYNCQVNIDECASN
PCLNQGTCFDDVSGYTCHCMLPYTGKNCQTVLAPCSPNPCENAAVCKEAPNFESFSCLCAPG
WQGKRCTVDVDECISKPCMNNGVCHNTQGSYVCECPPGFSGMDCEEDINDCLANPCQNGG
SCVDHVNTFSCQCHPGFIGDKCQTDMNECLSEPCKNGGTCSDYVNSYTCTCPAGFHGVHCE
NNIDECTESSCFNGGTCVDGINSFSCLCPVGFTGPFCLHDINECSSNPCLNAGTCVDGLGTYR
CICPLGYTGKNCQTLVNLCSRSPCKNKGTCVQEKARPHCLCPPGWDGAYCDVLNVSCKAAAL
QKGVPVEHLCQHSGICINAGNTHHCQCPLGYTGSYCEEQLDECASNPCQHGATCNDFIGGYR
CECVPGYQGV

*FIG. 8D*

HUMAN Jag1 (SEQ ID NO: 78)

MRSPRTRGRSGRPLSLLLALLCALRAKVCGASGQFELEILSMQNVNGELQNGNCCGGARN
PGDRKCTRDECDTYFKVCLKEYQSRVTAGGPCSFGSGSTPVIGGNTFNLKASRGNDRNRI
VLPFSFAWPRSYTLLVEAWDSSNDTVQPDSIIEKASHSGMINPSRQWQTLKQNTGVAHFE
YQIRVTCDDYYYGFGCNKFCRPRDDFFGHYACDQNGNKTCMEGWMGPECNRAICRQGCSP
KHGSCKLPGDCRCQYGWQGLYCDKCIPHPGCVHGICNEPWQCLCETNWGGQLCDKDLNYC
GTHQPCLNGGTCSNTGPDKYQCSCPEGYSGPNCEIAEHACLSDPCHNRGSCKETSLGFEC
ECSPGWTGPTCSTNIDDCSPNNCSHGGTCQDLVNGFKCVCPPQWTGKTCQLDANECEAKP
CVNAKSCKNLIASYYCDCLPGWMGQNCDININDCLGQCQNDASCRDLVNGYRCICPPGYA
GDHCERDIDECASNPCLNGGHCQNEINRFQCLCPTGFSGNLCQLDIDYCEPNPCQNGAQC
YNRASDYFCKCPEDYEGKNCSHLKDHCRTTPCEVIDSCTVAMASNDTPEGVRYISSNVCG
PHGKCKSQSGGKFTCDCNKGFTGTYCHENINDCESNPCRNGGTCIDGVNSYKCICSDGWE
GAYCETNINDCSQNPCHNGGTCRDLVNDFYCDCKNGWKGKTCHSRDSQCDEATCNNGGTC
YDEGDAFKCMCPGGWEGTTCNIARNSSCLPNPCHNGGTCVVNGESFTCVCKEGWEGPICA
QNTNDCSPHPCYNSGTCVDGDNWYRCECAPGFAGPDCRININECQSSPCAFGATCVDEIN
GYRCVCPPGHSGAKCQEVSGRPCITMGSVIPDGAKWDDDCNTCQCLNGRIACSKVWCGPR
PCLLHKGHSECPSGQSCIPILDDQCFVHPCTGVGECRSSSLQPVKTKCTSDSYYQDNCAN
ITFTFNKEMMSPGLTTEHICSELRNLNILKNVSAEYSIYIACEPSPSANNEIHVAISAED
IRDDGNPIKEITDKIIDLVSKRDGNSSLIAAVAEVRVQRRPLKNRTDFLVPLLSSVLTVA
WICCLVTAFYWCLRKRRKPGSHTHSASEDNTTNNVREQLNQIKNPIEKHGANTVPIKDYE
NKNSKMSKIRTHNSEVEEDDMDKHQQKARFAKQPAYTLVDREEKPPNGTPTKHPNWTNKQ
DNRDLESAQSLNRMEYIV

MURINE Jag1 (SEQ ID NO:79)

MRSPRTRGRPGRPLSLLLALLCALRAKVCGASGQFELEILSMQNVNGELQNGNCCGGVRN
PGDRKCTRDECDTYFKVCLKEYQSRVTAGGPCSFGSGSTPVIGGNTFNLKASRGNDRNRI
VLPFSFAWPRSYTLLVEAWDSSNDTIQPDSIIEKASHSGMINPSRQWQTLKQNTGIAHFE
YQIRVTCDDHYYGFGCNKFCRPRDDFFGHYACDQNGNKTCMEGWMGPDCNKAICRQGCSP
KHGSCKLPGDCRCQYGWQGLYCDKCIPHPGCVHGTCNEPWQCLCETNWGGQLCDKDLNYC
GTHQPCLNRGTCSNTGPDKYQCSCPEGYSGPNCEIAEHACLSDPCHNRGSCKETSSGFEC
ECSPGWTGPTCSTNIDDCSPNNCSHGGTCQDLVNGFKCVCPPQWTGKTCQLDANECEAKP
CVNARSCKNLIASYYCDCLPGWMGQNCDININDCLGQCQNDASCRDLVNGYRCICPPGYA
GDHCERDIDECASNPCLNGGHCQNEINRFQCLCPTGFSGNLCQLDIDYCEPNPCQNGAQC
YNRASDYFCKCPEDYEGKNCSHLKDHCRTTTCEVIDSCTVAMASNDTPEGVRYISSNVCG
PHGKCKSQSGGKFTCDCNKGFTGTYCHENINDCESNPCKNGGTCIDGVNSYKCICSDGWE
GAHCENNINDCSQNPCHYGGTCRDLVNDFYCDCKNGWKGKTCHSRDSQCDEATCNNGGTC
YDEVDTFKCMCPGGWEGTTCNIARNSSCLPNPCHNGGTCVVNGDSFTCVCKEGWEGPICT
QNTNDCSPHPCYNSGTCVDGDNWYRCECAPGFAGPDCRININECQSSPCAFGATCVDEIN
GYQCICPPGHSGAKCHEVSGRSCITMGRVILDGAKWDDDCNTCQCLNGRVACSKVWCGPR
PCRLHKSHNECPSGQSCIPVLDDQCFVRPCTGVGECRSSSLQPVKTKCTSDSYYQDNCAN
ITFTFNKEMMSPGLTTEHICSELRNLNILKNVSAEYSIYIACEPSLSANNEIHVAISAED
IRDDGNPVKEITDKIIDLVSKRDGNSSLIAAVAEVRVQRRPLKNRTDFLVPLLSSVLTVA
WVCCLVTAFYWCVRKRRKPSSHTHSAPEDNTTNNVREQLNQIKNPIEKHGANTVPIKDYE
NKNSKMSKIRTHNSEVEEDDMDKHQQKVRFAKQPVYTLVDREEKAPSGTPTKHPNWTNKQ
DNRDLESAQSLNRMEYIV

*FIG. 9*

Expressed protein murine Jag1-DSL-EGF1-4 (mouse Jag1 antigen)
(SEQ ID NO: 80)

ADLGSQFELEILSMQNVNGELQNGNCCGGVRNPGDRKCTRDECDTYFKVCLKEYQSRVTAG
GPCSFGSGSTPVIGGNTFNLKASRGNDRNRIVLPFSFAWPRSYTLLVEAWDSSNDTIQPDSIIE
KASHSGMINPSRQWQTLKQNTGIAHFEYQIRVTCDDHYYGFGCNKFCRPRDDFFGHYACDQN
GNKTCMEGWMGPDCNKAICRQGCSPKHGSCKLPGDCRCQYGWQGLYCDKCIPHPGCVHGT
CNEPWQCLCETNWGGQLCDKDLNYCGTHQPCLNRGTCSNTGPDKYQCSCPEGYSGPNCEI
AEHACLSDPCHNRGSCKETSSGFECECSPGWTGPTCSTNIDDEFGLVPRGSGHHHHHH

*FIG. 10A*

Expressed protein human Jag1-DSL-EGF1-4 (human Jag1 antigen)
(SEQ ID NO: 28)

QFELEILSMQNVNGELQNGNCCGGARNPGDRKCTRDECDTYFKVCLKEYQSRVTAGGPCSF
GSGSTPVIGGNTFNLKASRGNDRNRIVLPFSFAWPRSYTLLVEAWDSSNDTVQPDSIIEKASHS
GMINPSRQWQTLKQNTGVAHFEYQIRVTCDDYYYGFGCNKFCRPRDDFFGHYACDQNGNKT
CMEGWMGPECNRAICRQGCSPKHGSCKLPGDCRCQYGWQGLYCDKCIPHPGCVHGICNEP
WQCLCETNWGGQLCDKDLNYCGTHQPCLNGGTCSNTGPDKYQCSCPEGYSGPNCEIAEHA
CLSDPCHNRGSCKETSLGFECECSPGWTGPTCSTNIDD

*FIG. 10B*

Human Secreted Phosphoprotein1 (SPP1)
(SEQ ID NO: 29)

MRIAVICFCLLGITCAIPVKQADSGSSEEKQLYNKYPDAVATWLNPDPSQKQNLLAPQNA
VSSEETNDFKQETLPSKSNESHDHMDDMDDEDDDDHVDSQDSIDSNDSDDVDDTDDSHQS
DESHHSDESDELVTDFPTDLPATEVFTPVVPTVDTYDGRGDSVVYGLRSKSKKFRRPDIQ
YPDATDEDITSHMESEELNGAYKAIPVAQDLNAPSDWDSRGKDSYETSQLDDQSAETHSH
KQSRLYKRKANDESNEHSDVIDSQELSKVSREFHSHEFHSHEDMLVVDPKSKEEDKHLKF
RISHELDSASSEVN

*FIG. 11*

HVR-H1 Sequences - Antibody B and Affinity Matured Antibodies Derived from Antibody B

| | | Kabat Number | | | | | | | | | |
|---|---|---|---|---|---|---|---|---|---|---|---|
| Antibody | SEQ ID NO: | 26 | 27 | 28 | 29 | 30 | 31 | 32 | 33 | 34 | 35 |
| B, B-1, B-2, B-3 | 1 | G | Y | S | F | T | S | Y | G | M | S |

HVR-H2 Sequence - Antibody B and Affinity Matured Antibodies Derived from Antibody B

| | | Kabat Number | | | | | | | | | | | | | | | | | |
|---|---|---|---|---|---|---|---|---|---|---|---|---|---|---|---|---|---|---|---|
| Antibody # | SEQ ID NO: | 49 | 50 | 51 | 52 | 52a | 53 | 54 | 55 | 56 | 57 | 58 | 59 | 60 | 61 | 62 | 63 | 64 | 65 |
| B, B-1, B-2, B-3 | 3 | S | Y | I | Y | P | Y | S | G | A | T | Y | Y | A | D | S | V | K | G |

HVR-H3 Sequence - Antibody B and Affinity Matured Antibodies Derived from Antibody B

| | | Kabat Number | | | | | | | | | | | | |
|---|---|---|---|---|---|---|---|---|---|---|---|---|---|---|
| Antibody # | SEQ ID NO: | 95 | 96 | 97 | 98 | 99 | 100 | 100A | 100B | 100C | 100D | 100K | 101 | 102 |
| B, B-1, B-2, B-3 | 4 | H | S | G | Y | Y | R | I | S | S | A | M | D | V |

FIG. 12

HVR-L1 Sequences - Antibody B and Affinity Matured Antibodies Derived from Antibody B

| | | Kabat Number | | | | | | | | | | |
|---|---|---|---|---|---|---|---|---|---|---|---|---|
| Antibody # | SEQ ID NO: | 24 | 25 | 26 | 27 | 28 | 29 | 30 | 31 | 32 | 33 | 34 |
| B | 5 | R | A | S | Q | S | I | S | S | Y | L | A |
| B-1 | 6 | R | A | S | Q | S | N | R | R | F | L | A |
| B-2 | 7 | R | A | S | Q | S | V | R | S | F | L | A |
| B-3 | 8 | R | A | S | Q | N | I | K | R | F | L | A |
| Consensus | 9 | R | A | S | Q | S/N | I/N/V | S/R/K | S/R | Y/F | L | A |

HVR-L2 Sequences - Antibody B and Affinity Matured Antibodies Derived from Antibody B

| | | Kabat Number | | | | | | |
|---|---|---|---|---|---|---|---|---|
| Antibody # | SEQ ID NO: | 50 | 51 | 52 | 53 | 54 | 55 | 56 |
| B | 10 | G | A | S | S | R | A | S |
| B-1 | 11 | G | A | S | R | R | A | S |
| B-2 | 12 | R | A | S | I | R | A | S |
| B-3 | 13 | G | A | S | T | R | E | S |
| Consensus | 14 | G/R | A | S | S/R/I/T | R | A/E | S |

HVR-L3 Sequences - Antibody B and Affinity Matured Antibodies Derived from Antibody B

| | | Kabat Number | | | | | | | | |
|---|---|---|---|---|---|---|---|---|---|---|
| Antibody # | SEQ ID NO: | 89 | 90 | 91 | 92 | 93 | 94 | 95 | 96 | 97 |
| B | 15 | Q | Q | Y | Y | S | S | P | L | T |
| B-1 | 16 | Q | Q | Y | Y | I | S | P | L | T |
| B-2 | 17 | Q | Q | Y | Y | I | S | P | W | T |
| B-3 | 18 | Q | Q | Y | Y | R | S | P | H | T |
| Consensus | 19 | Q | Q | Y | Y | S/I/R | S | P | L/H/S | T |

FIG. 13

| Kabat Numbering | SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|---|
| Antibody B | 20 | E | V | Q | L | V | E | S | G | G | G | L | V | Q | P | G | G | S | L | R | L | S | C | A | A |
| Antibody B-1 | 20 | E | V | Q | L | V | E | S | G | G | G | L | V | Q | P | G | G | S | L | R | L | S | C | A | A |
| Antibody B-2 | 20 | E | V | Q | L | V | E | S | G | G | G | L | V | Q | P | G | G | S | L | R | L | S | C | A | A |
| Antibody B-3 | 20 | E | V | Q | L | V | E | S | G | G | G | L | V | Q | P | G | G | S | L | R | L | S | C | A | A |

Kabat - CDR H1

| | | 25 | 26 | 27 | 28 | 29 | 30 | 31 | 32 | 33 | 34 | 35 | 35A | 35B | 36 | 37 | 38 | 39 | 40 | 41 | 42 | 43 | 44 | 45 | 46 |
|---|---|---|---|---|---|---|---|---|---|---|---|---|---|---|---|---|---|---|---|---|---|---|---|---|---|
| Antibody B | 20 | S | G | Y | S | F | T | S | Y | G | M | S | . | . | W | V | R | Q | A | P | G | K | G | L | E |
| Antibody B-1 | 20 | S | G | Y | S | F | T | S | Y | G | M | S | . | . | W | V | R | Q | A | P | G | K | G | L | E |
| Antibody B-2 | 20 | S | G | Y | S | F | T | S | Y | G | M | S | . | . | W | V | R | Q | A | P | G | K | G | L | E |
| Antibody B-3 | 20 | S | G | Y | S | F | T | S | Y | G | M | S | . | . | W | V | R | Q | A | P | G | K | G | L | E |

Kabat - CDR H2

| | | 47 | 48 | 49 | 50 | 51 | 52 | 52A | 52B | 52C | 53 | 54 | 55 | 56 | 57 | 58 | 59 | 60 | 61 | 62 | 62 | 64 | 65 | 66 | 67 |
|---|---|---|---|---|---|---|---|---|---|---|---|---|---|---|---|---|---|---|---|---|---|---|---|---|---|
| Antibody B | 20 | W | V | S | Y | I | Y | P | . | . | Y | S | G | A | T | Y | Y | A | D | S | V | K | G | R | F |
| Antibody B-1 | 20 | W | V | S | Y | I | Y | P | . | . | Y | S | G | A | T | Y | Y | A | D | S | V | K | G | R | F |
| Antibody B-2 | 20 | W | V | S | Y | I | Y | P | . | . | Y | S | G | A | T | Y | Y | A | D | S | V | K | G | R | F |
| Antibody B-3 | 20 | W | V | S | Y | I | Y | P | . | . | Y | S | G | A | T | Y | Y | A | D | S | V | K | G | R | F |

| | | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 |
|---|---|---|---|---|---|---|---|---|---|---|---|---|---|---|---|---|---|---|---|---|---|---|---|---|---|
| Antibody B | 20 | T | I | S | A | D | T | S | K | N | T | A | Y | L | Q | M | N | S | L | R | A | E | D | T | A |
| Antibody B-1 | 20 | T | I | S | A | D | T | S | K | N | T | A | Y | L | Q | M | N | S | L | R | A | E | D | T | A |
| Antibody B-2 | 20 | T | I | S | A | D | T | S | K | N | T | A | Y | L | Q | M | N | S | L | R | A | E | D | T | A |
| Antibody B-3 | 20 | T | I | S | A | D | T | S | K | N | T | A | Y | L | Q | M | N | S | L | R | A | E | D | T | A |

FIG. 14A

Kabat - CDR H3

| Kabat Numbering | SEQ ID NO: | 89 | 90 | 91 | 92 | 93 | 94 | 95 | 96 | 97 | 98 | 99 | 100 | 100A | 100B | 100C | 100D | 100E | 100F | 100G | 100H | 100I | 100J | 100K | 100L |
|---|---|---|---|---|---|---|---|---|---|---|---|---|---|---|---|---|---|---|---|---|---|---|---|---|---|
| Antibody B | 20 | V | Y | Y | C | A | R | H | S | G | Y | Y | R | I | S | S | A | . | . | . | . | . | . | . | . |
| Antibody B-1 | 20 | V | Y | Y | C | A | R | H | S | G | Y | Y | R | I | S | S | A | . | . | . | . | . | . | . | . |
| Antibody B-2 | 20 | V | Y | Y | C | A | R | H | S | G | Y | Y | R | I | S | S | A | . | . | . | . | . | . | . | . |
| Antibody B-3 | 20 | V | Y | Y | C | A | R | H | S | G | Y | Y | R | I | S | S | A | . | . | . | . | . | . | . | . |

| | | 100M | 101 | 102 | 103 | 104 | 105 | 106 | 107 | 108 | 109 | 110 | 111 | 112 | 113 |
|---|---|---|---|---|---|---|---|---|---|---|---|---|---|---|---|
| Antibody B | 20 | M | D | V | W | G | Q | G | T | L | V | T | V | S | S |
| Antibody B-1 | 20 | M | D | V | W | G | Q | G | T | L | V | T | V | S | S |
| Antibody B-2 | 20 | M | D | V | W | G | Q | G | T | L | V | T | V | S | S |
| Antibody B-3 | 20 | M | D | V | W | G | Q | G | T | L | V | T | V | S | S |

FIG. 14B

| Kabat Numbering | SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| Antibody B | 22 | D | I | Q | M | T | Q | S | P | S | S | L | S | A | S | V | G | D | R | V | T | I | T | C |
| Antibody B-1 | 23 | D | I | Q | M | T | Q | S | P | S | S | L | S | A | S | V | G | D | R | V | T | I | T | C |
| Antibody B-2 | 24 | D | I | Q | M | T | Q | S | P | S | S | L | S | A | S | V | G | D | R | V | T | I | T | C |
| Antibody B-3 | 25 | D | I | Q | M | T | Q | S | P | S | S | L | S | A | S | V | G | D | R | V | T | I | T | C |

| | | Kabat - CDR L1 | | | | | | | | | | | | | | | | | | | | | | |
|---|---|---|---|---|---|---|---|---|---|---|---|---|---|---|---|---|---|---|---|---|---|---|---|---|
| | | 24 | 25 | 26 | 27 | 27A | 27B | 27C | 27D | 27E | 27F | 28 | 29 | 30 | 31 | 32 | 33 | 34 | 35 | 36 | 37 | 38 | 39 | 40 |
| Antibody B | 22 | R | A | S | Q | . | . | . | . | . | . | S | I | S | S | Y | L | A | W | Y | Q | Q | K | P |
| Antibody B-1 | 23 | R | A | S | Q | . | . | . | . | . | . | S | N | R | R | F | L | A | W | Y | Q | Q | K | P |
| Antibody B-2 | 24 | R | A | S | Q | . | . | . | . | . | . | S | V | R | S | F | L | A | W | Y | Q | Q | K | P |
| Antibody B-3 | 25 | R | A | S | Q | . | . | . | . | . | . | N | I | K | R | F | L | A | W | Y | Q | Q | K | P |

| | | | | | | | | | | | Kabat - CDR L2 | | | | | | | | | | | | | |
|---|---|---|---|---|---|---|---|---|---|---|---|---|---|---|---|---|---|---|---|---|---|---|---|---|
| | | 41 | 42 | 43 | 44 | 45 | 46 | 47 | 48 | 49 | 50 | 51 | 52 | 53 | 54 | 54A | 54B | 54C | 54D | 54E | 55 | 56 | 57 | 58 |
| Antibody B | 22 | G | K | A | P | K | L | L | I | Y | G | A | S | S | R | . | . | . | . | . | A | S | G | V |
| Antibody B-1 | 23 | G | K | A | P | K | L | L | I | Y | G | A | S | R | R | . | . | . | . | . | A | S | G | V |
| Antibody B-2 | 24 | G | K | A | P | K | L | L | I | Y | R | A | S | I | R | . | . | . | . | . | A | S | G | V |
| Antibody B-3 | 25 | G | K | A | P | K | L | L | I | Y | G | A | S | T | R | . | . | . | . | . | E | S | G | V |

| | | 59 | 60 | 61 | 62 | 63 | 64 | 65 | 66 | 66A | 66B | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|
| Antibody B | 22 | P | S | R | F | S | G | S | G | . | . | S | G | T | D | F | T | L | T | I | S | S | L | Q | P |
| Antibody B-1 | 23 | P | S | R | F | S | G | S | G | . | . | S | G | T | D | F | T | L | T | I | S | S | L | Q | P |
| Antibody B-2 | 24 | P | S | R | F | S | G | S | G | . | . | S | G | T | D | F | T | L | T | I | S | S | L | Q | P |
| Antibody B-3 | 25 | P | S | R | F | S | G | S | G | . | . | S | G | T | D | F | T | L | T | I | S | S | L | Q | P |

FIG. 15A

| Kabat Numbering | SEQ ID NO: | 81 | 82 | 83 | 84 | 85 | 86 | 87 | 88 | 89 | 90 | 91 | 92 | 93 | 94 | 95 | 95A | 95B | 95C | 95D | 95E | 95F | 96 | 97 |
|---|---|---|---|---|---|---|---|---|---|---|---|---|---|---|---|---|---|---|---|---|---|---|---|---|
| | | | | | | | | | | Kabat - CDR L3 | | | | | | | | | | | | | | |
| Antibody B | 22 | E | D | F | A | T | Y | Y | C | Q | Q | Y | Y | S | S | P | . | . | . | . | . | . | L | T |
| Antibody B-1 | 23 | E | D | F | A | T | Y | Y | C | Q | Q | Y | Y | I | S | P | . | . | . | . | . | . | L | T |
| Antibody B-2 | 24 | E | D | F | A | T | Y | Y | C | Q | Q | Y | Y | I | S | P | . | . | . | . | . | . | S | T |
| Antibody B-3 | 25 | E | D | F | A | T | Y | Y | C | Q | Q | Y | Y | R | S | P | . | . | . | . | . | . | H | T |

| | | 98 | 99 | 100 | 101 | 102 | 103 | 104 | 105 | 106 | 107 |
|---|---|---|---|---|---|---|---|---|---|---|---|
| Antibody B | 22 | F | G | Q | G | T | K | V | E | I | K |
| Antibody B-1 | 23 | F | G | Q | G | T | K | V | E | I | K |
| Antibody B-2 | 24 | F | G | Q | G | T | K | V | E | I | K |
| Antibody B-3 | 25 | F | G | Q | G | T | K | V | E | I | K |

*FIG. 15B*

| | FR1 | | FR2 | | |
|---|---|---|---|---|---|
| I | | | | | |
| A | QVQLVQSGAEVKKPGASVKVSCKASGYTFT | -H1- | WVRQAPGQGLEWMG | -H2- | RVTIT |
| B | QVQLVQSGAEVKKPGASVKVSCKAS | -H1- | WVRQAPGQGLEWM | -H2- | RVTIT |
| C | QVQLVQSGAEVKKPGASVKVSCKAS | -H1- | WVRQAPGQGLEWM | -H2- | RVTIT |
| D | QVQLVQSGAEVKKPGASVKVSCKAS | -H1- | WVRQAPGQGLEWM | -H2- | RVTIT |
| II | | | | | |
| A | QVQLQESGPGLVKPSQTLSLTCTVSGGSVS | -H1- | WIRQPPGKGLEWIG | -H2- | RVTIS |
| B | QVQLQESGPGLVKPSQTLSLTCTVS | -H1- | WIRQPPGKGLEWI | -H2- | RVTIS |
| C | QVQLQESGPGLVKPSQTLSLTCTVS | -H1- | WIRQPPGKGLEWI | -H2- | RVTIS |
| D | QVQLQESGPGLVKPSQTLSLTCTVS | -H1- | WIRQPPGKGLEWI | -H2- | RVTIS |
| III | | | | | |
| A | EVQLVESGGGLVQPGGSLRLSCAASGFTFS | -H1- | WVRQAPGKGLEWVS | -H2- | RFTIS |
| B | EVQLVESGGGLVQPGGSLRLSCAAS | -H1- | WVRQAPGKGLEWV | -H2- | RFTIS |
| C | EVQLVESGGGLVQPGGSLRLSCAAS | -H1- | WVRQAPGKGLEWV | -H2- | RFTIS |
| D | EVQLVESGGGLVQPGGSLRLSCAAS | -H1- | WVRQAPGKGLEWV | -H2- | RFTIS |
| Acceptor - 1 | | | | | |
| A | EVQLVESGGGLVQPGGSLRLSCAASGFNIK | -H1- | WVRQAPGKGLEWVS | -H2- | RFTIS |
| B | EVQLVESGGGLVQPGGSLRLSCAAS | -H1- | WVRQAPGKGLEWV | -H2- | RFTIS |
| C | EVQLVESGGGLVQPGGSLRLSCAAS | -H1- | WVRQAPGKGLEWV | -H2- | RFTIS |
| Acceptor - 2 | | | | | |
| A | EVQLVESGGGLVQPGGSLRLSCAASGFNIK | -H1- | WVRQAPGKGLEWVS | -H2- | RFTIS |
| B | EVQLVESGGGLVQPGGSLRLSCAAS | -H1- | WVRQAPGKGLEWV | -H2- | RFTIS |
| C | EVQLVESGGGLVQPGGSLRLSCAAS | -H1- | WVRQAPGKGLEWV | -H2- | RFTIS |
| D | EVQLVESGGGLVQPGGSLRLSCAAS | -H1- | WVRQAPGKGLEWV | -H2- | RFTIS |

FIG. 16A

| | FR3 | | FR4 | SEQ ID NOs of FR1, FR2, FR3, FR4 |
|---|---|---|---|---|
| I | | | | |
| A | ADTSTSTAYMELSSLRSEDTAVYYCAR | -H3- | WGQGTLVTVSS | SEQ ID NO.: 32, 33, 34, 35 |
| B | ADTSTSTAYMELSSLRSEDTAVYYCAR | -H3- | WGQGTLVTVSS | SEQ ID NO.: 36, 37, 34, 35 |
| C | ADTSTSTAYMELSSLRSEDTAVYYCA | -H3- | WGQGTLVTVSS | SEQ ID NO.: 36, 37, 38, 35 |
| D | ADTSTSTAYMELSSLRSEDTAVYYC | -H3- | WGQGTLVTVSS | SEQ ID NO.: 36, 37, 39, 35 |
| II | | | | |
| A | VDTSKNQFSLKLSSVTAADTAVYYCAR | -H3- | WGQGTLVTVSS | SEQ ID NO.: 40, 41, 42, 35 |
| B | VDTSKNQFSLKLSSVTAADTAVYYCAR | -H3- | WGQGTLVTVSS | SEQ ID NO.: 43, 44, 42, 35 |
| C | VDTSKNQFSLKLSSVTAADTAVYYCA | -H3- | WGQGTLVTVSS | SEQ ID NO.: 43, 44, 45, 35 |
| D | VDTSKNQFSLKLSSVTAADTAVYYC | -H3- | WGQGTLVTVSS | SEQ ID NO.: 43, 44, 46, 35 |
| III | | | | |
| A | RDNSKNTLYLQMNSLRAEDTAVYYCAR | -H3- | WGQGTLVTVSS | SEQ ID NO.: 47, 48, 49, 35 |
| B | RDNSKNTLYLQMNSLRAEDTAVYYCAR | -H3- | WGQGTLVTVSS | SEQ ID NO.: 50, 51, 49, 35 |
| C | RDNSKNTLYLQMNSLRAEDTAVYYCA | -H3- | WGQGTLVTVSS | SEQ ID NO.: 50, 51, 52, 35 |
| D | RDNSKNTLYLQMNSLRAEDTAVYYC | -H3- | WGQGTLVTVSS | SEQ ID NO.: 50, 51, 53, 35 |
| Acceptor - 1 | | | | |
| A | ADTSKNTAYLQMNSLRAEDTAVYYCSR | -H3- | WGQGTLVTVSS | SEQ ID NO.: 54, 48, 55, 35 |
| B | ADTSKNTAYLQMNSLRAEDTAVYYCSR | -H3- | WGQGTLVTVSS | SEQ ID NO.: 50, 51, 55, 35 |
| C | ADTSKNTAYLQMNSLRAEDTAVYYCS | -H3- | WGQGTLVTVSS | SEQ ID NO.: 50, 51, 56, 35 |
| Acceptor - 2 | | | | |
| A | ADTSKNTAYLQMNSLRAEDTAVYYCAR | -H3- | WGQGTLVTVSS | SEQ ID NO.: 54, 48, 57, 35 |
| B | ADTSKNTAYLQMNSLRAEDTAVYYCAR | -H3- | WGQGTLVTVSS | SEQ ID NO.: 50, 51, 57, 35 |
| C | ADTSKNTAYLQMNSLRAEDTAVYYCA | -H3- | WGQGTLVTVSS | SEQ ID NO.: 50, 51, 58, 35 |
| D | ADTSKNTAYLQMNSLRAEDTAVYYC | -H3- | WGQGTLVTVSS | SEQ ID NO.: 50, 51, 59, 35 |

FIG. 16B

| | FR1 | | FR2 | | FR3 |
|---|---|---|---|---|---|
| kv1 | DIQMTQSPSSLSASVGDRVTITC | -L1- | WYQQKPGKAPKLLIY | -L2- | GVPSRFSGSGSGTDFTLTISSLQP |
| kv2 | DIVMTQSPLSLPVTPGEPASISC | -L1- | WYLQKPGQSPQLLIY | -L2- | GVPDRFSGSGSGTDFTLKISRVEA |
| kv3 | EIVLTQSPGTLSLSPGERATLSC | -L1- | WYQQKPGQAPRLLIY | -L2- | GIPDRFSGSGSGTDFTLTISRLEP |
| kv4 | DIVMTQSPDSLAVSLGERATINC | -L1- | WYQQKPGQPPKLLIY | -L2- | GVPDRFSGSGSGTDFTLTISSLQA |

| | | FR4 | SEQ ID NOs of FR1, FR2, FR3, FR4 |
|---|---|---|---|
| EDFATYYC | -L3- | FGQGTKVEIK | SEQ ID NO.: 60, 61, 62, 63 |
| EDVGVYYC | -L3- | FGQGTKVEIK | SEQ ID NO.: 64, 65, 66, 63 |
| EDFAVYYC | -L3- | FGQGTKVEIK | SEQ ID NO.: 67, 68, 69, 63 |
| EDVAVYYC | -L3- | FGQGTKVEIK | SEQ ID NO.: 70, 71, 72, 63 |

FIG. 17

Framework Sequences of huMAb4D5-8 Light Chain Variable Domain

LC-FR1 $^{1}$Asp Ile Gln Met Thr Gln Ser Pro Ser Ser Leu Ser Ala Ser Val Gly Asp Arg Val Thr Ile Thr Cys$^{23}$

LC-FR2 $^{35}$Trp Tyr Gln Gln Lys Pro Gly Lys Ala Pro Lys Leu Leu Ile Tyr$^{49}$

LC-FR3 $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$

LC-FR4 $^{98}$Phe Gly Gln Gly Thr Lys Val Glu Ile Lys$^{107}$

Framework Sequences of huMAb4D5-8 Heavy Chain Variable Domain

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$

HC-FR2 $^{36}$Trp Val Arg Gln Ala Pro Gly Lys Gly Leu Glu Trp Val$^{48}$

HC-FR3 $^{66}$Arg Phe Thr Ile Ser Ala Asp Thr Ser Lys Asn Thr Ala Tyr Leu Gln Met Asn$^{83}$ Ser$^{83a}$ Leu$^{83b}$ Arg$^{83c}$ Ala Glu Asp Thr Ala Val Tyr Tyr Cys$^{92}$

HC-FR4 $^{103}$Trp Gly Gln Gly Thr Leu Val Thr Val Ser Ser$^{113}$

*FIG. 18*

Framework Sequences of huMAb4D5-8 Light Chain Variable Domain Modified at Positions 66 and 99 (Underlined)

LC-FR1 $^{1}$Asp Ile Gln Met Thr Gln Ser Pro Ser Ser Leu Ser Ala Ser Val Gly Asp Arg Val Thr Ile Thr Cys$^{23}$

LC-FR2 $^{35}$Trp Tyr Gln Gln Lys Pro Gly Lys Ala Pro Lys Leu Leu Ile Tyr$^{49}$

LC-FR3 $^{57}$Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys$^{88}$

LC-FR4 $^{98}$Phe Arg Gln Gly Thr Lys Val Glu Ile Lys$^{107}$

Framework Sequences of huMAb4D5-8 Heavy Chain Variable Domain Modified at Postions 71, 73 and 78 (Underlined)

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$

HC-FR2 $^{36}$Trp Val Arg Gln Ala Pro Gly Lys Gly Leu Glu Trp Val$^{48}$

HC-FR3 $^{66}$Arg Phe Thr Ile Ser Arg Asp Asn Ser Lys Asn Thr Leu Tyr Leu Gln Met Asn83 Ser83a Leu83b Arg83c Ala Glu Asp Thr Ala Val Tyr Tyr Cys$^{92}$

HC-FR4 $^{103}$Trp Gly Gln Gly Thr Leu Val Thr Val Ser Ser$^{113}$

HVR-H1 Sequences - Antibody A and Affinity Matured Antibodies Derived from Antibody A

| | | Kabat Number | | | | | | | | | |
|---|---|---|---|---|---|---|---|---|---|---|---|
| Antibody # | SEQ ID NO: | 26 | 27 | 28 | 29 | 30 | 31 | 32 | 33 | 34 | 35 |
| A, A-1, A-2 | 81 | G | F | T | F | S | N | Y | G | I | H |

HVR-H2 Sequences - Antibody A and Affinity Matured Antibodies Derived from Antibody A

| | | Kabat Number | | | | | | | | | | | | | | | | |
|---|---|---|---|---|---|---|---|---|---|---|---|---|---|---|---|---|---|---|
| Antibody # | SEQ ID NO: | 50 | 51 | 52 | 52A | 53 | 54 | 55 | 56 | 57 | 58 | 59 | 60 | 61 | 62 | 63 | 64 | 65 |
| A, A-1 | 82 | W | I | T | P | D | G | G | Y | T | D | Y | A | D | S | V | K | G |
| A-2 | 83 | W | I | T | G | N | G | G | Y | S | D | Y | A | D | S | V | K | G |
| Consensus | 84 | W | I | T | P/G | D/N | G | G | Y | T/S | D | Y | A | D | S | V | K | G |

HVR-H3 Sequences - Antibody A and Affinity Matured Antibodies Derived from Antibody A

| | | Kabat Number | | | | | | |
|---|---|---|---|---|---|---|---|---|
| Antibody # | SEQ ID NO: | 95 | 96 | 97 | 98 | 100k | 101 | 102 |
| A, A-2 | 85 | A | G | S | W | F | A | Y |
| A-1 | 86 | A | G | S | L | F | A | Y |
| Consensus | 87 | A | G | S | W/L | F | A | Y |

HVR-L1 Sequences - Antibody A and Affinity Matured Antibodies Derived from Antibody A

| | | Kabat Number | | | | | | | | | | |
|---|---|---|---|---|---|---|---|---|---|---|---|---|
| Antibody # | SEQ ID NO: | 24 | 25 | 26 | 27 | 28 | 29 | 30 | 31 | 32 | 33 | 34 |
| A, A-1, A-2 | 88 | R | A | S | Q | D | V | S | T | A | V | A |

HVR-L2 Sequences - Antibody A and Affinity Matured Antibodies Derived from Antibody A

| | | Kabat Number | | | | | | |
|---|---|---|---|---|---|---|---|---|
| Antibody # | SEQ ID NO: | 50 | 51 | 52 | 53 | 54 | 55 | 56 |
| A, A-1, A-2 | 89 | S | A | S | F | L | Y | S |

HVR-L3 Sequences - Antibody A and Affinity Matured Antibodies Derived from Antibody A

| | | Kabat Number | | | | | | | | |
|---|---|---|---|---|---|---|---|---|---|---|
| Clone # | SEQ ID NO: | 89 | 90 | 91 | 92 | 93 | 94 | 95 | 96 | 97 |
| A, A-2 | 90 | Q | Q | S | Y | T | T | P | P | T |
| A-1 | 91 | Q | Q | Y | Y | T | T | A | T | T |
| Consensus | 92 | Q | Q | S/Y | Y | T | T | P/A | P/T | T |

FIG. 21

Framework Sequences of Antibodies A, A-1, A-2 Light Chain Variable Domain

LC-FR1 $^{1}$Asp Ile Gln Met Thr Gln Ser Pro Ser Ser Leu Ser Ala Ser Val Gly Asp Arg Val Thr Ile Thr Cys$^{23}$

LC-FR2 $^{35}$Trp Tyr Gln Gln Lys Pro Gly Lys Ala Pro Lys Leu Leu Ile Tyr$^{49}$

LC-FR3 $^{57}$Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys$^{88}$

LC-FR4 $^{98}$Phe Gly Gln Gly Thr Lys Val Glu Ile Lys Arg$^{108}$

Framework Sequences of Antibodies A, A-1, A-2 Heavy Chain Variable Domain

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$

HC-FR2 $^{36}$Trp Val Arg Gln Ala Pro Gly Lys Gly Leu Glu Trp Val Gly$^{49}$

HC-FR3 $^{66}$Arg Phe Thr Ile Ser Ala Asp Thr Ser Lys Asn Thr Ala Tyr Leu Gln Met Asn Ser Leu Arg Ala Glu Asp Thr Ala Val Tyr Tyr Cys Ala Arg$^{94}$

HC-FR4 $^{103}$Trp Gly Gln Gly Thr Leu Val Thr Val Ser Ser$^{113}$

*FIG. 22*

| Antibody | Light Chain Sequences | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| Anti-Notch2 | | D | I | Q | M | T | Q | S | P | S | S | L | S | A | S | V | G | D | R | V | T | I | T | C |
| Anti-Notch1 | | D | I | Q | M | T | Q | S | P | S | S | L | S | A | S | V | G | D | R | V | T | I | T | C |
| Anti-Notch3 | | D | I | Q | M | T | Q | S | P | S | S | L | S | A | S | V | G | D | R | V | T | I | T | C |
| Anti-Jag1 | | D | I | Q | M | T | Q | S | P | S | S | L | S | A | S | V | G | D | R | V | T | I | T | C |

Kabat - CDR L1

| | 24 | 25 | 26 | 27 | 27A | 27B | 27C | 27D | 27E | 27F | 28 | 29 | 30 | 31 | 32 | 33 | 34 | 35 | 36 | 37 | 38 | 39 | 40 | 41 |
|---|---|---|---|---|---|---|---|---|---|---|---|---|---|---|---|---|---|---|---|---|---|---|---|---|
| Anti-Notch2 | R | A | S | Q | . | . | . | . | . | . | N | I | K | R | F | L | A | W | Y | Q | Q | K | P | G |
| Anti-Notch1 | R | A | S | Q | . | . | . | . | . | . | D | V | S | T | A | V | A | W | Y | Q | Q | K | P | G |
| Anti-Notch3 | R | A | S | Q | . | . | . | . | . | . | G | I | S | Y | V | V | A | W | Y | Q | Q | K | P | G |
| Anti-Jag1 | R | A | S | Q | . | . | . | . | . | . | D | V | S | T | A | V | A | W | Y | Q | Q | K | P | G |

| | 42 | 43 | 44 | 45 | 46 | 47 | 48 | 49 | 50 | 51 | 52 | 53 | 54 | 54A | 54B | 54C | 54D | 54E | 55 | 56 | 57 | 58 | 59 |
|---|---|---|---|---|---|---|---|---|---|---|---|---|---|---|---|---|---|---|---|---|---|---|---|
| | | | | | | | | | | | | | Kabat - CDR L2 | | | | | | | | | | |
| Anti-Notch2 | K | A | P | K | L | L | I | Y | G | A | S | T | R | L | . | . | . | . | E | S | G | V | P |
| Anti-Notch1 | K | A | P | K | L | L | I | Y | S | A | S | F | L | . | . | . | . | . | Y | S | G | V | P |
| Anti-Notch3 | K | A | P | K | L | L | I | Y | D | A | S | S | L | . | . | . | . | . | E | S | G | V | P |
| Anti-Jag1 | K | A | P | K | L | L | I | Y | S | A | S | F | L | . | . | . | . | . | Y | S | G | V | P |

| | 60 | 61 | 62 | 63 | 64 | 65 | 66 | 66A | 66B | 67 | 68 | 69 | 70 | 71 | 72 | 73 | 74 | 75 | 76 | 77 | 78 | 79 | 80 | 81 |
|---|---|---|---|---|---|---|---|---|---|---|---|---|---|---|---|---|---|---|---|---|---|---|---|---|
| Anti-Notch2 | S | R | F | S | G | S | G | . | . | S | G | T | D | F | T | L | T | I | S | S | L | Q | P | E |
| Anti-Notch1 | S | R | F | S | G | S | G | . | . | S | G | T | D | F | T | L | T | I | S | S | L | Q | P | E |
| Anti-Notch3 | S | R | F | S | G | S | G | . | . | S | G | T | D | F | T | L | T | I | S | S | L | Q | P | E |
| Anti-Jag1 | S | R | F | S | G | S | G | . | . | S | G | T | D | F | T | L | T | I | S | S | L | Q | P | E |

| Antibody | Light Chain Sequences | | | | | | | Kabat - CDR L3 | | | | | | | | | | | | | | | | |
|---|---|---|---|---|---|---|---|---|---|---|---|---|---|---|---|---|---|---|---|---|---|---|---|---|
| | 82 | 83 | 84 | 85 | 86 | 87 | 88 | 89 | 90 | 91 | 92 | 93 | 94 | 95 | 95A | 95B | 95C | 95D | 95E | 95F | 96 | 97 | 98 | 99 |
| Anti-Notch2 | D | F | A | T | Y | Y | C | Q | Q | Y | Y | R | S | P | . | . | . | . | . | . | H | T | F | G |
| Anti-Notch1 | D | F | A | T | Y | Y | C | Q | Q | F | Y | T | T | P | . | . | . | . | . | . | S | T | F | G |
| Anti-Notch3 | D | F | A | T | Y | Y | C | Q | Q | W | N | S | Y | P | . | . | . | . | . | . | F | T | F | G |
| Anti-Jag1 | D | F | A | T | Y | Y | C | Q | Q | S | Y | T | T | P | . | . | . | . | . | . | P | T | F | G |

| | 100 | 101 | 102 | 103 | 104 | 105 | 106 | 107 |
|---|---|---|---|---|---|---|---|---|
| Anti-Notch2 | Q | G | T | K | V | E | I | K |
| Anti-Notch1 | Q | G | T | K | V | E | I | K |
| Anti-Notch3 | Q | G | T | K | V | E | I | K |
| Anti-Jag1 | Q | G | T | K | V | E | I | K |

FIG. 23B

| Antibody | Heavy Chain Sequences | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| Anti-Notch2 | | E | V | Q | L | V | E | S | G | G | G | L | V | Q | P | G | G | S | L | R | L | S | C | A |
| Anti-Notch1 | | E | V | Q | L | V | E | S | G | G | G | L | V | Q | P | G | G | S | L | R | L | S | C | A |
| Anti-Notch3 | | E | V | Q | L | V | E | S | G | G | G | L | V | Q | P | G | G | S | L | R | L | S | C | A |
| Anti-Jag1 | | E | V | Q | L | V | E | S | G | G | G | L | V | Q | P | G | G | S | L | R | L | S | C | A |

Kabat - CDR H1 (31–35B)

| Antibody | 24 | 25 | 26 | 27 | 28 | 29 | 30 | 31 | 32 | 33 | 34 | 35 | 35A | 35B | 36 | 37 | 38 | 39 | 41 | 41 | 42 | 43 | 44 |
|---|---|---|---|---|---|---|---|---|---|---|---|---|---|---|---|---|---|---|---|---|---|---|---|
| Anti-Notch2 | A | S | G | Y | S | F | T | S | Y | G | M | S | . | . | W | V | R | Q | A | P | G | K | G |
| Anti-Notch1 | A | S | G | F | T | F | S | S | Y | W | I | H | . | . | W | V | R | Q | A | P | G | K | G |
| Anti-Notch3 | A | S | G | F | T | F | S | N | Y | W | M | S | . | . | W | V | R | Q | A | P | G | K | G |
| Anti-Jag1 | A | S | G | F | T | F | S | N | Y | G | I | H | . | . | W | V | R | Q | A | P | G | K | G |

Kabat - CDR H2 (50–65)

| Antibody | 45 | 46 | 47 | 48 | 49 | 50 | 51 | 52 | 52A | 52B | 52C | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|---|---|---|---|---|---|
| Anti-Notch2 | L | E | W | V | S | Y | I | Y | P | . | . | Y | S | G | A | T | Y | Y | A | D | S | V | K | G |
| Anti-Notch1 | L | E | W | V | A | R | I | N | P | . | . | P | N | R | S | N | Q | Y | A | D | S | V | K | G |
| Anti-Notch3 | L | E | W | V | G | A | I | S | S | . | . | S | G | S | S | T | Y | Y | A | D | S | V | K | G |
| Anti-Jag1 | L | E | W | V | G | W | I | T | G | . | . | N | G | G | Y | S | D | Y | A | D | S | V | K | G |

| Antibody | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 |
|---|---|---|---|---|---|---|---|---|---|---|---|---|---|---|---|---|---|---|---|---|---|---|---|---|
| Anti-Notch2 | R | F | T | I | S | A | D | T | S | K | N | T | A | Y | L | Q | M | N | S | L | R | A | E | D |
| Anti-Notch1 | R | F | T | I | S | A | D | T | S | K | N | T | A | Y | L | Q | M | N | S | L | R | A | E | D |
| Anti-Notch3 | R | F | T | I | S | R | D | N | S | K | N | T | L | Y | L | Q | M | N | S | L | R | A | E | D |
| Anti-Jag1 | R | F | T | I | S | A | D | T | S | K | N | T | A | Y | L | Q | M | N | S | L | R | A | E | D |

FIG. 24A

Kabat - CDR H3

| Antibody | Heavy Chain Sequences | 87 | 88 | 89 | 90 | 91 | 92 | 93 | 94 | 95 | 96 | 97 | 98 | 99 | 100 | 100A | 100B | 100C | 100D | 100E | 100F | 100G | 100H | 100I | 100J |
|---|---|---|---|---|---|---|---|---|---|---|---|---|---|---|---|---|---|---|---|---|---|---|---|---|---|
| Anti-Notch2 | | T | A | V | Y | Y | C | A | R | H | S | G | Y | Y | R | I | S | S | A | . | . | . | . | . | . |
| Anti-Notch1 | | T | A | V | Y | Y | C | A | R | G | S | G | F | R | W | V | . | . | . | . | . | . | . | . | . |
| Anti-Notch3 | | T | A | V | Y | Y | C | A | R | Q | Y | Y | R | D | . | . | . | . | . | . | . | . | . | . | . |
| Anti-Jag1 | | T | A | V | Y | Y | C | A | R | A | G | S | W | . | . | . | . | . | . | . | . | . | . | . | . |

| Antibody | 100K | 100L | 100M | 101 | 102 | 103 | 104 | 105 | 106 | 107 | 108 | 109 | 110 | 111 | 112 | 113 |
|---|---|---|---|---|---|---|---|---|---|---|---|---|---|---|---|---|
| Anti-Notch2 | . | . | M | D | V | W | G | Q | G | T | L | V | T | V | S | S |
| Anti-Notch1 | . | . | M | D | Y | W | G | Q | G | T | L | V | T | V | S | S |
| Anti-Notch3 | . | . | M | D | V | W | G | Q | G | T | L | V | T | V | S | S |
| Anti-Jag1 | . | . | F | A | Y | W | G | Q | G | T | L | V | T | V | S | S |

FIG. 24B

Kabat - CDR H1: Kabat# 31–35; Chothia - CDR H1: Kabat# 26–32; Contact - CDR H1: Kabat# 30–35

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|
| A | E | V | Q | L | V | E | S | G | G | G | L | V | Q | P | G | G | S | L | R | L | S | C | A | A | S | G | F | T | F | S | N | Y | G | I | H | W | V | R | Q | A |
| A-1 | E | V | Q | L | V | E | S | G | G | G | L | V | Q | P | G | G | S | L | R | L | S | C | A | A | S | G | F | T | F | S | N | Y | G | I | H | W | V | R | Q | A |
| A-2 | E | V | Q | L | V | E | S | G | G | G | L | V | Q | P | G | G | S | L | R | L | S | C | A | A | S | G | F | T | F | S | N | Y | G | I | H | W | V | R | Q | A |

Kabat - CDR H2: Kabat# 50–65; Chothia - CDR H2: Kabat# 52–56; Contact - CDR H2: Kabat# 47–58

| Kabat# | 41 | 42 | 43 | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| A | P | G | K | G | L | E | W | V | G | W | I | T | P | . | . | D | G | G | Y | T | D | Y | A | D | S | V | K | G | R | F | T | I | S | A | D | T | S | K | N | T | A |
| A-1 | P | G | K | G | L | E | W | V | G | W | I | T | P | . | . | D | G | G | Y | T | D | Y | A | D | S | V | K | G | R | F | T | I | S | A | D | T | S | K | N | T | A |
| A-2 | P | G | K | G | L | E | W | V | G | W | I | T | G | . | . | N | G | G | Y | S | D | Y | A | D | S | V | K | G | R | F | T | I | S | A | D | T | S | K | N | T | A |

Kabat - CDR H3: Kabat# 95–102; Chothia - CDR H3: Kabat# 95–102; Contact - CDR H3: Kabat# 93–101

| Kabat# | 79 | 80 | 81 | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | H | K | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| A | Y | L | Q | M | N | S | L | R | A | E | D | T | A | V | Y | Y | C | A | R | A | G | S | W | - | - | - | - | - | - | - | - | - | - | F | A | Y | W | G | Q | G | T | L | V | T | V | S | S | SEQ ID NO: 93 |
| A-1 | Y | L | Q | M | N | S | L | R | A | E | D | T | A | V | Y | Y | C | A | R | A | G | S | L | - | - | - | - | - | - | - | - | - | - | F | A | Y | W | G | Q | G | T | L | V | T | V | S | S | SEQ ID NO: 94 |
| A-2 | Y | L | Q | M | N | S | L | R | A | E | D | T | A | V | Y | Y | C | A | R | A | G | S | W | - | - | - | - | - | - | - | - | - | - | F | A | Y | W | G | Q | G | T | L | V | T | V | S | S | SEQ ID NO: 95 |

FIG. 25A

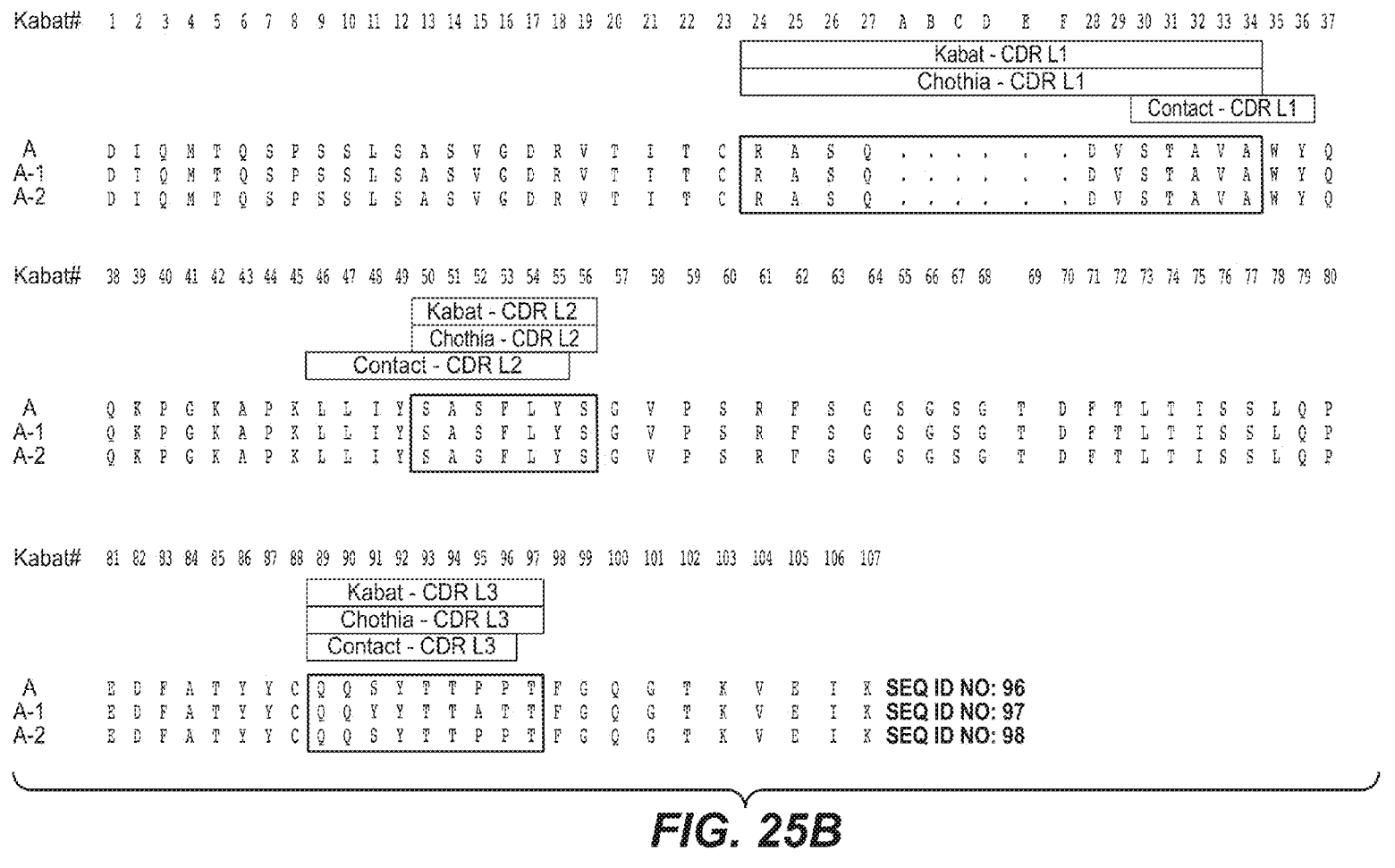

Kabat - CDR L1 (24–34)
Chothia - CDR L1 (24–34)
Contact - CDR L1 (30–36)

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| A | D | I | Q | M | T | Q | S | P | S | S | L | S | A | S | V | G | D | R | V | T | I | T | C | R | A | S | Q | . | . | . | . | . | . | D | V | S | T | A | V | A | W | Y | Q |
| A-1 | D | I | Q | M | T | Q | S | P | S | S | L | S | A | S | V | G | D | R | V | T | I | T | C | R | A | S | Q | . | . | . | . | . | . | D | V | S | T | A | V | A | W | Y | Q |
| A-2 | D | I | Q | M | T | Q | S | P | S | S | L | S | A | S | V | G | D | R | V | T | I | T | C | R | A | S | Q | . | . | . | . | . | . | D | V | S | T | A | V | A | W | Y | Q |

Kabat - CDR L2 (50–56)
Chothia - CDR L2 (50–56)
Contact - CDR L2 (46–55)

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| A | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| A-1 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| A-2 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |

Kabat - CDR L3 (89–97)
Chothia - CDR L3 (89–97)
Contact - CDR L3 (89–96)

| Kabat# | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | |
|---|---|---|---|---|---|---|---|---|---|---|---|---|---|---|---|---|---|---|---|---|---|---|---|---|---|---|---|---|
| A | E | D | F | A | T | Y | Y | C | Q | Q | S | Y | T | T | P | P | T | F | G | Q | G | T | K | V | E | I | K | **SEQ ID NO: 96** |
| A-1 | E | D | F | A | T | Y | Y | C | Q | Q | Y | Y | T | T | A | T | T | F | G | Q | G | T | K | V | E | I | K | **SEQ ID NO: 97** |
| A-2 | E | D | F | A | T | Y | Y | C | Q | Q | S | Y | T | T | P | P | T | F | G | Q | G | T | K | V | E | I | K | **SEQ ID NO: 98** |

*FIG. 25B*

COMPOSITIONS AND METHODS FOR DIAGNOSIS AND TREATMENT OF HEPATIC CANCERS

CROSS REFERENCE TO RELATED APPLICATIONS

This application claims the benefit of U.S. Provisional Application No. 61/789,475, filed Mar. 15, 2013, the disclosure of which is incorporated herein by reference as if set forth in its entirety.

SEQUENCE LISTING

The instant application contains a Sequence Listing which has been submitted electronically in ASCII format and is hereby incorporated by reference in its entirety. Said ASCII copy, created on Mar. 13, 2014, is named P5570R1-US_SL.txt and is 112,305 bytes in size.

FIELD OF THE INVENTION

The present invention relates generally to the field of molecular biology. More specifically, the invention relates to methods of treatment of pathological hepatic conditions, such as cancer.

BACKGROUND

Liver cancer is the fifth most common form of cancer. Each year, approximately 750,000 cases are diagnosed and about 700,000 people die from the disease each year, making it the third most common cause of cancer death in the world (Ferlay et al., Int. J. Cancer 127:2893-2917 (2010)). In the United States, the incidence of primary liver cancer has been rising, and while some progress has been made in detecting and treating localized disease, the five year survival rate for late stage liver cancer is still well below 10% (American-Cancer-Society. 2012. Cancer Facts & Figures. 2012. Atlanta: American Cancer Society).

Established treatments for liver cancer include surgical removal of the part of the liver containing the tumor (partial hepatectomy), liver transplantation, transcatheter arterial chemoembolization (TACE), in situ tumor destruction by various methods such as radiofrequency ablation (RFA) or cryosurgery and administration of Sorafenib. Treatment options for late stage liver patients are limited. Thus, effective treatments of liver cancer remains a significant unmet medical need.

The role of Notch signaling in liver cancer is not well understood. Qi et al. report that Notch1 signaling inhibits growth of human hepatocellular carcinoma cells in vitro and in vivo by inducing cell cycle arrest and apoptosis (Qi et al., Cancer Res. 63:8323 (2003)) and Viatour et al. report that expression of Notch1 intracellular domain decreased proliferation and induced apoptosis in murine and human HCC cells (Viatour et al., J. Exp. Med. 208(10):1963 (2011)). Others report that Notch1 small interfering RNA (siRNA) reduced cell invasion and migration but not viability (Zhou et al. Dig. Dis. Sci.). Yet others report that inhibition of individual Notch pathway family members had no effect. Taken together, the Notch pathway's role in liver cancer was not well understood.

SUMMARY

Use of Notch2 signaling inhibitors for the treatment of patients having or at risk of having proliferative disorders of the liver is provided.

In one aspect, methods of treating a liver cancer in an individual in need thereof are provided, comprising the step of administering to the individual an effective amount of a Notch2 signaling inhibitor. In some embodiments, the liver cancer is hepatocellular carcinoma, hepatoma, cholangiocarcinoma, hepatoblastoma, hepatic carcinoma, hepatic angiosarcoma, or metastatic liver cancer. In some embodiments, the hepatocellular carcinoma comprises progenitor-like or cholangiocarcinoma-like liver tumor. In some embodiments, the liver cancer is a refractory cancer.

In some embodiments, the method further comprises administering at least one additional therapeutic agent. Examples of additional therapeutic agents include, but are not limited to chemotherapeutic agent and an antibody.

In some embodiments, the liver cancer comprises cells that express EpCAM, AFP, Notch2, Jag1, Notch2 and Jag1, nuclear Notch2 ICD, Sox9, CK19, Ras, Prom1, Spp1, FoxM1, Plk1, ccnb1, Aurkb, Wnt2, Axin2, or Glul, or any combination thereof. In specific embodiments, the liver cancer comprises cells that are $AFP^+$ $EpCAM^+$. In some embodiments, the liver cancer comprises cells that are $AFP^+$ $EpCAM^-$, $AFP^+$ $EpCAM^+$ $SPP1^+$, $AFP^-$ $EpCAM^+$, $AFP^-$ $EpCAM^+$ $Notch2^+$, $AFP^+$ $EpCAM^-$ $Notch2^+$, $AFP^+$ $EpCAM^+$ $Sox9^+$ and $AFP^+$ $EpCAM^+$ $Sox9^+$ or $AFP^-$ $EpCAM^+$ $SPP1^+$. Liver cancers that comprise cells with alternative combinations of marker expression are specifically contemplated.

In some embodiments, at least one of EpCAM, AFP, Notch2, Jag1, Sox9, CK19, Ras, Prom1, Spp1, FoxM1, Plk1, ccnb1, Aurkb, Wnt2, Axin2, or Glul protein expression was determined in a sample from the individual using immunohistochemistry (IHC). In some embodiments, expression is nucleic acid expression. In some embodiments, expression is determined by a method selected from the group consisting of RNAseq, microarray analysis, immunohistochemistry, enzyme-linked immunosorbent assay, gene expression profiling, polymerase chain reaction, SAGE, MassARRAY technique, fluorescent in situ hybridization and Western blotting.

In some embodiments, administering the Notch2 signaling inhibitor results in a decrease in the expression in the liver cancer of at least one of EpCAM, AFP, Notch2, Notch2 ICD, Jag1, Prom1, Spp1, FoxM1, Plk1, ccnb1 and Aurkb. In some embodiments, administering the Notch2 signaling inhibitor results in an increase in the expression in the liver cancer of at least one of Wnt2, Axin2 and Glul. In some embodiments, expression is determined by RNAseq, microarray analysis, immunohistochemistry, enzyme-linked immunosorbent assay, and Western blotting.

Any of the antibodies of the above embodiments may be a full-length IgG1 or IgG2a antibody. In some embodiments, the antibody causes cancer cell death, e.g., liver cancer cell death. Any of the antibodies in the above embodiments may be conjugated to a growth inhibitory agent, e.g., a cytotoxic agent. Examples of cytotoxic agent include, but are not limited to, toxins, antibiotics, radioactive isotopes and nucleolytic enzymes. Any of the antibodies in the above embodiments may be produced by known methods in the art, e.g., in bacteria or in CHO cells.

In one aspect, methods are provided for preventing liver cancer in an individual at risk of having liver cancer, comprising the step of administering to the individual an effective amount of a Notch2 signaling inhibitor. In some embodiments, the individual has a liver condition selected from the group consisting of hepatitis B or C, cirrhosis of the liver, non-viral/non-alcoholic steatohepatitis, benign liver tumors, hemangiomas, hepatic adenomas, and focal nodular hyperplasia. In some embodiments, the Notch2 signaling inhibitor is an anti-Jag1 antibody, e.g., an anti-Jag1 antagonist antibody.

In one aspect, methods are provided for inhibiting growth of a cell that expresses secreted phosphoprotein1 (SPP1), comprising contacting the cell with a Notch2 signaling inhibitor, thereby inhibiting growth of the cell. In one embodiment, SPP1 protein comprises the amino acid sequence shown in FIG. 11. In one embodiment, contacting the cell with the Notch2 signaling inhibitor reduces SPP1 expression in the cell. For example, contacting the cell with the Notch2 signaling inhibitor reduces SPP1 expression in the cell by at least about 50%, 60%, 70%, 80%, 90%, or 100%. The expression of SPP1 mRNA or protein can be determined by any method in the art. In some embodiments, the Notch2 signaling inhibitor is an anti-Notch2 antibody, e.g., an anti-Notch2 negative regulatory region (NRR) antibody, such as any anti-Notch2 NRR antibody disclosed herein. In some embodiments, the antibody is an anti-Jag1 antibody, such as any anti-Jag1 antibody disclosed herein. In some embodiments, the cell is a liver cancer cell. In some embodiments, the liver cancer cell expresses EpCAM, AFP, AFP and EpCAM, Notch2, Jag1, Notch2 and Jag1, nuclear Notch2 ICD, Ras, Prom1, Spp1, FoxM1, Plk1, ccnb1, Aurkb, Wnt2, Axin2, or Glul, or any combination thereof. In some embodiments, contacting the cell with the Notch2 signaling inhibitor results in a decrease in the expression in the cell of at least one of EpCAM, AFP, Notch2, Notch2 ICD, Jag1, Prom1, Spp1, FoxM1, Plk1, ccnb1 and Aurkb. In some embodiments, administering the Notch2 signaling inhibitor results in an increase in the expression in the cell of at least one of Wnt2, Axin2 and Glul. In some embodiments, expression is determined by RNAseq, microarray analysis, immunohistochemistry, enzyme-linked immunosorbent assay, and Western blotting.

In one aspect, methods are provided for inhibiting proliferation of a cell that expresses secreted phosphoprotein1 (SPP1), comprising contacting the cell with a Notch2 signaling inhibitor, thereby inhibiting proliferation of the cell.

In one aspect, methods are provided for treating a mammal having a liver cancer comprising cells that express a Spp1 gene encoding a peptide comprising an amino acid sequence having at least about 90%, 91%, 92%, 93%, 94%, 95%, 96%, 97%, 98%, 99%, 100% identity to the polypeptide shown in FIG. 11, comprising administering to the mammal an effective amount of a Notch2 signaling inhibitor, thereby effectively treating the mammal. In some embodiments, the cells express a SPP1 protein comprising an amino acid sequence having at least about 90%, 91%, 92%, 93%, 94%, 95%, 96%, 97%, 98%, 99%, 100% identity to the polypeptide shown in FIG. 11.

In some embodiments, the liver cancer is hepatocellular carcinoma, hepatoma, cholangiocarcinoma, hepatoblastoma, hepatic carcinoma, hepatic angiosarcoma, or metastatic liver cancer. In some embodiments, the liver cancer is a refractory cancer. Any of the antibodies herein may be a full-length IgG1 or IgG2a antibody. In some embodiments, the antibody causes cancer cell death, e.g., liver cell death. Any of the herein may be conjugated to a growth inhibitory agent, e.g., a cytotoxic agent. Examples of cytotoxic agent include, but are not limited to, toxins, antibiotics, radioactive isotopes and nucleolytic enzymes. Any of the antibodies herein may be produced by known methods in the art, e.g., in bacteria or in CHO cells.

In some embodiments, the method further comprises administering at least one additional therapeutic agent. Examples of additional therapeutic agents include, but are not limited to chemotherapeutic agent and an antibody.

In some embodiments, the liver cancer comprises cells that express EpCAM, AFP, AFP and EpCAM, Notch2, Jag1, Notch2 and Jag1, nuclear Notch2 ICD, Ras, Prom1, Spp1, FoxM1, Plk1, ccnb1, Aurkb, Wnt2, Axin2, or Glul, or any combination thereof. In some embodiments, administering the Notch2 signaling inhibitor results in a decrease in the expression in the liver cancer of at least one of EpCAM, AFP, Notch2, Notch2 ICD, Jag1, Prom1, Spp1, FoxM1, Plk1, ccnb1 and Aurkb. In some embodiments, administering the Notch2 signaling inhibitor results in an increase in the expression in the liver cancer of at least one of Wnt2, Axin2 and Glul. In some embodiments, expression is determined by RNAseq, microarray analysis, immunohistochemistry, enzyme-linked immunosorbent assay, and Western blotting.

In one aspect, methods are provided for treating a liver cell proliferative disorder associated with increased expression or activity of a protein having at least 90%, 91%, 92%, 93%, 94%, 95%, 96%, 97%, 98%, 99%, 100% amino acid sequence identity to the polypeptide shown in FIG. 8C, comprising administering to an individual in need of such treatment an effective amount of an anti-Jag1 antagonist antibody, thereby effectively treating the liver cell proliferative disorder. In some embodiments, the cell proliferative disorder is a cancer, such as liver cancer. In some embodiments the individual has a liver condition selected from the group consisting of hepatitis B or C, cirrhosis of the liver, benign liver tumors, hemangiomas, hepatic adenomas, and focal nodular hyperplasia.

In certain embodiments, the anti-Jag1 antibody is any of the anti-Jag1 antibodies described herein. In certain embodiments, the anti-Jag1 antibody is a human, humanized, or chimeric antibody. In certain embodiments, any of the antibodies of the above embodiments is an antibody fragment.

In one aspect, methods are provided for treating a liver cell proliferative disorder associated with increased expression or activity of a protein having at least 90% amino acid sequence identity to the polypeptide shown in FIG. 11, comprising administering to an individual in need of such treatment an effective amount of an anti-Jag1 antagonist antibody, thereby effectively treating the liver cell proliferative disorder. In some embodiments, the cell proliferative disorder is a cancer, such as liver cancer. In some embodiments the individual has a liver condition selected from the group consisting of hepatitis B or C, cirrhosis of the liver, benign liver tumors, hemangiomas, hepatic adenomas, and focal nodular hyperplasia.

In one aspect, methods are provided for reducing serum SPP1 protein levels in an individual, the method comprising administering to the individual an effective amount of a Notch2 signaling inhibitor thereby reducing serum SPP1 levels in the individual. In one embodiment, the individual has a liver cancer. In one embodiment, the serum SPP1 protein levels prior to administering the Notch2 signaling inhibitor to the individual are at least about 80 ng/ml. In certain embodiments, the serum SPP1 protein levels prior to administering the Notch2 signaling inhibitor to the individual are between about 80 ng/ml and about 500 ng/ml, between about 86 ng/ml and about 250 ng/ml, between about 120 ng/ml and about 170 ng/ml, or about 165 ng/ml. In some embodiments, administering the Notch2 signaling inhibitor to the individual results in serum SPP1 protein levels of less than 80 ng/ml. In specific embodiments, serum SPP1 protein levels prior to administering the Notch2 signaling inhibitor are 24 hours prior to administering the Notch2 signaling inhibitor. Serum SPP1 protein levels prior to or following administration of the Notch2 signaling inhibitor may be determined by any appropriate method, such as enzyme-linked immunosorbent assay. In specific embodiments, serum SPP1 protein levels are reduced about one, two, three, six or 12 month after administering the Notch2 signaling inhibitor. In some embodiments, the liver cancer is hepatocellular carcinoma, hepatoma, cholangiocarcinoma, hepatoblastoma, hepatic carcinoma, hepatic angiosarcoma or metastatic liver cancer. In some embodiments, the Notch2 signaling inhibitor is an siRNA, small-molecule inhibitor or antibody. In some embodiments, the antibody is an antagonist antibody.

In certain embodiments, any of the antibodies of the above embodiments is a monoclonal antibody. In certain embodiments, any of the antibodies of the above embodiments is a human, humanized, or chimeric antibody. In certain embodiments, any of the antibodies of the above embodiments is an antibody fragment.

In some embodiments, the method further comprises administering at least one additional therapeutic agent. Examples of additional therapeutic agents include, but are not limited to chemotherapeutic agent and an antibody. In some embodiments, Sorafenib is an additional therapeutic agent.

In some embodiments, the liver cancer comprises cells that express EpCAM, AFP, AFP and EpCAM, Notch2, Jag1, Notch2 and Jag1, nuclear Notch2 ICD, Ras, Prom1, Spp1, FoxM1, Plk1, ccnb1, Aurkb, Wnt2, Axin2, or Glul, or any combination thereof. In some embodiments, Ras is a mutant Ras. In some embodiments, administering the Notch2 signaling inhibitor results in a decrease in the expression in the liver cancer of at least one of EpCAM, AFP, Notch2, Notch2 ICD, Jag1, Prom1, Spp1, FoxM1, Plk1, ccnb1 and Aurkb. In some embodiments, administering the Notch2 signaling inhibitor results in an increase in the expression in the liver cancer of at least one of Wnt2, Axin2 and Glul. In some embodiments, expression is determined by RNAseq, microarray analysis, immunohistochemistry, enzyme-linked immunosorbent assay, and Western blotting.

In one aspect, methods are provided for treating a liver tumor in a mammal, wherein the growth of the liver tumor is at least in part dependent upon a growth potentiating effect of Notch2 signaling, comprising contacting the tumor with an antibody that binds to Notch2 or Jag1. In one embodiment, binding of the antibody to the tumor antagonizes the growth-potentiating activity of Notch2. In some embodiments, the mammal is a human.

In one aspect, methods are provided for treating of liver cancer comprising administering to an individual who has elevated serum SPP1 protein levels an effective amount of a Notch2 signaling inhibitor. In one embodiment, the serum SPP1 protein levels of the individual are at least about 80 ng/ml. In certain embodiments, the serum SPP1 protein levels prior to administering the Notch2 signaling inhibitor to the individual are between about 80 ng/ml and about 500 ng/ml, between about 86 ng/ml and about 250 ng/ml, between about 120 ng/ml and about 170 ng/ml, or about 165 ng/ml. In some embodiments, administering the Notch2 signaling inhibitor to the individual results in serum SPP1 protein levels of less than 80 ng/ml. In specific embodiments, serum SPP1 protein levels prior to administering the Notch2 signaling inhibitor are 24 hours prior to administering the Notch2 signaling inhibitor. Serum SPP1 protein levels prior to or following administration of the Notch2 signaling inhibitor may be determined by any appropriate method, such as enzyme-linked immunosorbent assay. In specific embodiments, serum SPP1 protein levels are reduced in the individual about one, two, three, six or 12 month after administering the Notch2 signaling inhibitor. In some embodiments, the liver cancer is hepatocellular carcinoma, hepatoma, cholangiocarcinoma, hepatoblastoma, hepatic carcinoma, hepatic angiosarcoma or metastatic liver cancer. In some embodiments, the Notch2 signaling inhibitor is an siRNA, small-molecule inhibitor or antibody. In some embodiments, the antibody is an antagonist antibody, such as an anti-Notch2 antagonist antibody or an anti-Jag1 antagonist antibody.

In some aspects, methods are provided for treating an individual having a liver cancer, comprising the steps of administering to the individual a Notch2 signaling inhibitor; and determining Notch2 signaling, wherein a decrease in Notch2 signaling following treatment, compared to Notch2 signaling prior to treatment, is indicative of reduction of liver cancer in the individual. In some embodiments, Notch2 signaling is determined by measuring Notch2 ICD nuclear localization, e.g., by immunohistochemical analysis of a liver cancer sample from the individual. In some embodiments, Notch2 signaling is determined by measuring expression of a gene selected from the group consisting of Notch2, Jag1, Hes and Hey1. Expression can be determined by any method, e.g., RT-PCR, microarray, and RNAseq analysis. In some embodiments, the liver cancer is hepatocellular carcinoma, hepatoma, cholangiocarcinoma, hepatoblastoma, hepatic carcinoma, hepatic angiosarcoma, and metastatic liver cancer. In some embodiments, the Notch2 signaling inhibitor is an siRNA, small-molecule inhibitor or antibody. In some embodiments, the antibody is an antagonist antibody, such as an anti-Notch2 antagonist antibody or an anti-Jag1 antagonist antibody.

In some aspects, methods for inhibiting cellular proliferation comprising treating mammalian liver cancer cells with an antibody to Notch2 or Jag1, whereby proliferation of the liver cancer cell is inhibited. In certain embodiments, the cell is in a patient. In certain embodiments, the cell is in a culture medium. In certain embodiments, the cell is a liver cancer cell. In certain embodiments, the antibody is an anti-Notch2 or anti-Jag1 antagonist antibody is as described herein. In certain embodiments, the antibody is a human, humanized, or chimeric antibody. In certain embodiments, any of the antibodies of the above embodiments is an antibody fragment.

In any of the methods herein, Notch2 signaling inhibitors may be the following inhibitors. In some embodiments, the Notch2 signaling inhibitor is a siRNA, small-molecule inhibitor or antibody. In some embodiments, the antibody is an antagonist antibody. In some embodiments, the antibody is an anti-Notch2 antibody, e.g., an anti-Notch2 negative regulatory region (NRR) antibody. In some embodiments, the antibody does not significantly bind to a Notch family member other than Notch2. In some embodiments, the antibody binds to mouse Notch2 NRR and human Notch2 NRR, e.g., with a Kd of ≤10 nM. In some embodiments, the antibody comprises:

(a) an HVR-H1 comprising the amino acid sequence of SEQ ID NO:1;
(b) an HVR-H2 comprising the amino acid sequence of SEQ ID NO:3;
(c) an HVR-H3 comprising the amino acid sequence of SEQ ID NO:4;
(d) an HVR-L1 comprising an amino acid sequence that conforms to the consensus sequence of SEQ ID NO:9;

(e) an HVR-L2 comprising an amino acid sequence that conforms to the consensus sequence of SEQ ID NO:14; and (f) an HVR-L3 comprising an amino acid sequence that conforms to the consensus sequence of SEQ ID NO:19.

In further embodiments, the antibody is an anti-Jag1 antibody. In some embodiments, the antibody comprises at least one, two, three, four, five, or six HVRs selected from: (a) HVR-H1 comprising the amino acid sequence of SEQ ID NO:81; (b) HVR-H2 comprising an amino acid sequence of SEQ ID NO:84; (c) HVR-H3 comprising an amino acid sequence of SEQ ID NO:87; (d) HVR-L1 comprising the amino acid sequence of SEQ ID NO:88; (e) HVR-L2 comprising the amino acid sequence of SEQ ID NO:89; and (f) HVR-L3 comprising an amino acid sequence of SEQ ID NO:92. In one embodiment, the antibody comprises: (a) an HVR-H1 comprising the amino acid sequence of SEQ ID NO:81; (b) an HVR-H2 comprising the amino acid sequence of SEQ ID NO:82; (c) an HVR-H3 comprising the amino acid sequence of SEQ ID NO:85; (d) an HVR-L1 comprising the amino acid sequence of SEQ ID NO:88; (e) an HVR-L2 comprising the amino acid sequence of SEQ ID NO:89; and (f) an HVR-L3 comprising the amino acid sequence of SEQ ID NO:90.

In one embodiment, the antibody comprises: (a) an HVR-H1 comprising the amino acid sequence of SEQ ID NO:81; (b) an HVR-H2 comprising the amino acid sequence of SEQ ID NO:82; (c) an HVR-H3 comprising the amino acid sequence of SEQ ID NO:86; (d) an HVR-L1 comprising the amino acid sequence of SEQ ID NO:88; (e) an HVR-L2 comprising the amino acid sequence of SEQ ID NO:89; and (f) an HVR-L3 comprising the amino acid sequence of SEQ ID NO:91. In one embodiment, the antibody comprises: (a) an HVR-H1 comprising the amino acid sequence of SEQ ID NO:81; (b) an HVR-H2 comprising the amino acid sequence of SEQ ID NO:83; (c) an HVR-H3 comprising the amino acid sequence of SEQ ID NO:85; (d) an HVR-L1 comprising the amino acid sequence of SEQ ID NO:88; (e) an HVR-L2 comprising the amino acid sequence of SEQ ID NO:89; and (f) an HVR-L3 comprising the amino acid sequence of SEQ ID NO:90.

In certain embodiments, any of the antibodies of the embodiments herein is a monoclonal antibody. In certain embodiments, any of the antibodies of the above embodiments is a human, humanized, or chimeric antibody. In certain embodiments, any of the antibodies of the above embodiments is an antibody fragment.

In a further embodiment, any antibody of the embodiments herein further comprises light chain variable domain framework LC-FR1, LC-FR2, LC-FR3, and LC-FR4 comprising, in order, the amino acid sequence of huMAb4D5-8 light chain variable domain framework LC-FR1, LC-FR2, LC-FR3, and LC-FR4 of FIG. 18.

In a further embodiment, any antibody of the embodiments herein further comprises a heavy chain variable domain framework HC-FR1, HC-FR2, HC-FR3, and HC-FR4 comprising, in order, the amino acid sequence of huMAb4D5-8 heavy chain variable domain framework HC-FR1, HC-FR2, HC-FR3, and HC-FR4 of FIG. 18.

In a further embodiment, any antibody of the embodiments herein further comprises a light chain variable domain framework LC-FR1, LC-FR2, LC-FR3, and LC-FR4 comprising, in order, the amino acid sequence of huMAb4D5-8 light chain variable domain framework LC-FR1, LC-FR2, LC-FR3, and LC-FR4 of FIG. 19.

In a further embodiment, any antibody of the embodiments herein further comprises a heavy chain variable domain framework HC-FR1, HC-FR2, HC-FR3, and HC-FR4 comprising, in order, the amino acid sequence of huMAb4D5-8 heavy chain variable domain framework HC-FR1, HC-FR2, HC-FR3, and HC-FR4 of FIG. 19.

In certain embodiments, the antibody is an isolated antibody that binds to Jag1, comprising (a) a VH sequence having at least 95% sequence identity to the amino acid sequence of SEQ ID NO:94; (b) a VL sequence having at least 95% sequence identity to the amino acid sequence of SEQ ID NO:97; or (c) a VH sequence as in (a) and a VL sequence as in (b). In some embodiments, the antibody comprises a VH sequence of SEQ ID NO:94. In some embodiments, the antibody comprises a VL sequence of SEQ ID NO:97. In some embodiments, the antibody comprises a VH sequence of SEQ ID NO:94 and a VL sequence of SEQ ID NO:97. In some embodiments, the antibody comprises (a) a VH sequence having at least 95% sequence identity to the amino acid sequence of SEQ ID NO:95; (b) a VL sequence having at least 95% sequence identity to the amino acid sequence of SEQ ID NO:98; or (c) a VH sequence as in (a) and a VL sequence as in (b). In some embodiments, the antibody comprises a VH sequence of SEQ ID NO:95. In some embodiments, the antibody comprises a VL sequence of SEQ ID NO:98. In some embodiments, the antibody comprises a VH sequence of SEQ ID NO:95 and a VL sequence of SEQ ID NO:98.

In certain embodiments, the antibody is an isolated antibody that binds to Jag1, comprising (a) a VH sequence having at least 95% sequence identity to the amino acid sequence of SEQ ID NO:93; (b) a VL sequence having at least 95% sequence identity to the amino acid sequence of SEQ ID NO:96; or (c) a VH sequence as in (a) and a VL sequence as in (b). In some embodiments, the antibody comprises a VH sequence of SEQ ID NO:93. In some embodiments, the antibody comprises a VL sequence of SEQ ID NO:96. In some embodiments, the antibody comprises a VH sequence of SEQ ID NO:93 and a VL sequence of SEQ ID NO:96.

In one aspect, an article of manufacture is provided comprising (a) a container; (b) a composition of matter contained within the container comprising an anti-Notch2 antibody or an anti-Jagged1 antibody and a carrier for the treatment of liver cancer; and (c) a label affixed to the container, or a package insert included with the container, referring to the use of the composition of matter for the therapeutic treatment of or the diagnostic detection of a liver cancer.

In one aspect, an anti-Notch2 antibody for use in the treatment of a liver cancer is provided. In certain embodiments, the liver cancer is hepatocellular carcinoma. In certain embodiments, the antibody is an anti-Notch2 NRR antagonist antibody. In one aspect, an anti-Jag1 antibody for use in the treatment of a liver cancer is provided. In certain embodiments, the liver cancer is hepatocellular carcinoma. In certain embodiments, the antibody is an anti-Jag1 antagonist antibody.

In one aspect, use of an anti-Notch2 antibody in the preparation of a medicament for the therapeutic treatment of a liver cancer is provided. In one aspect, use of an anti-Jagged1 antibody in the preparation of a medicament for the therapeutic treatment of a liver cancer is provided.

In one aspect, use of an article of manufacture described herein in the preparation of a medicament for the therapeutic treatment of a liver cancer is provided. In one aspect, use of an article of manufacture as described herein in the preparation of a medicament for treatment or prevention of a liver cell proliferative disorder is provided.

BRIEF DESCRIPTION OF THE FIGURES

FIGS. 1A-C depict immunohistochemical staining of tumors that are $AFP^+EpCAM^-$ (FIG. 1A), $AFP^+EpCAM^+$ (FIG. 1B) and $AFP^-EpCAM^+$ (FIG. 1C). FIG. 1D depicts the prevalence of marker expression, expressed in percentage of total cells. FIG. 1F depicts immunohistochemical staining of activation of Notch2 signaling indicated by localization of the Notch2 protein in the nucleus. FIG. 1E depicts the percent cells with nuclear Notch2 staining.

FIG. 2A depicts isolated livers from HTV mice treated with an isotype control antibody (upper left), an anti-Notch2 antibody (upper right) or an anti-Jag1 antibody (lower left) beginning on the day of the HTV. FIG. 2B depicts Ras/AKT HTV mice liver weight following antibody treatment administered at the time of HTV injection, expressed in percent body weight. FIG. 2C depicts Ras/AKT HTV mice liver weight following antibody treatment administered two weeks after HTV injection, expressed in percent body weight ($p<0.05$, $n>8$). FIG. 2D depicts Ras/AKT HTV mice liver weight following antibody treatment ($p<0.02$, $n>6$).

FIG. 3A depicts immunofluorescence analysis of AFP and EpCAM expression in livers of AKT/Ras HTV mice treated with anti-Notch2, anti-Jag1 or isotype control antibody. FIGS. 3B and C depict a decrease in $EpCAM^+$ (FIG. 3B; $p<0.007$, $n\geq7$) and $AFP^+$ (FIG. 3C; $p<0.03$, $n\geq7$) area following anti-Notch2 and anti-Jag1 treatment. FIG. 3D depicts immunofluorescence analysis of AFP and EpCAM expression in livers of AKT/Ras HTV mice treated with anti-Notch1 antibody. FIG. 3E depicts the percentage of EpCAM cells following AKT/Ras HTV mice treatment with an anti-Notch1, anti-Notch2, anti-Notch3, anti-Jag1 or isotype control antibody. FIG. 3F depicts relative expression of Cytokeratin 19 (CK19) following AKT/Ras HTV mice treatment with an anti-Notch1, anti-Notch2, anti-Notch3, anti-Jag1 or isotype control antibody. FIG. 3G depicts RNA and FIG. 3H depicts protein levels of Sox9 following AKT/Ras HTV mice treatment with an anti-Notch1, anti-Notch2, anti-Notch3, anti-Jag1 or isotype control antibody.

FIG. 4A depicts Notch2 nuclear immunohistochemical staining expressed in number of cells. FIG. 4B depicts relative expression of Notch2, determined by QRTPCR. FIG. 4C depicts immunohistochemical staining for Hes1 in AKT/Ras HTV tumor-bearing livers. FIG. 4D depicts the fraction of $Hes1^+$ cells, determined by immunohistochemistry. FIG. 4E depicts relative expression of HeyL, determined by QRTPCR.

FIGS. 7A-B illustrate expression of Notch2 in human HCC. FIG. 7A depicts Notch1, Notch2 and Notch3 expression, determined by RT-PCR, in cultured human HCC cell lines. FIG. 7B depicts immunohistochemical staining of human HCC tumors for Notch2, Jag1 and Hes1.

FIGS. 8A-D show exemplary amino acid sequences of human (C) and murine (D) Notch2 protein and human (A) and murine (B) Notch2 negative regulatory region (NRR).

FIG. 9 shows exemplary amino acid sequences of human and murine Jagged 1 protein.

FIGS. 10A-B show the amino acid sequences of peptides used for phage antibody library screening and selection. All proteins were expressed as a secreted protein in BEVS cells and their sequences are listed in the N-terminal to C-terminal direction. FIG. 10A shows the amino acid sequence of expressed protein murine Jagged 1-DSL-EGF1-4 (Q34-D377). The bold font at the N-terminus represents a short linker sequence (ADLGS (SEQ ID NO: 2)). The bold font at the C-terminus represents a short linker sequence (EFG), a thrombin cleavage site (LVPRGS (SEQ ID NO: 26)), a G spacer and the 6-His tag (SEQ ID NO: 27). FIG. 10B shows the amino acid sequence of expressed protein human Jag1-DSL-EGF1-4. Only the Jag1 sequence is shown although the antigen also contained a TEV protease cleavage site and 6-His tag (SEQ ID NO: 27) at the C-terminus.

FIG. 11 shows an exemplary amino acid sequences of human secreted phosphoprotein1 (SPP1).

FIG. 12 shows the H1, H2, and H3 heavy chain hypervariable region (HVR) sequences of anti-Notch2 NRR antagonist antibodies. Amino acid positions are numbered according to the Kabat numbering system as described below.

FIG. 13 shows the L1, L2, and L3 light chain HVR sequences of anti-Notch2 NRR antagonist antibodies. Amino acid positions are numbered according to the Kabat numbering system as described below.

FIGS. 14A-B show an alignment of the amino acid sequences for the heavy chain variable domains of anti-Notch2 antibodies. Amino acid positions of the complementarity determining regions (CDRs) are indicated.

FIGS. 15A-B show an alignment of the amino acid sequences for the light chain variable domains of anti-Notch2 antibodies. Amino acid positions of the complementarity determining regions (CDRs) are indicated.

FIGS. 16A-B show exemplary acceptor human variable heavy (VH) consensus framework sequences for use in practicing the instant invention. Sequence identifiers are as follows:

Figure 1A:
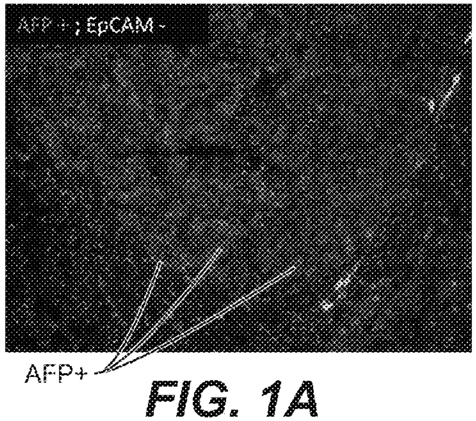
FIGS. 1A-F illustrate characterization of liver cancer marker expression in the AKT/Ras HTV liver cancer model.

- human VH subgroup I consensus framework "A" minus Kabat CDRs (SEQ ID NOs:32, 33, 34, 35).
- human VH subgroup I consensus frameworks "B," "C," and "D" minus extended hypervariable regions (SEQ ID NOs:36, 37, 34, 35; SEQ ID NOs:36, 37, 38, 35; and SEQ ID NOs:36, 37, 39, 35).
- human VH subgroup II consensus framework "A" minus Kabat CDRs (SEQ ID NOs:40, 41, 42, 35).
- human VH subgroup II consensus frameworks "B," "C," and "D" minus extended hypervariable regions (SEQ ID NOs:43, 44, 42, 35; SEQ ID NOs:43, 44, 45, 35; and SEQ ID NOs:43, 44, 46, and 35).

human VH subgroup III consensus framework "A" minus Kabat CDRs (SEQ ID NOs:47, 48, 49, 35).

human VH subgroup III consensus frameworks "B," "C," and "D" minus extended hypervariable regions (SEQ ID NOs:50, 51, 49, 35; SEQ ID NOs:50, 51, 52, 35; and SEQ ID NOs:50, 51, 53, 35).

human VH acceptor framework "A" minus Kabat CDRs (SEQ ID NOs:54, 48, 55, 35).

human VH acceptor frameworks "B" and "C" minus extended hypervariable regions (SEQ ID NOs:50, 51, 55, 35; and SEQ ID NOs:50, 51, 56, 35).

human VH acceptor 2 framework "A" minus Kabat CDRs (SEQ ID NOs:54, 48, 57, 35).

human VH acceptor 2 framework "B," "C," and "D" minus extended hypervariable regions (SEQ ID NOs: 50, 51, 57, 35; SEQ ID NOs:50, 51, 58, 35; and SEQ ID NOs:50, 51, 59, 35).

FIG. 17 shows exemplary acceptor human variable light (VL) consensus framework sequences for use in practicing the instant invention. Sequence identifiers are as follows:

human VL kappa subgroup I consensus framework (κv1): SEQ ID NOs:60, 61, 62, 63 human VL kappa subgroup II consensus framework (κv2): SEQ ID NOs:64, 65, 66, 63 human VL kappa subgroup III consensus framework (κv3): SEQ ID NOs:67, 68, 69, 63 human VL kappa subgroup IV consensus framework (κv4): SEQ ID NOs:70, 71, 72, 63.

FIG. 18 depicts framework region sequences of huMAb4D5-8 light and heavy chains (SEQ ID NOS 60, 61, 30, 63, 50, 51, 59 and 35, respectively, in order of appearance). Numbers in superscript indicate amino acid positions according to Kabat.

FIG. 19 depicts modified/variant framework region sequences of huMAb4D5-8 light and heavy chains (SEQ ID NOS 60, 61, 62, 31, 50, 51, 53 and 35, respectively, in order of appearance). Numbers in superscript indicate amino acid positions according to Kabat.

FIG. 20 shows the H1, H2, and H3 heavy chain hypervariable region (HVR) sequences of anti-Jagged antibodies, as described in the Example s. Amino acid positions are numbered according to the Kabat numbering system as described below.

FIG. 21 shows the L1, L2, and L3 light chain HVR sequences of anti-Jagged antibodies, as described in the Examples. Amino acid positions are numbered according to the Kabat numbering system as described below.

FIG. 22 shows light and heavy chain variable domain framework sequences of anti-Jagged antibodies (SEQ ID NOS 60, 61, 62, 77, 50, 99, 57 and 35, respectively, in order of appearance). Numbers in superscript indicate amino acid positions according to Kabat.

FIGS. 23A-B show an alignment of the amino acid sequences for the heavy chain variable domains of antibodies to Notch2 (SEQ ID NO: 100) (B?), Notch1 (SEQ ID NO: 101) (Y), Notch3 (SEQ ID NO: 102) (W) and Jag1 (SEQ ID NO: 103) (A-2) described in the Examples.

FIGS. 24A-B show an alignment of the amino acid sequences for the light chain variable domains of antibodies to Notch2 (SEQ ID NO: 104), Notch1 (SEQ ID NO: 105), Notch3 (SEQ ID NO: 106) and Jag1 (SEQ ID NO: 107) used in the Examples.

FIGS. 25A-B show an alignment of the amino acid sequences for the heavy (FIG. 25A) and light (FIG. 25B) chain variable domains of anti-Jag1 antibodies. Amino acid positions of the complementarity determining regions (CDRs) are indicated.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-Jag1 antibody" and "an antibody that binds to Jag1" refer to an antibody that is capable of binding Jag1 with sufficient affinity such that the antibody is useful as a diagnostic and/or therapeutic agent in targeting Jag1. In one embodiment, the extent of binding of an anti Jag1 antibody to an unrelated, non-Jag1 protein is less than about 10% of the binding of the antibody to Jag1 as measured, e.g., by a radioimmunoassay (RIA). In certain embodiments, an antibody that binds to Jag1 has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-Jag1 antibody binds to an epitope of Jag1 that is conserved among Jag1 from different species.

An "anti-Jag1 antagonist antibody" is an anti-Jag1 antibody that effects decreased Jag1-mediated signaling, e.g., Jag1-mediated Notch2 signaling.

The terms "anti-Notch2 antibody" and "an antibody that binds to Notch2" refer to an antibody that is capable of binding Notch2 with sufficient affinity such that the antibody is useful as a diagnostic and/or therapeutic agent in targeting Notch2. In one embodiment, the extent of binding of an anti-Notch2 antibody to an unrelated, non-Notch2 protein is less than about 10% of the binding of the antibody to Notch2 as measured, e.g., by a radioimmunoassay (RIA). In certain embodiments, an antibody that binds to Notch2 has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In certain embodiments, an anti-Notch2 antibody binds to an epitope of Notch2 that is conserved among Notch2 from different species.

An "anti-Notch2 antagonist antibody" is an anti-Notch2 antibody (including an anti-Notch2 NRR antibody) that effects decreased Notch2 signaling, as defined below.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

A "blocking" antibody or an "antagonist" antibody is one which significantly inhibits (either partially or completely) a biological activity of the antigen it binds.

The term "chimeric" antibody refers to an antibody in which a portion of the heavy and/or light chain is derived from a particular source or species, while the remainder of the heavy and/or light chain is derived from a different source or species.

The terms "cancer" and "cancerous" refer to or describe the physiological condition in mammals that is typically characterized by unregulated cell growth/proliferation. Examples of liver cancer include, but are not limited to, hepatocellular carcinoma, hepatoma, hepatoblastoma, cholangiocarcinoma, hepatoblastoma, hepatic carcinoma, sarcoma, lymphoma and hepatic angiosarcoma. Liver cancer also includes cancer that originated in the liver and has metastasized to another part of the body.

The terms "cell proliferative disorder" and "proliferative disorder" refer to disorders that are associated with some degree of abnormal cell proliferation. In one embodiment, the cell proliferative disorder is cancer.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omegaI1 (see, e.g., Nicolaou et al., *Angew. Chem. Intl. Ed. Engl.,* 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINEϕ, FILDESINϕ); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chlorambucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (Sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

The term "cytotoxic agent" as used herein refers to a substance that inhibits or prevents a cellular function and/or causes cell death or destruction. Cytotoxic agents include, but are not limited to radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "cytostatic agent" refers to a compound or composition which arrests growth of a cell either in vitro or in vivo. Thus, a cytostatic agent may be one which significantly reduces the percentage of cells in S phase. Further examples of cytostatic agents include agents that block cell cycle progression by inducing G0/G1 arrest or M-phase arrest. The humanized anti-Her2 antibody trastuzumab (HERCEPTIN®) is an example of a cytostatic agent that induces G0/G1 arrest. Classical M-phase blockers include the vincas (vincristine and vinblastine), taxanes, and topoisomerase II inhibitors such as doxorubicin, epirubicin, daunorubicin, etoposide, and bleomycin. Certain agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "expression" refers to conversion of the information encoded in a gene into messenger RNA (mRNA), and then to the protein.

Herein, a sample or cell that "expresses" a protein of interest is one in which mRNA encoding the protein, or the protein, including fragments thereof, is determined to be present in the sample or cell.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH(H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

In one embodiment, HVR residues comprise those identified in FIGS. 12, 13, 20 and 21.

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "individual at risk of having liver cancer" refers to an individual having a higher than average propensity of acquiring liver cancer. Examples of individuals at risk of having liver cancer include, without limitation, individuals having hepatitis, e.g., hepatitis B or C, cirrhosis of the liver, benign liver tumors, hemangiomas, hepatic adenomas, and focal nodular hyperplasias.

The term "inhibit" means to decrease or reduce an activityu, function, and/or amount as compared to a reference.

"Inhibiting cell growth or proliferation" means decreasing a cell's growth or proliferation by at least 10%, 20%, 30%, 40%, 50%, 60%, 70%, 80%, 90%, 95%, or 100%, and includes inducing cell death.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-Jag1 antibody" or "isolated nucleic acid encoding an anti-Notch2 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "Jagged" or "Jag," as used herein, refers to any native Jagged from any vertebrate source, including mammals such as primates (e.g. humans) and rodents (e.g., mice and rats), unless otherwise indicated. The term encompasses "full-length," unprocessed Jag as well as any form of Jagged that results from processing in the cell. The term also encompasses naturally occurring variants of Jagged, e.g., splice variants or allelic variants.

The term "Jagged1" or "Jag1," as used herein, refers to any native Jag1 from any vertebrate source, including mammals such as primates (e.g. humans) and rodents (e.g., mice and rats), unless otherwise indicated. The term encompasses "full-length," unprocessed Jag1 as well as any form of Jag1 that results from processing in the cell. The term also encompasses naturally occurring variants of Jag1, e.g., splice variants or allelic variants. The amino acid sequence of an exemplary human and murine Jag1 is shown in FIG. 9.

The term "level of expression" or "expression level" as used herein, refers to the amount of a polynucleotide, mRNA, or an amino acid product or protein in a biological sample.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "Notch," as used herein, refers to any native Notch from any vertebrate source, including mammals such as primates (e.g. humans) and rodents (e.g., mice and rats), unless otherwise indicated. The term encompasses "full-length," unprocessed Notch as well as any form of Notch that results from processing in the cell. The term also encompasses naturally occurring variants of Notch, e.g., splice variants or allelic variants.

The term "Notch2," as used herein, refers to any native Notch2 from any vertebrate source, including mammals such as primates (e.g. humans) and rodents (e.g., mice and rats), unless otherwise indicated. The term encompasses "full-length," unprocessed Notch2 as well as any form of Notch2 that results from processing in the cell. The term also encompasses naturally occurring variants of Notch2, e.g., splice variants or allelic variants. The amino acid sequence of an exemplary human Notch2 is shown in FIG. 8.

The term "Notch2 signaling inhibitor" refers to an agent that effects decreased Notch2 signaling, as defined above. Notch2 signaling inhibitors include Notch2-specific antagonists and Jag1-specific antagonists. A Notch2-specific antagonist decreases Notch2 signaling and does not significantly affect signaling by another Notch receptor (Notch1, 3, or 4 in mammals) Examples of Notch2-specific antagonist include agents that block Notch2 binding to a Notch2 ligand. A Jag1-specific antagonist decreases Jag1-mediated signaling. Examples of Jag1-specific antagonists include agents that bind Notch2. Pan-Notch inhibitors, such as gamma secretase inhibitors, are explicitly excluded from Notch2 signaling inhibitors defined herein.

The term "package insert" is used to refer to instructions customarily included in Field Code Changed commercial packages of therapeutic products, that contain information about the indications, usage, dosage, administration, combination therapy, contraindications and/or warnings concerning the use of such therapeutic products.

"percent (%) amino acid sequence identity" with respect to a reference polypeptide Field Code Changed sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction *X/Y* where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

"Relapsed" refers to the regression of the patient's illness back to its former diseased state, especially the return of symptoms following an apparent recovery or partial recovery. Unless otherwise indicted, relapsed state refers to the process of returning to or the return to illness before the previous treatment including, but not limited to, chemotherapies and stem cell transplantation treatments.

"Refractory" refers to the resistance or non-responsiveness of a disease or condition to a treatment (e.g., the number of neoplastic plasma cells increases even though treatment if given). Unless otherwise indicated, the term "refractory" refers a resistance or non-responsiveness to any previous treatment including, but not limited to, chemotherapies and stem cell transplantation treatments.

The term "secreted phosphoprotein1" or "SPP1" or "osteopontin," as used herein, refers to any native SPP1 from any vertebrate source, including mammals such as primates (e.g. humans) and rodents (e.g., mice and rats), unless otherwise indicated. The term encompasses "full-length," unprocessed SPP1 as well as any form of SPP1 that results from processing in the cell. The term also encompasses naturally occurring variants of SPP1, e.g., splice variants or allelic variants. The amino acid sequence of an exemplary human SPP1 is shown in FIG. 11.

The phrase "substantially reduced" or "substantially different," as used herein, refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values).

The term "substantially similar" or "substantially the same," as used herein, refers to a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values).

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology, 6th* ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on inhibition of Notch pathway components for the treatment of liver cancer.

In one aspect, methods of treating a liver cancer in an individual in need thereof are provided, comprising the step of administering to the individual an effective amount of a Notch2 signaling inhibitor. In some embodiments, the liver cancer is hepatocellular carcinoma, hepatoma, cholangiocarcinoma, hepatoblastoma, hepatic carcinoma, hepatic angiosarcoma, or metastatic liver cancer. In some embodiments, the liver cancer is a refractory cancer.

Examples of Notch2 signaling inhibitors are known in the art and some are exemplified herein, including, but not limited to, soluble Notch receptors, soluble Notch ligand variants, e.g., dominant negative ligand variants, aptamers or oligopeptides that bind Notch2 or Jag1, organic or inorganic molecules that interfere specifically with Notch2 signaling, anti-Notch2 antagonist antibodies and anti-Jag1 antagonist antibodies. Examples of Notch2-specific antagonists include those described in U.S. Patent Application Publication No. US 2010/0111958 and Sjölund et al., J. Clin. Invest. 118(1):217-228 (2008).

In certain embodiments, the Notch2 signaling inhibitor is an anti-Notch2 antagonist antibody. In one such embodiment, the anti-Notch2 antagonist antibody is an antibody that binds to the extracellular domain of Notch2 and effects decreased Notch2 signaling. In one such embodiment, the anti-Notch2 antagonist antibody is an anti-Notch2 NRR antibody. Anti-Notch2 NRR antibodies include, but are not limited to, any anti-Notch2 NRR antibodies disclosed in International Application Publication No. WO2010039832, which is expressly incorporated by reference herein in its entirety. Such antibodies include, but are not limited to anti-Notch2 NRR antibodies that bind to the LNR-A and HD-C domains of Notch2 NRR. Exemplary anti-Notch2 NRR antibodies are monoclonal antibodies designated herein as Antibody B, Antibody B-1, Antibody B-2, and Antibody B-3. Antibody B that binds to Notch2 NRR was isolated from a phage library. That antibody was affinity matured to generate Antibody B-1, Antibody B-2, and Antibody B-3. The sequences of the heavy chain and light chain hypervariable regions (HVRs) of Antibody B, Antibody B-1, Antibody B-2, and Antibody B-3 are shown in FIGS. 12 and 13, respectively. The sequences of the heavy and light chain variable domains of Antibody B, Antibody B-1, Antibody B-2, and Antibody B-3 are shown in FIGS. 14 and 15. Further embodiments of anti-Notch2 NRR antibodies are provided as follows.

In one aspect, an antagonist antibody that specifically binds to Notch2 NRR is provided, wherein the antibody comprises at least one, two, three, four, five, or six HVRs selected from:

(a) an HVR-H1 comprising the amino acid sequence of SEQ ID NO:1;
(b) an HVR-H2 comprising the amino acid sequence of SEQ ID NO:3;
(c) an HVR-H3 comprising the amino acid sequence of SEQ ID NO:4;
(d) an HVR-L1 comprising an amino acid sequence that conforms to the consensus sequence of SEQ ID NO:9;
(e) an HVR-L2 comprising an amino acid sequence that conforms to the consensus sequence of SEQ ID NO:14; and
(f) an HVR-L3 comprising an amino acid sequence that conforms to the consensus sequence of SEQ ID NO:19.

In a further aspect, the antibody comprises an HVR-H3 comprising the amino acid sequence of SEQ ID NO:4 and at least one, two, three, four, or five HVRs selected from (a), (b), (d), (e), and (f) above. In a further aspect, the antibody comprises (a), (b), (c), (d), (e), and (f) above. With respect to (a), (d), (e), and (f), any one or more of the following embodiments are contemplated: HVR-H1 comprises an amino acid sequence of SEQ ID NO:1; HVR-L1 comprises an amino acid sequence selected from SEQ ID NOs:5-8; HVR-L2 comprises an amino acid sequence selected from SEQ ID NOs:10-13; and HVR-L3 comprises an amino acid sequence selected from SEQ ID NOs:15-18.

In another aspect, an antibody that specifically binds to Notch2 NRR is provided, wherein the antibody comprises an HVR-H1 comprising the amino acid sequence of SEQ ID NO:1, an HVR-H2 comprising the amino acid sequence of SEQ ID NO:3, and an HVR-H3 comprising the amino acid sequence of SEQ ID NO:4.

In another aspect, an antibody that specifically binds to Notch2 NRR is provided, wherein the antibody comprises an HVR-L1 comprising an amino acid sequence that conforms to the consensus sequence of SEQ ID NO:9, an HVR-L2 comprising an amino acid sequence that conforms to the consensus sequence of SEQ ID NO:14, and an HVR-L3 comprising an amino acid sequence that conforms to the consensus sequence of SEQ ID NO:19. The following embodiments are contemplated in any combination: HVR-L1 comprises an amino acid sequence selected from SEQ ID NOs:5-8; HVR-L2 comprises an amino acid sequence selected from SEQ ID NOs:10-13; and HVR-L3 comprises an amino acid sequence selected from SEQ ID NOs:15-18. In one embodiment, an antibody that binds to Notch2 NRR comprises an HVR-L1 comprising the amino acid sequence of SEQ ID NO:5; an HVR-L2 comprising the amino acid sequence of SEQ ID NO:10; and an HVR-L3 comprising the amino acid sequence of SEQ ID NO:15. In another embodiment, an antibody that binds to Notch2 NRR comprises an HVR-L1 comprising the amino acid sequence of SEQ ID NO:6; an HVR-L2 comprising the amino acid sequence of SEQ ID NO:11; and an HVR-L3 comprising the amino acid sequence of SEQ ID NO:16. In another embodiment, an antibody that binds to Notch2 NRR comprises an HVR-L1 comprising the amino acid sequence of SEQ ID NO:7; an HVR-L2 comprising the amino acid sequence of SEQ ID NO:12; and an HVR-L3 comprising the amino acid sequence of SEQ ID NO:17. In another embodiment, an antibody that binds to Notch2 NRR comprises an HVR-L1 comprising the amino acid sequence of SEQ ID NO:8; an HVR-L2 comprising the amino acid sequence of SEQ ID NO:13; and an HVR-L3 comprising the amino acid sequence of SEQ ID NO:18.

In one embodiment, an antibody that specifically binds to Notch2 NRR is provided, wherein the antibody comprises:

(a) an HVR-H1 comprising the amino acid sequence of SEQ ID NO:1;

(b) an HVR-H2 comprising the amino acid sequence of SEQ ID NO:3;

(c) an HVR-H3 comprising the amino acid sequence of SEQ ID NO:4;

(d) an HVR-L1 comprising the amino acid sequence of SEQ ID NO:5;

(e) an HVR-L2 comprising the amino acid sequence of SEQ ID NO:10; and (f) an HVR-L3 comprising the amino acid sequence of SEQ ID NO:15.

In another embodiment, an antibody that specifically binds to Notch2 NRR is provided, wherein the antibody comprises:

(a) an HVR-H1 comprising the amino acid sequence of SEQ ID NO:1;

(b) an HVR-H2 comprising the amino acid sequence of SEQ ID NO:3;

(c) an HVR-H3 comprising the amino acid sequence of SEQ ID NO:4;

(d) an HVR-L1 comprising the amino acid sequence of SEQ ID NO:6;

(e) an HVR-L2 comprising the amino acid sequence of SEQ ID NO:11; and (f) an HVR-L3 comprising the amino acid sequence of SEQ ID NO:16.

In another embodiment, an antibody that specifically binds to Notch2 NRR is provided, wherein the antibody comprises:

(a) an HVR-H1 comprising the amino acid sequence of SEQ ID NO:1;

(b) an HVR-H2 comprising the amino acid sequence of SEQ ID NO:3;

(c) an HVR-H3 comprising the amino acid sequence of SEQ ID NO:4;

(d) an HVR-L1 comprising the amino acid sequence of SEQ ID NO:7;

(e) an HVR-L2 comprising the amino acid sequence of SEQ ID NO:12; and (f) an HVR-L3 comprising the amino acid sequence of SEQ ID NO:17.

In another embodiment, an antibody that specifically binds to Notch2 NRR is provided, wherein the antibody comprises:

(a) an HVR-H1 comprising the amino acid sequence of SEQ ID NO:1;

(b) an HVR-H2 comprising the amino acid sequence of SEQ ID NO:3;

(c) an HVR-H3 comprising the amino acid sequence of SEQ ID NO:4;

(d) an HVR-L1 comprising the amino acid sequence of SEQ ID NO:8;

(e) an HVR-L2 comprising the amino acid sequence of SEQ ID NO:13; and (f) an HVR-L3 comprising the amino acid sequence of SEQ ID NO:18.

In certain embodiments, any of the above antibodies further comprises at least one framework selected from a VH subgroup III consensus framework and a VL subgroup I consensus framework.

In certain embodiments, an anti-Notch2 NRR antibody is affinity matured. For example, any one or more of the following substitutions in the indicated HVR positions (Kabat numbered) may be made in any combination:

in HVR-L1 (SEQ ID NO:5): S28N; I29N or V; S30R or K; S31R; Y32F in HVR-L2 (SEQ ID NO:10): G50R; S53I or T; A55E in HVR-L3 (SEQ ID NO:15): S931 or R; L96S or H

The specific antibodies disclosed herein, Antibody B as well as affinity matured forms of Antibody B (B-1, B-2, and B-3), may undergo further affinity maturation. Accordingly, affinity matured forms of any of the antibodies described herein are provided.

In certain embodiments, the Notch2 signaling inhibitor is an anti-Jag1 antagonist antibody. In one such embodiment, the anti-Jag1 antagonist antibody is an antibody that binds to the extracellular domain of Jag1 and effects decreased Notch2 signaling. In one such embodiment, the anti-Jag1 antagonist antibody is an anti-Jag1 EGF1-4 antibody. Anti-Jag1 antibodies include, but are not limited to, any anti-Jag1 antibodies disclosed herein.

In further embodiments, the antibody is an anti-Jag1 antibody. In some embodiments, the antibody comprises at least one, two, three, four, five, or six HVRs selected from: (a) HVR-H1 comprising the amino acid sequence of SEQ ID NO:81; (b) HVR-H2 comprising an amino acid sequence of SEQ ID NO:84; (c) HVR-H3 comprising an amino acid sequence of SEQ ID NO:87; (d) HVR-L1 comprising the amino acid sequence of SEQ ID NO:88; (e) HVR-L2 comprising the amino acid sequence of SEQ ID NO:89; and (f) HVR-L3 comprising an amino acid sequence of SEQ ID NO:92. In one embodiment, the antibody comprises: (a) an HVR-H1 comprising the amino acid sequence of SEQ ID NO:81; (b) an HVR-H2 comprising the amino acid sequence of SEQ ID NO:82; (c) an HVR-H3 comprising the amino acid sequence of SEQ ID NO:85; (d) an HVR-L1 comprising the amino acid sequence of SEQ ID NO:88; (e) an HVR-L2 comprising the amino acid sequence of SEQ ID NO:89; and (f) an HVR-L3 comprising the amino acid sequence of SEQ ID NO:90.

In one embodiment, the antibody comprises: (a) an HVR-H1 comprising the amino acid sequence of SEQ ID NO:81; (b) an HVR-H2 comprising the amino acid sequence of SEQ ID NO:82; (c) an HVR-H3 comprising the amino acid sequence of SEQ ID NO:86; (d) an HVR-L1 comprising the amino acid sequence of SEQ ID NO:88; (e) an HVR-L2 comprising the amino acid sequence of SEQ ID NO:89; and (f) an HVR-L3 comprising the amino acid sequence of SEQ ID NO:91. In one embodiment, the antibody comprises: (a) an HVR-H1 comprising the amino acid sequence of SEQ ID NO:81; (b) an HVR-H2 comprising the amino acid sequence of SEQ ID NO:83; (c) an HVR-H3 comprising the amino acid sequence of SEQ ID NO:85; (d) an HVR-L1 comprising the amino acid sequence of SEQ ID NO:88; (e) an HVR-L2 comprising the amino acid sequence of SEQ ID NO:89; and (f) an HVR-L3 comprising the amino acid sequence of SEQ ID NO:90.

In certain embodiments, an anti-Notch2 NRR antibody or anti-Jag1 antibody having any of the above HVR sequences can further comprise any suitable framework variable domain sequence, provided binding activity to Notch2 NRR and Jag1, respectively, is substantially retained. In certain embodiments, an anti-Notch2 NRR antibody or anti-Jag1 antibody comprises a human variable heavy (VH) consensus framework sequence, as in any of the VH consensus framework sequences shown in FIGS. 16A and 16B. In one embodiment, the VH consensus framework sequence comprises a human subgroup III heavy chain framework consensus sequence, e.g., as shown in FIGS. 16A and 16B. In another embodiment, the VH consensus framework sequence comprises an "Acceptor 2" framework sequence, e.g., as shown in FIGS. 16A and 16B. In a particular embodiment, the VH framework consensus sequence comprises FR1-FR4 of Acceptor 2B or Acceptor 2D, wherein the FR4 comprises SEQ ID NO:35 (FIGS. 16A and 16B), with the last residue of SEQ ID NO:35 (S11) optionally being substituted with alanine. In a further particular embodiment, the VH framework consensus sequence comprises the sequences of SEQ ID NOs:50; 51; 57 or 59; and 35, wherein S11 of SEQ ID NO:35 is optionally substituted with alanine.

In certain embodiments, an anti-Notch2 NRR antibody or anti-Jag1 antibody having any of the above HVR sequences can further comprise a human variable light (VL) consensus framework sequence as shown in FIG. 17. In one embodiment, the VL consensus framework sequence comprises a human VL kappa subgroup I consensus framework (κv1) sequence, e.g., as shown in FIG. 17. In another embodiment, the VL framework consensus sequence comprises FR1-FR4 of huMAb4D5-8 as shown in FIG. 18 or 19. In a particular embodiment, the VL framework consensus sequence comprises the sequences of SEQ ID NOs:60, 61, 62, and 63.

In another aspect, an anti-Notch2 NRR antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NOs:20. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Notch2 NRR antibody comprising that sequence retains the ability to bind to Notch2 NRR. In certain embodiments, a total of 1 to 10 amino acids have been substituted, inserted and/or deleted in the amino acid sequence of SEQ ID NOs:20. In certain embodiments, substitutions, insertions, or deletions occur in regions outside the HVRs (i.e., in the FRs). In a particular embodiment, the VH comprises one, two or three HVRs selected from: (a) an HVR-H1 comprising the amino acid sequence of SEQ ID NO:1, (b) an HVR-H2 comprising the amino acid sequence of SEQ ID NO:3, and (c) an HVR-H3 comprising the amino acid sequence of SEQ ID NO:4.

In another aspect, an antibody that specifically binds to Notch2 NRR is provided, wherein the antibody comprises a light chain variable domain (VL) having at least 90%, 91%, 92%, 93%, 94%, 95%, 96%, 97%, 98%, 99%, or 100% sequence identity to an amino acid sequence selected from SEQ ID NOs:22-25. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Notch2 NRR antibody comprising that sequence retains the ability to bind to Notch2 NRR. In certain embodiments, a total of 1 to 10 amino acids have been substituted, inserted and/or deleted in an amino acid sequence selected from SEQ ID NOs:22-25. In certain embodiments, the substitutions, insertions, or deletions occur in regions outside the HVRs (i.e., in the FRs). In a particular embodiment, the VL comprises one, two or three HVRs selected from (a) an HVR-L1 comprising an amino acid sequence that conforms to the consensus sequence of SEQ ID NO:9; (b) an HVR-L2 comprising an amino acid sequence that conforms to the consensus sequence of SEQ ID NO:14; and (c) an HVR-L3 comprising an amino acid sequence that conforms to the consensus sequence of SEQ ID NO:19. In one such embodiment, the VL comprises one, two or three HVRs selected from (a) an HVR-L1 comprising an amino acid sequence selected from SEQ ID NOs:5-8; (b) an HVR-L2 comprising an amino acid sequence selected from SEQ ID NOs:10-13; and (c) an HVR-L3 comprising an amino acid sequence selected from SEQ ID NOs:15-18. In one such embodiment, the VL comprises one, two or three HVRs selected from (a) an HVR-L1 comprising the amino acid sequence of SEQ ID NO:5; (b) an HVR-L2 comprising the amino acid sequence of SEQ ID NO:10; and (c) an HVR-L3 comprising the amino acid sequence of SEQ ID NO:15. In another such embodiment, the VL comprises one, two or three HVRs selected from (a) an HVR-L1 comprising the amino acid sequence of SEQ ID NO:6; (b) an HVR-L2 comprising the amino acid sequence of SEQ ID NO:11; and (c) an HVR-L3 comprising the amino acid sequence of SEQ ID NO:16. In another such embodiment, the VL comprises one, two or three HVRs selected from (a) an HVR-L1 comprising the amino acid sequence of SEQ ID NO:7; (b) an HVR-L2 comprising the amino acid sequence of SEQ ID NO:12; and (c) an HVR-L3 comprising the amino acid sequence of SEQ ID NO:17. In another such embodiment, the VL comprises one, two or three HVRs selected from (a) an HVR-L1 comprising the amino acid sequence of SEQ ID NO:8; (b) an HVR-L2 comprising the amino acid sequence of SEQ ID NO:13; and (c) an HVR-L3 comprising the amino acid sequence of SEQ ID NO:18.

In certain embodiments of the variant VH and VL sequences provided above, substitutions, insertions, or deletions may occur within the HVRs. In such embodiments, substitutions, insertions, or deletions may occur within one or more HVRs so long as such alterations do not substantially reduce the ability of the antibody to bind antigen. For example, conservative alterations that do not substantially reduce binding affinity may be made in HVRs. In certain instances, alterations in HVRs may actually improve antibody affinity. Such alterations may be made in HVR "hotspots" (i.e., residues encoded by codons that undergo mutation at high frequency during the somatic maturation process) in order to increase antibody affinity. (See, e.g., Chowdhury, *Methods Mol. Biol.* 207:179-196, 2008.) In certain embodiments of the variant VH and VL sequences provided above, each HVR either is conserved (unaltered), or contains no more than a single amino acid substitution, insertion or deletion.

In another aspect, an antibody that specifically binds Notch2 NRR is provided, wherein the antibody comprises a VH as in any of the embodiments provided above, and a VL as in any of the embodiments provided above. In one embodiment, the antibody comprises a VH having at least 90%, 91%, 92%, 93%, 94%, 95%, 96%, 97%, 98%, 99%, or 100% sequence identity to the amino acid sequence of SEQ ID NO:20, and a VL having at least 90%, 91%, 92%, 93%, 94%, 95%, 96%, 97%, 98%, 99%, or 100% sequence identity to the amino acid sequence of SEQ ID NO:22. In one such embodiment, the VH comprises one, two or three HVRs selected from: (a) an HVR-H1 comprising the amino acid sequence of SEQ ID NO:1, (b) an HVR-H2 comprising the amino acid sequence of SEQ ID NO:3, and (c) an HVR-H3 comprising the amino acid sequence of SEQ ID NO:4, and the VL comprises one, two or three HVRs selected from (a) an HVR-L1 comprising the amino acid sequence of SEQ ID NO:5; (b) an HVR-L2 comprising the amino acid sequence of SEQ ID NO:10; and (c) an HVR-L3 comprising the amino acid sequence of SEQ ID NO:15. In a particular embodiment, the antibody comprises a VH comprising the amino acid sequence of SEQ ID NO:20, and a VL comprising the amino acid sequence of SEQ ID NO:22.

In another embodiment, an anti-Notch2 NRR antibody that specifically binds Notch2 NRR comprises a VH having at least 90%, 91%, 92%, 93%, 94%, 95%, 96%, 97%, 98%, 99%, or 100% sequence identity to the amino acid sequence of SEQ ID NO:20, and a VL having at least 90%, 91%, 92%, 93%, 94%, 95%, 96%, 97%, 98%, 99%, or 100% sequence identity to an amino acid sequence selected from SEQ ID NOs:23-25. In one such embodiment, the VH comprises one, two or three HVRs selected from: (a) an HVR-H1 comprising the amino acid sequence of SEQ ID NO:1, (b) an HVR-H2 comprising the amino acid sequence of SEQ ID NO:3, and (c) an HVR-H3 comprising the amino acid sequence of SEQ ID NO:4, and the VL comprises one, two or three HVRs selected from (a) an HVR-L1 comprising an amino acid sequence selected from SEQ ID NOs:6-8; (b) an HVR-L2 comprising an amino acid sequence selected from SEQ ID NOs:11-13; and (c) an HVR-L3 comprising an amino acid sequence selected from SEQ ID NOs:16-18. In particular embodiments, the antibody comprises a VH comprising the amino acid sequence of SEQ ID NO:20 and a VL comprising an amino acid sequence selected from SEQ ID NOs:23-25.

In another aspect, an antibody that specifically binds Jag1 is provided, wherein the antibody comprises a VH as in any of the embodiments provided above, and a VL as in any of the embodiments provided above. In one embodiment, the antibody comprises a VH having at least 90%, 91%, 92%, 93%, 94%, 95%, 96%, 97%, 98%, 99%, or 100% sequence identity to an amino acid sequence selected from SEQ ID NOs:93-95, and a VL having at least 90%, 91%, 92%, 93%, 94%, 95%, 96%, 97%, 98%, 99%, or 100% sequence identity to an amino acid sequence selected from SEQ ID NOs:96-98. In one such embodiment, the VH comprises one, two or three HVRs selected from: (a) an HVR-H1 comprising the amino acid sequence of SEQ ID NO:81, (b) an HVR-H2 comprising the amino acid sequence of SEQ ID NO:82, and (c) an HVR-H3 comprising the amino acid sequence of SEQ ID NO:85, and the VL comprises one, two or three HVRs selected from (a) an HVR-L1 comprising the amino acid sequence of SEQ ID NO:88; (b) an HVR-L2 comprising the amino acid sequence of SEQ ID NO:89; and (c) an HVR-L3 comprising the amino acid sequence of SEQ ID NO:90. In a particular embodiment, the antibody comprises a VH comprising the amino acid sequence of SEQ ID NO:93, and a VL comprising the amino acid sequence of SEQ ID NO:96.

In another embodiment, an anti-Jag1 antibody that specifically binds Jag1 comprises a VH having at least 90%, 91%, 92%, 93%, 94%, 95%, 96%, 97%, 98%, 99%, or 100% sequence identity to the amino acid sequence of SEQ ID NO:94, and a VL having at least 90%, 91%, 92%, 93%, 94%, 95%, 96%, 97%, 98%, 99%, or 100% sequence identity to the amino acid sequence of SEQ ID NO:97. In one such embodiment, the VH comprises one, two or three HVRs selected from: (a) an HVR-H1 comprising the amino acid sequence of SEQ ID NO:81, (b) an HVR-H2 comprising the amino acid sequence of SEQ ID NO:82, and (c) an HVR-H3 comprising the amino acid sequence of SEQ ID NO:86, and the VL comprises one, two or three HVRs selected from (a) an HVR-L1 comprising the amino acid sequence of SEQ ID NO:88; (b) an HVR-L2 comprising the amino acid sequence of SEQ ID NO:89; and (c) an HVR-L3 comprising the amino acid sequence of SEQ ID NO:91. In particular embodiments, the antibody comprises a VH comprising the amino acid sequence of SEQ ID NO:94 and a VL comprising the amino acid sequence of SEQ ID NO:97.

In another embodiment, an anti-Jag1 antibody that specifically binds Jag1 comprises a VH having at least 90%, 91%, 92%, 93%, 94%, 95%, 96%, 97%, 98%, 99%, or 100% sequence identity to the amino acid sequence of SEQ ID NO:95, and a VL having at least 90%, 91%, 92%, 93%, 94%, 95%, 96%, 97%, 98%, 99%, or 100% sequence identity to the amino acid sequence of SEQ ID NO:98. In one such embodiment, the VH comprises one, two or three HVRs selected from: (a) an HVR-H1 comprising the amino acid sequence of SEQ ID NO:81, (b) an HVR-H2 comprising the amino acid sequence of SEQ ID NO:83, and (c) an HVR-H3 comprising the amino acid sequence of SEQ ID NO:85, and the VL comprises one, two or three HVRs selected from (a) an HVR-L1 comprising the amino acid sequence of SEQ ID NO:88; (b) an HVR-L2 comprising the amino acid sequence of SEQ ID NO:89; and (c) an HVR-L3 comprising the amino acid sequence of SEQ ID NO:90. In particular embodiments, the antibody comprises a VH comprising the amino acid sequence of SEQ ID NO:95 and a VL comprising the amino acid sequence of SEQ ID NO:98.

In certain embodiments, an affinity-matured form of any of the above antibodies is provided. In further embodiments, a recombinant protein that specifically binds Notch2 NRR or Jag1 is provided, wherein the recombinant protein comprises an antigen binding site(s) of any of the above antibodies. In one such embodiment, a recombinant protein comprises any one or more of the HVRs provided above.

In certain embodiments, a polynucleotide encoding any of the above antibodies is provided. In one embodiment, a vector comprising the polynucleotide is provided. In one embodiment, a host cell comprising the vector is provided. In one embodiment, the host cell is eukaryotic. In one embodiment, the host cell is a CHO cell. In one embodiment, a method of making an anti-Notch2 NRR antibody is provided, wherein the method comprises culturing the host cell under conditions suitable for expression of the polynucleotide encoding the antibody, and isolating the antibody.

In another embodiment, an isolated antibody is provided that binds to the same epitope as an antibody provided herein. In one embodiment, an isolated anti-Notch2 NRR antibody is provided that binds to the same epitope as an antibody selected from Antibody B, Antibody B-1, Antibody B-2, and Antibody B-3. In another embodiment, the invention provides an anti-Notch2 NRR antibody that competes for binding with an antibody selected from Antibody B, Antibody B-1, Antibody B-2, and Antibody B-3. In another embodiment, an isolated antibody is provided that binds to at least one domain selected from the LNR-A domain and the HD-C domain of Notch2. In one such embodiment, the antibody binds to both the LNR-A domain and the HD-C domain. In another such embodiment, the antibody further binds to the LNR-B and/or HD-N domains.

In one embodiment, an isolated anti-Jag1 antibody is provided that binds to the same epitope as an antibody selected from Antibody A, Antibody A-1, and Antibody A-2. In another embodiment, the invention provides an anti-Jag1 antibody that competes for binding with an antibody selected from Antibody A, Antibody A-1, and Antibody A-2. In another embodiment, an isolated antibody is provided that binds to at least one domain selected from the DSL domain and the EGF domain of Jag1. In one such embodiment, the antibody binds to EGF1-4 of Jag1.

Any of the Notch2 signaling inhibitors provided herein may be used in the methods described herein.

The invention also provides methods for selecting a therapeutic treatment for a patient having a liver cancer, the method comprising determining expression of one or more of Notch2, Jag1 and SPP1 in a sample obtained from the patient. In some embodiments, the patient is selected for treatment with a Notch2 signaling inhibitor if expression of one or more of Notch2, Jag1 and SPP1 is detected in the patient sample. In some embodiments, elevated expression of one or more of Notch2, Jag1 and Spp1 in the sample obtained from the patient, relative to a control, identifies the patient as suitable for receiving treatment with a Notch2 signaling inhibitor, as described herein. In some embodiments, additional parameters, such as, e.g., examination by a physician, histologic evaluation of a biopsy, determination of serum levels characterizing the liver cancer, are employed to identify the patient for receiving the Notch2 signaling inhibitor treatment.

In some embodiments, a sample or biopsy from the patient is analyzed for mRNA expression of one or more of Notch2, Jag1 and Spp1 using methods well known in the art, such as, e.g., quantitative PCR analysis, and compared to expression of the same gene or genes in a biopsy obtained from a control individual or compared to a reference value. In some embodiments, expression is determined using enzyme linked immunosorbent assay (ELISA). In some embodiments, a sample or biopsy from the patient is analyzed for Notch2 activation, for example by detection of the activated form of Notch2 as described herein.

In one aspect, methods are provided for preventing liver cancer in an individual at risk of having liver cancer, comprising the step of administering to the individual an effective amount of a Notch2 signaling inhibitor. In some embodiments, the individual has a liver condition selected from the group consisting of hepatitis B or C, cirrhosis of the liver, benign liver tumors, hemangiomas, hepatic adenomas, and focal nodular hyperplasia. In some embodiments, the method further comprises administering at least one additional therapeutic agent. Examples of additional therapeutic agents include growth inhibitory agents, such as cytotoxic agents, peptides, small-molecules and antibodies.

In another aspect, methods are provided for inhibiting the growth of a cell that expresses secreted phosphoprotein1 (SPP1), comprising contacting the cell with a Notch2 signaling inhibitor, thereby inhibiting growth of the cell. In one embodiment, SPP1 protein comprises the amino acid sequence shown in FIG. 11. In one embodiment, contacting the cell with the Notch2 signaling inhibitor reduces SPP1 expression in the cell. For example, contacting the cell with the Notch2 signaling inhibitor reduces SPP1 expression in the cell by at least about 50%, 60%, 70%, 80%, 90%, or 90%. The expression of SPP1 mRNA or protein can be determined by any method in the art. In some embodiments, the cell is a liver cancer cell. In some embodiments, the liver cancer cell expresses EpCAM, AFP, AFP and EpCAM, Notch2, Jag1, Notch2 and Jag1, nuclear Notch2 ICD, Ras, Prom1, Spp1, FoxM1, Plk1, ccnb1, Aurkb, Wnt2, Axin2, or Glul, or any combination thereof. In some embodiments, contacting the cell with the Notch2 signaling inhibitor results in a decrease in the expression in the cell of at least one of EpCAM, AFP, Notch2, Notch2 ICD, Jag1, Prom1, Spp1, FoxM1, Plk1, ccnb1 and Aurkb. In some embodiments, administering the Notch2 signaling inhibitor results in an increase in the expression in the cell of at least one of Wnt2, Axin2 and Glul. In some embodiments, expression is determined by RNAseq, microarray analysis, immunohistochemistry, enzyme-linked immunosorbent assay, and Western blotting.

In another aspect, methods are provided for therapeutically treating a mammal having a liver cancer comprising cells that express an Spp1 gene encoding a peptide comprising an amino acid sequence having at least 90% identity to the polypeptide shown in FIG. 11, comprising administering to the mammal a therapeutically effective amount of a Notch2 signaling inhibitor, thereby effectively treating the mammal.

In another aspect, methods are provided for treating or preventing a liver cell proliferative disorder associated with increased expression or activity of a protein having at least 90% amino acid sequence identity to the polypeptide shown in FIG. 8C, comprising administering to an individual in need of such treatment an effective amount of an anti-Jag1 antagonist antibody, thereby effectively treating or preventing the liver cell proliferative disorder. In some embodiments, the cell proliferative disorder is a cancer, such as liver cancer. In some embodiments the individual has a liver condition selected from the group consisting of hepatitis B or C, cirrhosis of the liver, benign liver tumors, hemangiomas, hepatic adenomas, and focal nodular hyperplasia.

In one aspect, methods are provided for reducing serum SPP1 protein levels in an individual, the method comprising administering to the individual an effective amount of a Notch2 signaling inhibitor thereby reducing serum SPP1 levels in the individual. In some embodiments, reducing is relative to serum SPP1 levels in the individual prior to administering the Notch2 signaling inhibitor. In some embodiments, reducing is relative to a reference level. In one embodiment, the individual has a liver cancer. In one embodiment, the serum SPP1 protein levels prior to administering the Notch2 signaling inhibitor to the individual are at least about 80 ng/ml. In certain embodiments, the serum SPP1 protein levels prior to administering the Notch2 signaling inhibitor to the individual are between about 80 ng/ml and about 500 ng/ml, between about 86 ng/ml and about 250 ng/ml, between about 120 ng/ml and about 170 ng/ml, or about 165 ng/ml. In some embodiments, administering the Notch2 signaling inhibitor to the individual results in serum SPP1 protein levels of less than 80 ng/ml. In specific embodiments, serum SPP1 protein levels prior to administering the Notch2 signaling inhibitor are 24 hours prior to administering the Notch2 signaling inhibitor. Serum SPP1 protein levels prior to or following administration of the Notch2 signaling inhibitor may be determined by any appropriate method, such as enzyme-linked immunosorbent assay. In specific embodiments, serum SPP1 protein levels are reduced about one, two, three, six or 12 month after administering the Notch2 signaling inhibitor.

In one aspect, methods are provided for therapeutically treating a liver tumor in a mammal, wherein the growth of the liver tumor is at least in part dependent upon a growth potentiating effect of Notch2 signaling, comprising contacting the tumor with an antibody that binds to Notch2 or Jag1, thereby effectively treating the tumor. In one embodiment, binding of the antibody to the tumor antagonizes the growth-potentiating activity of Notch2.

In one aspect, methods are provided for preventing recurrence of liver cancer comprising administering to an individual who has been treated for liver cancer and who has elevated serum SPP1 protein levels an effective amount of a Notch2 signaling inhibitor. In one embodiment, the serum SPP1 protein levels of the individual are at least about 80 ng/ml. In certain embodiments, the serum SPP1 protein levels prior to administering the Notch2 signaling inhibitor to the individual are between about 80 ng/ml and about 500 ng/ml, between about 86 ng/ml and about 250 ng/ml, between about 120 ng/ml and about 170 ng/ml, or about 165 ng/ml. In some embodiments, administering the Notch2 signaling inhibitor to the individual results in serum SPP1 protein levels of less than 80 ng/ml.

In some aspects, methods are provided for treating an individual having a liver cancer, comprises the steps of administering to the individual a Notch2 signaling inhibitor; and determining Notch2 signaling, wherein a decrease in Notch2 signaling following treatment, compared to Notch2 signaling prior to treatment, is indicative of reduction of liver cancer in the individual. In some embodiments, Notch2 signaling is determined by measuring Notch2 ICD nuclear localization, e.g., by immunohistochemical analysis. In some embodiments, Notch2 signaling is determined by measuring expression of a gene selected from the group consisting of Notch2, Jag1, Hes and Hey1. In some embodiments, the liver cancer is hepatocellular carcinoma, hepatoma, cholangiocarcinoma, hepatoblastoma, hepatic carcinoma, hepatic angiosarcoma, and metastatic liver cancer. In some embodiments, the Notch2 signaling inhibitor is an siRNA, small-molecule inhibitor or antibody. In some embodiments, the antibody is an antagonist antibody, such as an anti-Notch2 antagonist antibody or an anti-Jag1 antagonist antibody.

In some aspects, methods for inhibiting cellular proliferation comprising treating mammalian liver cancer cells with an antibody to Notch2 or Jag1, whereby proliferation of the liver cancer cell is inhibited. In certain embodiments, the antibody is an anti-Notch2 or anti-Jag1 antagonist antibody is as described herein. In certain embodiments, the antibody is a human, humanized, or chimeric antibody. In certain embodiments, any of the antibodies of the above embodiments is an antibody fragment. In certain embodiments, the cells are in a patient. In certain embodiments, the cells are in a culture medium.

Notch2 signaling inhibitors of the invention, such as anti-Notch2 and anti-Jag1 antibodies, can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antagonist of the invention can occur prior to, simultaneously, and/or following, administration of the additional therapeutic agent and/or adjuvant. Notch2 signaling inhibitors of the invention can also be used in combination with radiation therapy.

The antagonist can be administered to a human patient by any known method, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The Notch2 signaling inhibitor might be administered as a protein or as a nucleic acid encoding a protein (see, for example, International Application Publication No. WO96/07321). Other therapeutic regimens may be combined with the administration of the Notch2 signaling inhibitor. The combined administration includes co-administration, using separate formulations or a single pharmaceutical formulation, and consecutive administration in either order, wherein preferably there is a time period while both (or all) active agents simultaneously exert their biological activities. In some embodiments, such combined therapy results in a synergistic therapeutic effect.

The dosage and mode of administration will be chosen by the physician according to known criteria. The appropriate dosage of antibody, or other Notch2 signaling inhibitor, will depend on the type of disease to be treated, the severity and course of the disease, whether the antibody, oligopeptide or organic molecule is administered for preventive or therapeutic purposes, previous therapy, the patient's clinical history and response to the Notch2 signaling inhibitor, and the discretion of the attending physician. The Notch2 signaling inhibitor can be administered to the patient at one time or over a series of treatments.

Success of treatment of liver cancer can be monitored by assessing parameters of liver function and recovery. Such parameters include, but are not limited to, improved liver function tests, (e.g., assessing serum albumin, bilirubin, bile acids, total protein, clotting times), liver enzymes (e.g., alanine transaminase, aspartate transaminase, alkaline phosphatase, gamma glutamyl transpeptidase), histologic appearance (e.g., needle biopsy showing improved hepatic architecture), and imaging modalities (e.g., ultrasound, magnetic resonance imaging for fibrosis and liver size). Success of treatment can also be monitored by measuring serum levels of SPP1 protein, wherein a decrease in serum levels in a treated patient, compared to pre-treatment levels, indicate successful treatment.

In a further aspect, a Notch2 signaling inhibitor is an antibody used in any of the above embodiments that incorporates any of the features, singly or in combination, as described in Sections 1-7 below.

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACOR®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2

μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6\ M^{-1}\ s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Jag1 and the other is for any other antigen. In certain embodiments, one of the binding specificities is for Notch2 and the other is for any other antigen. In certain embodiments, bispecific antibodies may bind to two different epitopes of Jag1. In certain embodiments, bispecific antibodies may bind to two different epitopes of Notch2. Bispecific antibodies may also be used to localize cytotoxic agents to cells which express Jag1 and/or Notch2. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to Jag1 or Notch2, as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, *FUT*8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S, and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-Jag1 antibody described herein is provided. In one embodiment, isolated nucleic acid encoding an anti-Notch2 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-Jag1 antibody is provided, wherein the method comprises culturing a host cell comprising a nucleic acid encoding the antibody, as provided above, under conditions suitable for expression of the antibody, and optionally recovering the antibody from the host cell (or host cell culture medium). In one embodiment, a method of making an anti-Notch2 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Jag1 antibody or an anti-Notch2 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

C. Assays

The antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with Antibody A, A-1 or A-2 for binding to Jag1. In certain embodiments, such a competing antibody binds to the same epitope (e.g., a linear or a conformational epitope) that is bound by Antibody A, A-1 or A-2. In another aspect, competition assays may be used to identify an antibody that competes with Antibody B, B-1, B-2 or B-3 for binding to Notch2. In certain embodiments, such a competing antibody binds to the same epitope (e.g., a linear or a conformational epitope) that is bound by Antibody B, B-1, B-2 or B-3. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized Jag1 is incubated in a solution comprising a first labeled antibody that binds to Jag1 (e.g., Antibody A, A-1 or A-2) and a second unlabeled antibody that is being tested for its ability to compete with the first antibody for binding to Jag1. The second antibody may be present in a hybridoma supernatant. As a control, immobilized Jag1 is incubated in a solution comprising the first labeled antibody but not the second unlabeled antibody. After incubation under conditions permissive for binding of the first antibody to Jag1, excess unbound antibody is removed, and the amount of label associated with immobilized Jag1 is measured. If the amount of label associated with immobilized Jag1 is substantially reduced in the test sample relative to the control sample, then that indicates that the second antibody is competing with the first antibody for binding to Jag1. See Harlow and Lane (1988) *Antibodies: A Laboratory Manual* ch. 14 (Cold Spring Harbor Laboratory, Cold Spring Harbor, N.Y.). In another exemplary competition assay, immobilized Notch2 is incubated in a solution comprising a first labeled antibody that binds to Notch2 (e.g., Antibody B, B-1, B-2 or B3) and a second unlabeled antibody that is being tested for its ability to compete with the first antibody for binding to Notch2. The second antibody may be present in a hybridoma supernatant. As a control, immobilized Notch2 is incubated in a solution comprising the first labeled antibody but not the second unlabeled antibody. After incubation under conditions permissive for binding of the first antibody to Notch2, excess unbound antibody is removed, and the amount of label associated with immobilized Notch2 is measured. If the amount of label associated with immobilized Jag1 is substantially reduced in the test sample relative to the control sample, then that indicates that the second antibody is competing with the first antibody for binding to Notch2.

2. Activity Assays

In one aspect, assays are provided for identifying Notch2 signaling inhibitor antibodies, such as anti-Jag1 antibodies and anti-Notch2 antibodies, having biological activity. Biological activity may include, e.g., inhibition or reduction of Notch2 activity, e.g., Notch2 signaling, inhibition or reduction of Jag1-mediated Notch signaling, e.g., Jag1-mediated Notch2 signaling. Antibodies having such biological activity in vivo and/or in vitro are also provided.

In certain embodiments, an antibody of the invention is tested for such biological activity. In certain embodiments, an antibody of the invention is tested for its ability to inhibit reduce Spp1 expression. An exemplary assay is provided in the Examples. In certain other embodiments, an antibody of the invention is tested for its ability to inhibit expression of a reporter gene that is responsive to Notch2 signaling. In certain other embodiments, an antibody of the invention is tested for its ability to inhibit expression of a reporter gene that is responsive to Jag1-mediated signaling, e.g., Jag1-mediated Notch2 signaling. In one exemplary assay, NIH-3T3 cells stably transfected with Notch 2 or transiently transfected with plasmids containing other Notch receptors are co-transfected with a Notch-responsive TP-I (12×CSL) Firefly luciferase reporter and a constitutively active *Renilla* Luciferase reporter (pRL-CMV, Promega) to control for transfection efficiency. Cells are allowed to recover from the transfection from 6 hours to overnight. Treatments of antibodies and NI H-3T3 cells stably transfected with ligand are used to stimulate the receptor cells. After 20 hours, firefly and *Renilla* luciferase are measured with Dual GIo Luciferase Assay system (Promega). Replicates are analyzed for each condition by dividing the Firefly signal by the *Renilla* signal to control for transfection efficiency. The mean and standard deviation are calculated and values are normalized to calculated values for co-culture stimulated with NIH-3T3 cells without ligand transfected.

In certain embodiments, an antibody of the invention is tested for its ability to inhibit cell growth or proliferation in vitro. Assays for inhibition of cell growth or proliferation are well known in the art. Certain assays for cell proliferation, exemplified by the "cell killing" assays described herein, measure cell viability. One such assay is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) *J. Immunol. Meth.* 160:81-88, U.S. Pat. No. 6,602,677. The assay may be conducted in 96- or 384-well format, making it amenable to automated high-throughput screening (HTS). See Cree et al (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

Another assay for cell proliferation is the "MTT" assay, a colorimetric assay that measures the oxidation of 3-(4,5-dimethylthiazol-2-yl)-2,5-diphenyltetrazolium bromide to formazan by mitochondrial reductase. Like the CellTiter-Glo™ assay, this assay indicates the number of metabolically active cells present in a cell culture. See, e.g., Mosmann (1983) *J. Immunol. Meth.* 65:55-63, and Zhang et al. (2005) *Cancer Res.* 65:3877-3882.

In one aspect, an antibody of the invention is tested for its ability to induce cell death in vitro. Assays for induction of cell death are well known in the art. In some embodiments, such assays measure, e.g., loss of membrane integrity as indicated by uptake of propidium iodide (PI), trypan blue (see Moore et al. (1995) *Cytotechnology,* 17:1-11), or 7AAD. In an exemplary PI uptake assay, cells are cultured in Dulbecco's Modified Eagle Medium (D-MEM):Ham's F-12 (50:50) supplemented with 10% heat-inactivated FBS (Hyclone) and 2 mM L-glutamine. Thus, the assay is performed in the absence of complement and immune effector cells. Cells are seeded at a density of $3\times10^6$ per dish in 100×20 mm dishes and allowed to attach overnight. The medium is removed and replaced with fresh medium alone or medium containing various concentrations of the antibody or immunoconjugate. The cells are incubated for a 3-day time period. Following treatment, monolayers are washed with PBS and detached by trypsinization. Cells are then centrifuged at 1200 rpm for 5 minutes at 4° C., the pellet resuspended in 3 ml cold $Ca^+$ binding buffer (10 mM Hepes, pH 7.4, 140 mM NaCl, 2.5 mM $CaCl_2$) and aliquoted into 35 mm strainer-capped 12×75 mm tubes (1 ml per tube, 3 tubes per treatment group) for removal of cell clumps. Tubes then receive PI (10 μg/ml). Samples are analyzed using a FACSCAN™ flow cytometer and FACSCONVERT™ CellQuest software (Becton Dickinson). Antibodies which induce statistically significant levels of cell death as determined by PI uptake are thus identified.

In one aspect, an antibody of the invention is tested for its ability to induce apoptosis (programmed cell death) in vitro. An exemplary assay for antibodies or immunoconjugates that induce apoptosis is an annexin binding assay. In an exemplary annexin binding assay, cells are cultured and seeded in dishes as discussed in the preceding paragraph. The medium is removed and replaced with fresh medium alone or medium containing 0.001 to 10 μg/ml of the antibody or immunoconjugate. Following a three-day incubation period, monolayers are washed with PBS and detached by trypsinization. Cells are then centrifuged, resuspended in $Ca^+$ binding buffer, and aliquoted into tubes as discussed in the preceding paragraph. Tubes then receive labeled annexin (e.g. annexin V-FITC) (1 μg/ml). Samples are analyzed using a FACSCAN™ flow cytometer and FACSCONVERT™ CellQuest software (BD Biosciences). Antibodies that induce statistically significant levels of annexin binding relative to control are thus identified. Another exemplary assay for antibodies or immunoconjugates that induce apoptosis is a histone DNA ELISA colorimetric assay for detecting internucleosomal degradation of genomic DNA. Such an assay can be performed using, e.g., the Cell Death Detection ELISA kit (Roche, Palo Alto, Calif.).

Cells for use in any of the above in vitro assays include cells or cell lines that naturally express Notch2 and/or Jag1 or that have been engineered to express Notch2 and/or Jag1. Such cells include tumor cells that overexpress Notch2 and/or Jag1 relative to normal cells of the same tissue origin. Such cells also include cell lines (including tumor cell lines) that express Notch2 and/or Jag1 and cell lines that do not normally express Notch2 and/or Jag1 but have been transfected with nucleic acid encoding Notch2 and/or Jag1. Exemplary cell lines provided herein for use in any of the above in vitro assays include NIH-3T3 cells.

In one aspect, an antibody of the invention is tested for its ability to inhibit cell growth or proliferation in vivo. In certain embodiments, an anti-Jag1 antibody thereof is tested for its ability to inhibit tumor growth in vivo. In certain embodiments, an anti-Notch2 antibody thereof is tested for its ability to inhibit tumor growth in vivo. In vivo model systems, such as xenograft models, can be used for such testing. In an exemplary xenograft system, human tumor cells are introduced into a suitably immunocompromised non-human animal, e.g., an athymic "nude" mouse. An antibody of the invention is administered to the animal. The ability of the antibody to inhibit or decrease tumor growth is measured. In certain embodiments of the above xenograft system, the human tumor cells are tumor cells from a human patient. Such xenograft models are commercially available from Oncotest GmbH (Frieberg, Germany). In certain embodiments, the human tumor cells are cells from a human tumor cell line, such as HepG2, Hep3B, PCL/PRF/5, Snu387, Snu398, Snu423, Snu449, Snu475, Huh-7, HLE, HLF, JHH1, JHH4, JHH5 and JHH7. In certain embodiments, the human tumor cells are introduced into a suitably immunocompromised non-human animal by subcutaneous injection or by transplantation into a suitable site, such as a mammary fat pad.

It is understood that any of the above assays may be carried out using an immunoconjugate of the invention in place of or in addition to an Notch2 signaling inhibitor.

D. Immunoconjugates

The invention also provides immunoconjugates comprising an anti-Notch2 antibody or anti-Jag1 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

E. Methods and Compositions for Diagnostics and Detection

In certain embodiments, any of the antibodies provided herein is useful for detecting the presence of a Notch2 or fragment thereof, or a Jag1 or fragment thereof, in a biological sample. The term "detecting" as used herein encompasses quantitative or qualitative detection. In certain embodiments, a biological sample comprises a cell or tissue, such as hepatocyte, liver cancer cell and liver tumor tissue.

In one embodiment, an anti-Notch2 antibody for use in a method of diagnosis or detection is provided. In a further aspect, a method of detecting the presence of Notch2 in a biological sample is provided. In certain embodiments, a method of detecting the presence of Notch2 intracellular domain (ICD) in a biological sample is provided. In certain embodiments, the method comprises contacting the biological sample with an anti-Notch2 antibody as described herein under conditions permissive for binding of the anti-Notch2 antibody to Notch2, and detecting whether a complex is formed between the anti-Notch2 antibody and Notch2. Such method may be an in vitro or in vivo method. In one embodiment, an anti-Notch2 antibody is used to select subjects eligible for therapy with an anti-Notch2 antibody, as described above, e.g. where Notch2, in particular activated Notch2, is a biomarker for selection of patients.

In one embodiment, an anti-Jag1 antibody for use in a method of diagnosis or detection is provided. In a further aspect, a method of detecting the presence of Jag1 in a biological sample is provided. In certain embodiments, a method of detecting the presence of Jag1 intracellular domain (ICD) in a biological sample is provided. In certain embodiments, the method comprises contacting the biological sample with an anti-Jag1 antibody as described herein under conditions permissive for binding of the anti-Jag1 antibody to Jag1, and detecting whether a complex is formed between the anti-Jag1 antibody and Jag1. Such method may be an in vitro or in vivo method. In one embodiment, an anti-Jag1 antibody is used to select subjects eligible for therapy with an anti-Jag1 antibody, as described above, e.g. where Jag1 is a biomarker for selection of patients.

Exemplary disorders that may be diagnosed using an antibody of the invention include liver cancer, specifically, hepatocellular carcinoma.

In certain embodiments, labeled anti-Notch2 or anti-Jag1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-Notch2 or anti-Jag1 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a chemotherapeutic agent or another therapeutic antibody with the anti-Notch2 or anti-Jag1 antibody. In some embodiments, a formulation may contain an anti-Notch2 antibody and an anti-Jag1 antibody. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Compositions

Also provided herein are article of manufacture is provided comprising (a) a container; (b) a composition of matter contained within the container comprising an anti-Notch2 antibody or an anti-Jagged1 antibody and a carrier for the treatment of liver cancer; and (c) a label affixed to the container, or a package insert included with the container, referring to the use of the composition of matter for the therapeutic treatment of or the diagnostic detection of a liver cancer.

Antibodies of the invention can be used either alone or in combination with other agents in a therapy. For instance, an antibody of the invention may be co-administered with at least one additional therapeutic agent. In certain embodiments, an additional therapeutic agent is a chemotherapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-Notch2 or Jag1 antibody and administration of an additional therapeutic agent occur within about one month, or within about one, two or three weeks, or within about one, two, three, four, five, or six days, of each other. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. For repeated administrations over several days or longer, depending on the condition, the treatment would generally be sustained until a desired suppression of disease symptoms occurs. An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-Notch2 or anti-Jag1 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. For example, an article of manufacture is provided comprising (a) a container; (b) a composition of matter contained within the container comprising an anti-Notch2 antibody or an anti-Jagged1 antibody and a carrier for the treatment of liver cancer; and (c) a label affixed to the container, or a package insert included with the container, referring to the use of the composition of matter for the therapeutic treatment of or the diagnostic detection of a liver cancer.

Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a Notch2 signaling inhibitor, e.g., an anti-Notch2 antibody or anti-Jag1 antibody. The label or package insert indicates that the composition is used for treating a proliferative disorder of the liver, such as liver cancer. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a proliferative disorder of the liver, such as liver cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-Notch2 or anti-Jag1 antibody.

III. Examples

The following are examples of methods and compositions of the invention. It is understood that various other embodiments may be practiced, given the general description provided above.

Example 1

Murine Model of Liver Cancer

FVB-N mice (Charles River, Hollister) were subjected to hydrodynamic tail vein injection of Ras, AKT, and Sleeping Beauty transposase encoding plasmids as previously described (Ho et al., C., Hepatology 55:833-845 (2012)). Briefly, 10 ug of pT3-CAGGS-NRasV12, Mug of pT3-EF1A-AKT, and 0.8 ug CMV-SB (Ho et al., Hepatology 55:833-845 (2012); Yant et al., Mol. Cell. Biol. 24:9239-9247 (2004)) were diluted in approximately 2 mL of Saline Solution (0.9% NaCl) and injected into the lateral tail vein of FVB-N mice in 5 to 8 seconds.

To model the development of liver cancer, mice were subjected to hydrodynamic tail vein injection of plasmids encoding oncogenic Ras and constitutively active AKT along with Sleeping Beauty transposase, as described above and as previously described (Ho et al., C., Hepatology 55:833-845 (2012)). This model allows for efficient and stable transfection of hepatocytes and reliable expression of the transfected oncogenes. Within 5 weeks following hydrodynamic tail vein injection, mice developed numerous intrahepatic tumor masses. Much of the normal liver parenchyma was displaced by tumor epithelium and livers of these mice expanded to as much as ten times their original size. Consistent with previous reports, the tumors that developed in these mice comprised a wide spectrum of liver tumor types, including hepatocellular carcinoma (HCC) and cholangiocarcinoma (CC). Approximately 80% of tumor nodules met the histopathological criteria for hepatocellular carcinoma and 20% met histopathological criteria for identification as cholangiocarcinoma.

Figure 1B:
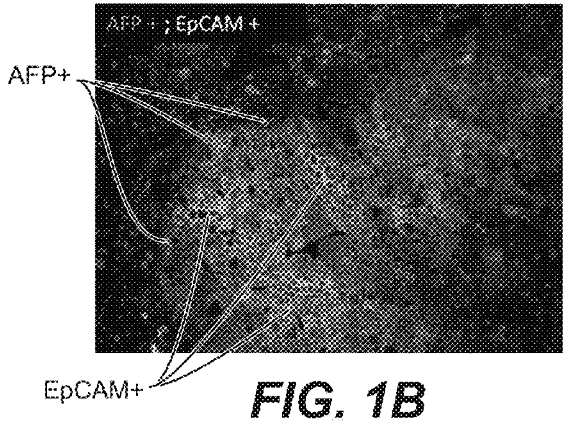
Figure 1C:
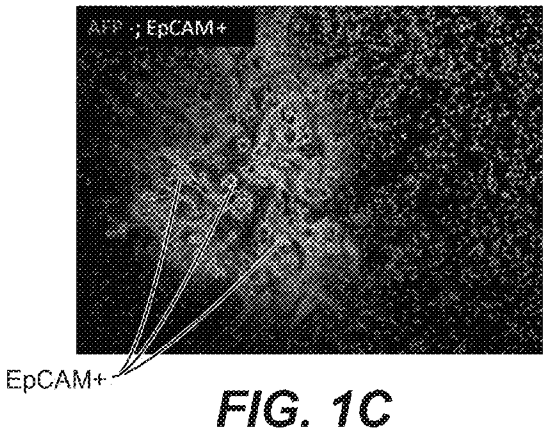

Each liver comprised dozens of tumors each of which expressed a given marker or combination of markers, such as AFP (FIG. 1A) and EpCAM (FIG. 1C). Some tumors express both AFP and EpCAM (FIG. 1B). Tumors in this model varied in their expression of HCC- and CC-specific tumor markers (FIG. 1A). Expression of alpha-Fetoprotein (AFP), specific for HCC, was detected in about 12.8% of cells in tumor-bearing livers (FIG. 1D), compared to less than 1% in normal non-tumor-bearing livers. Expression of EpCAM (FIG. 1B), a marker of cholangiocarcinoma, was less prevalent in this model, detected in an average of about 5% of all liver cells, compared to about 1% in normal non-tumor-bearing livers. Tumors expressing both HCC- and CC-specific markers were also observed (FIG. 1C). These combined HCC-CC (cHCC-CC) tumors are characterized by particularly aggressive clinical features (American-Cancer-Society. 2012. Cancer Facts & Figures. 2012. Atlanta: American Cancer Society) and share gene expression patterns with liver progenitor cells (Coulouarn et al., Carcinogenesis 33:1791-1796 (2012)).

Example 2

Activation of Notch2 Signaling

To determine if liver cancer is associated with Notch2 activation, immunofluorescence analysis was performed on tumors arising in the livers of AKT/Ras HTV mice. Liver tissues were embedded and frozen in O.C.T.™ freezing medium (TISSUE-TEK®), and cryosectioned at 8 μm. Sections were fixed in 4% paraformaldehyde (PFA) and stained using primary antibodies for Notch2 (Cell Signaling Technology), EpCAM (BioLegend), and AFP (R&D Systems). For image analysis, immunofluorescence-stained slides were scanned using an Ariol slide scanning system (Leica).

Figure 1F:
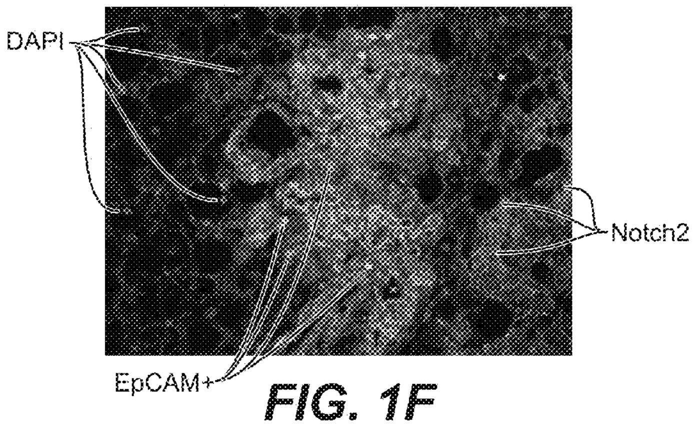
Figure 1E:
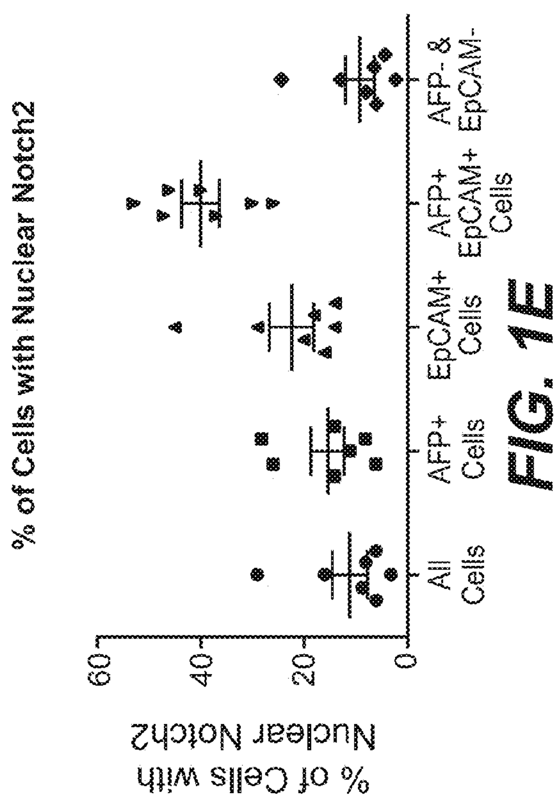
Figure 1D:
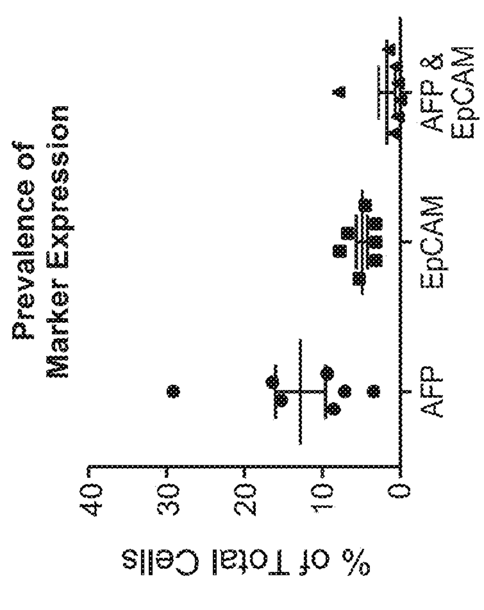

High levels of Notch2 activation, as determined by immunofluorescence detection of nuclear Notch2, was observed in $AFP^+$/$EpCAM^+$ tumors (FIG. 1E) and to a lesser extent in $EpCAM^+$ tumors (FIG. 1E, FIG. 1F). Less prominent staining for activated Notch2 was observed in other tumor cell types (FIG. 1E).

Example 3

Generation of Antibodies

To determine if Notch2 signaling was important for driving the development or growth of liver cancer, specifically in double positive tumors, mice were subjected to hydrodynamic tail vain injection with the AKT/Ras construct as described in Example 1, and treated with an anti-Notch2 antibody, anti-Jag1 antibody or isotype control (anti-Ragweed) antibody.

a. Library Sorting and Screening to Identify Anti-Jagged 1 Antibodies

Human phage antibody libraries with synthetic diversities in the selected complementarity determining regions, mimicking the natural diversity of human IgG repertoire, were used for panning Fab fragments displayed on the surface of M13 bacteriophage particles. Human Jag1-DSL-EGF1-4 (FIG. 10) was used as antigen for library sorting. Nunc 96 well Maxisorp immunoplates were coated overnight at 4° C. with target antigen (10 μg/ml) and were blocked for 1 hour at room temperature with phage blocking buffer PBST (phosphate-buffered saline (PBS) and 1% (w/v) bovine serum albumin (BSA) and 0.05% (v/v) tween-20). Antibody phage libraries VH (see, e.g., Lee et al., J. Immunol. Meth. 284:119-132, 2004) and VH/VL (see Liang et al., JMB. 366: 815-829, 2007) were added to antigen plates separately and incubated overnight at room temperature. The following day antigen-coated plates were washed ten times with PBT (PBS with 0.05% Tween-20), and bound phage were eluted with 50 mM HCl and 500 mM NaCl for 30 minutes and neutralized with an equal volume of 1 M Tris base (pH7.5). Recovered phages were amplified in *E. coli* XL-1 Blue cells. During the subsequent selection rounds, incubation of antibody phage with the antigen-coated plates was reduced to 2-3 hours, and the stringency of plate washing was gradually increased.

After 4 rounds of panning, significant enrichment was observed. 96 clones were picked each from VH and VH/VL library sorting to determine whether they specifically bound to human Jagged 1. The variable regions of these clones were PCR sequenced to identify unique sequence clones. The affinities of phage antibodies were ranked using spot competition ELISA. The phage antibody IC50 values were further determined using competitive phage-binding ELISA. Unique phage antibodies that bind specifically to human Jagged 1 (and not Jagged 2), or to both Jagged 1 and Jagged 2 were chosen and reformatted to full-length IgGs for evaluation in in vitro cell assays.

Clones of interest were reformatted into IgGs by cloning $V_L$ and $V_H$ regions of individual clones into a pRK mammalian cell expression vector (pRK.LPG3.HumanKappa) containing the human kappa constant domain, and expression vector (pRK.LPG4.HumanHC) encoding the full-length human IgG1 constant domain, respectively (Shields et al., *J Biol Chem* 2000; 276: 6591-6604). The antibodies were then transiently expressed in mammalian CHO cells, and purified with a protein A column.

b. Construction of Libraries for Affinity Improvement of Clones Derived from the $V_H$ or $V_HV_L$ Libraries Phagemid pW0703, derived from phagemid pV0350-2b (Lee et al., *J. Mol. Biol.* 340, 1073-1093 (2004), containing stop codon (TAA) in all CDR-L3 positions and displaying monovalent Fab on the surface of M13 bacteriophage) served as the library templates for grafting heavy chain variable domains ($V_H$) of clones of interest from the $V_H$ library for affinity maturation. Both hard and soft randomization strategies were used for affinity maturation. For hard randomization, one light chain library with selected positions of the three light chain CDRs was randomized using amino acids designed to mimic natural human antibodies and the designed DNA degeneracy was as described in Lee et al. (*J. Mol. Biol.* 340, 1073-1093 (2004)). To achieve the soft randomization conditions, which introduced the mutation rate of approximately 50% at the selected positions, the mutagenic DNA was synthesized with 70-10-10-10 mixtures of bases favoring the wild type nucleotides (Gallop et al., *J. Med. Chem.* 37:1233-1251 (1994)). For soft randomization, residues at positions 91-96 of CDR-L3, 30-33, 35 of CDR-H1, 50, 52, 53-54, and 56 of CDR-H2, 95-98 of CDR-H3 were targeted; and three different combinations of CDR loops, H1/L3, H2/L3, and H3/L3, were selected for randomization.

For clones originated from $V_HV_L$ library, phagemids containing 4 stop codons (TAA) in each CDR and displaying monovalent Fab on the surface of M13 bacteriophage were generated individually, and served as the templates for kunkel mutagenesis for the construction of affinity maturation libraries. Only soft randomization strategy was used for clones derived from $V_HV_L$ library, as diversity of CDR-L3 was built into the naïve library. To achieve the soft randomization conditions, residues at positions 28-31 of CDR-L1, 50, 53-55 of CDR-L2, 91-96 of CDR-L3, 30-35 of CDR-H1, 50-56 of CDR-H2, 95-100 of CDR-H3 were targeted; and four different combinations of CDR loops, H1/L3*, H2/L3*, and H3/L3* and L1/L2/L3* (where * denotes the position of stop codons on the template), were selected for randomization.

c. Phage Sorting Strategy to Generate Affinity Improvement

For affinity improvement selection, Jag1 antigens were first biotinylated under limiting reagent condition. Phage libraries were subjected to one round of plate sorting and five rounds of solution sorting with increasing stringency. For the first round of plate sorting, 10 ug/ml antigen was first coated on Maxisorp plate and preblocked with blocking buffer (1% BSA and 0.05% Tween20 in PBS). 3 O.D./ml in blocking buffer of phage input were incubated to antigen plates for 3 hours. The wells were washed with PBS-0.05% Tween20 ten times. Bound phage was eluted with 150 ul/well 50 mM HCl, 500 mM KCl for 30 minutes, and subsequently neutralized by 50 ul/well of 1M Tris pH8, titered, and propagated for the next round. For subsequent rounds, panning of the phage libraries was done in solution phase, where phage library was incubated with 100 nM biotinylated target protein (the concentration is based on parental clone phage IC50 value) in 100 ul buffer containing 1% Superblock (Pierce Biotechnology) and 0.05% Tween20 for 2 hours at room temperature. The mixture was further diluted 10× with 1% Superblock, and 100 μl/well was applied to neutravidin-coated wells (10 μg/ml) for 30 minutes at room temperature with gentle shaking. To determine background binding, control wells containing phage were captured on neutravidin-coated plates. Bound phage was then washed, eluted and propagated as described for first round. Five more rounds of solution sorting were carried out together with increasing selection stringency. The first couple rounds of which is for on-rate selection by decreasing biotinylated target protein concentration from 100 nM to 0.1 nM, and the last two rounds of which is for off-rate selection by adding excess amounts of non-biotinylated target protein (300 to 1000 fold more) to compete off weaker binders at room temperature.

d. High Throughput Affinity Screening ELISA (Single Spot Competition)

Colonies were picked from the sixth round of screening. Colonies were grown overnight at 37° C. in 150 μl/well of 2YT media with 50 μg/ml carbenicillin and $1\times10^{10}$/ml M13KO7 in 96-well plate (Falcon). From the same plate, a colony of XL-1 infected parental phage was picked as control. 96-well Nunc Maxisorp plates were coated with 100 μl/well of either Jag1 or Jag2 (0.5 μg/ml) in PBS at 4° C. overnight. The plates were blocked with 150 μl of 1% BSA and 0.05% Tween20 in PBS 20 for 1 hour.

35 μl of the phage supernatant was diluted with 75 μl of ELISA (enzyme linked immunosorbent assay) buffer (PBS with 0.5% BSA, 0.05% Tween20) with or without 5 nM Jag1 or Jag2 and let incubate for 1 hour at room temperature in an F plate (NUNC). 95 μl of mixture was transferred side by side to the antigen coated plates. The plate was gently shaken for 15 min and was washed ten times with PBS-0.05% Tween 20. The binding was quantified by adding horseradish peroxidase (HRP)-conjugated anti-M13 antibody in ELISA buffer (1:2500) and incubated for 30 minutes at room temperature. The plates were washed with PBS-0.05% Tween 20 ten times. Next, 100 μl/well of Peroxidase substrate was added to the well and incubated for 5 minutes at room temperature. The reaction was stopped by adding 100 μl d 0.1M Phosphoric Acid ($H_3PO_4$) to each well and allowed to incubate for 5 minutes at room temperature. The O.D. (optical density) of the yellow color in each well was determined using a standard ELISA plate reader at 450 nm. In comparison to the $OD_{450\ nm}$ reduction (%) of the well of parental phage (100%), clones that had the $OD_{450\ nm}$ reduction (%) lower than 50% were picked for sequence analysis. Unique clones were selected for phage preparation to determine binding affinity (phage IC50) against Jag1 by comparison to respective parental clones. Then the most affinity-improved clones were reformatted into human IgG1 for antibody production.

Parent antibody A and affinity matured antibodies A-1 and A-2 specifically bound to human and murine Jag1, specifically, to Jag1 DSL-EGF1-4, but not human or murine Jag 2.

The generation and characterization of certain anti-Notch2 NRR antibodies have been previously described. See PCT Application No. PCT/US09/059,028.

Example 4

Treatment with Notch2 Signaling Inhibitor Reduces Tumor Burden

Figure 2A:
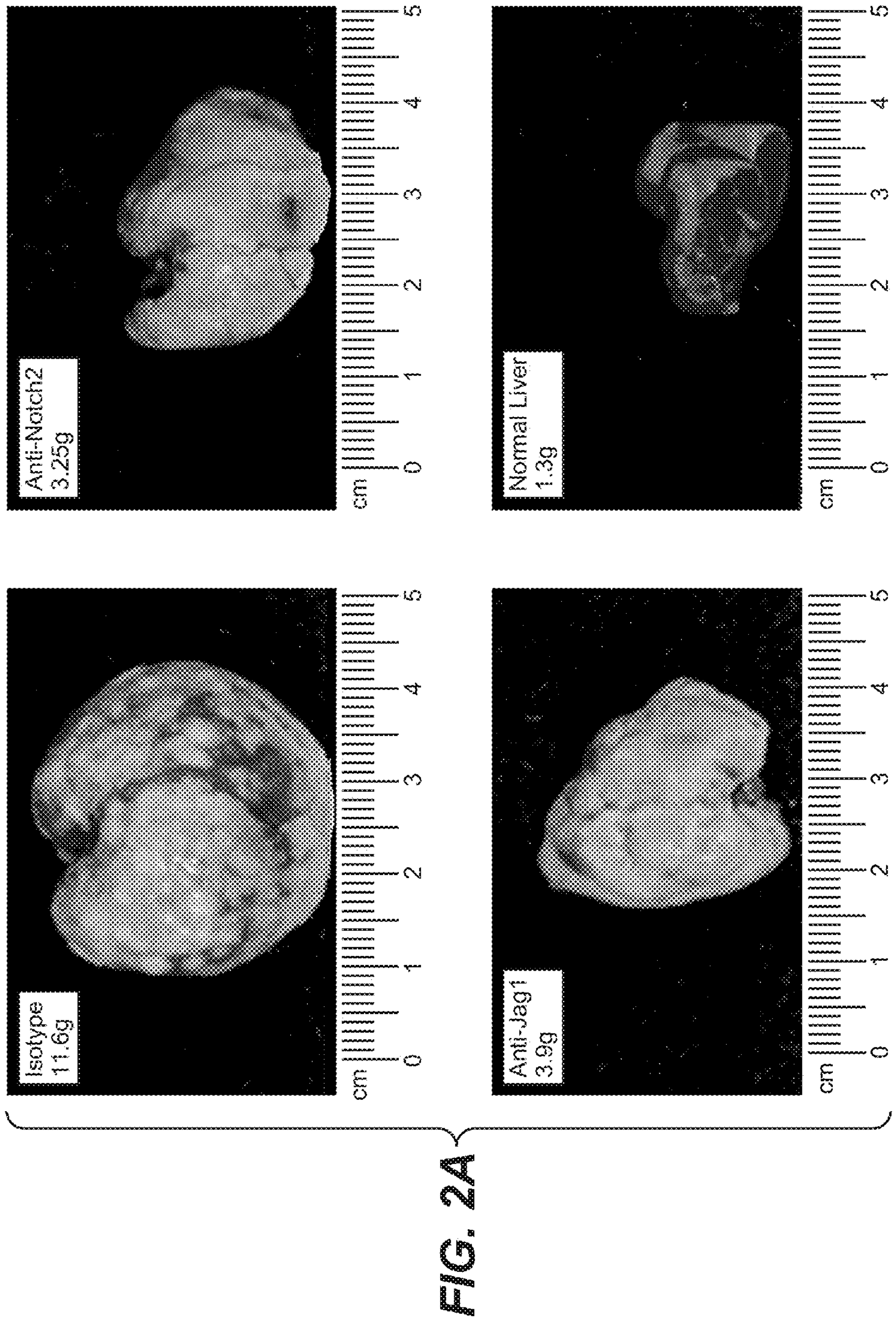
FIGS. 2A-D illustrate reduced tumor burden in Ras/AKT HTV mice treated with anti-Notch2 or anti-Jag1 antagonist antibodies.
Figure 2B:
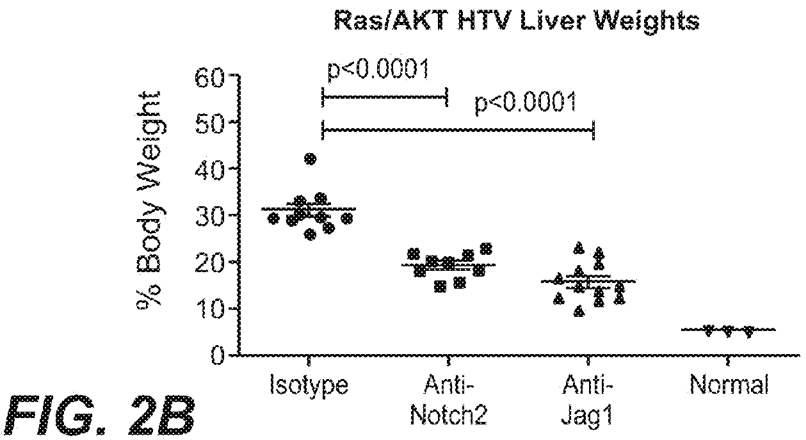
Figure 2C:
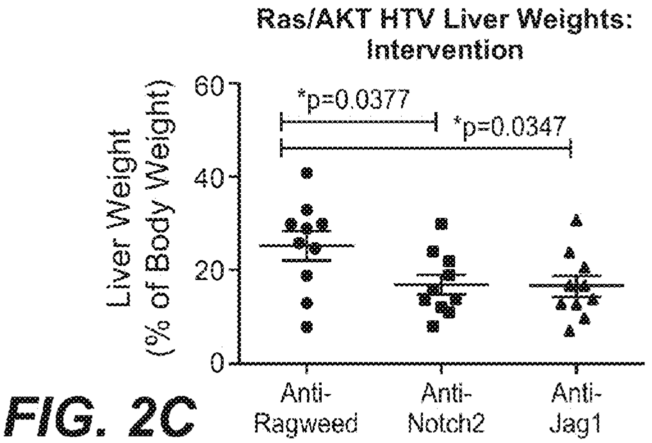

AKT/Ras HTV mice as described in Example 1 were treated with an anti-Notch2 antibody (15 mg/kg, 1×/week), anti-Jag1 antibody (10 mg/kg, 1×/week) or isotype control antibody beginning the day of the hydrodynamic tail vain injection. Livers were imaged and weighed at necropsy on a standard laboratory balance. Mice treated with the control antibody developed a heavy tumor burden (FIG. 2A) five weeks following hydrodynamic tail vain injection, with their livers increasing in size to about 8.9 g or approximately 31% of body weight, up from 1.2 g or 5.8% of body weight (FIG. 2B) in normal, non-tumor-bearing mice. Treatment with either anti-Notch2 or anti-Jag1 antibody significantly impeded tumor development (FIGS. 2A and B; $p<0.0001$, $n>8$). Mice treated with anti-Notch2 antibody developed a significantly smaller tumor burden with their livers growing to an average of 5.1 g or 19.3% of body weight (FIG. 2B). Anti-Jag1 treatment had an even greater effect. In these mice final liver weights averaged 4.3 g or 15.8% of body weight (FIG. 2B).

Figure 3A:
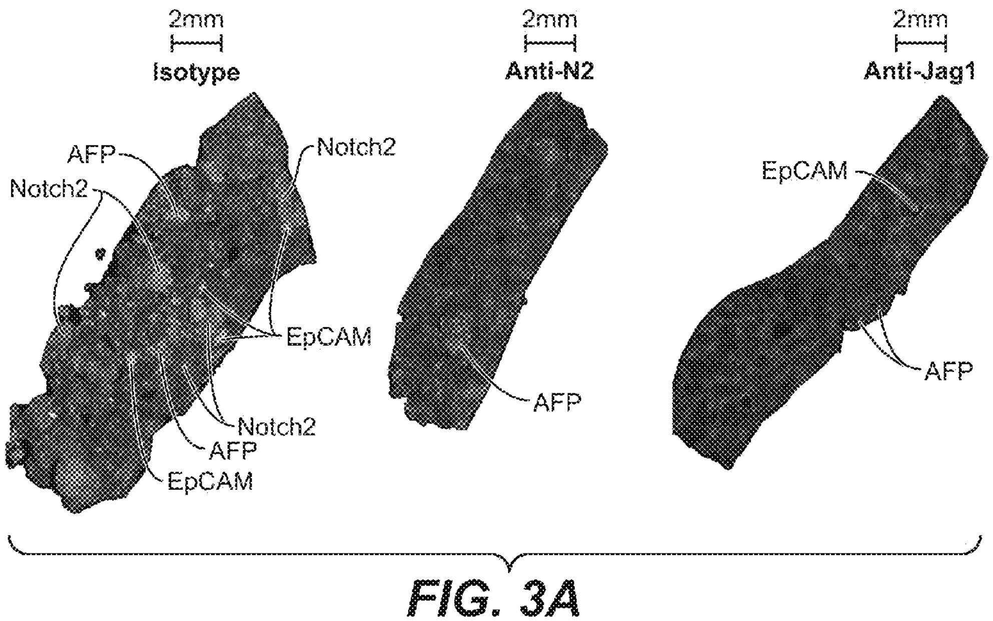
FIGS. 3A-H illustrate treatment of AKT/Ras HTV tumor-bearing mice with Notch inhibitory antibodies impedes the development of a broad range of tumor types.
Figure 3D:
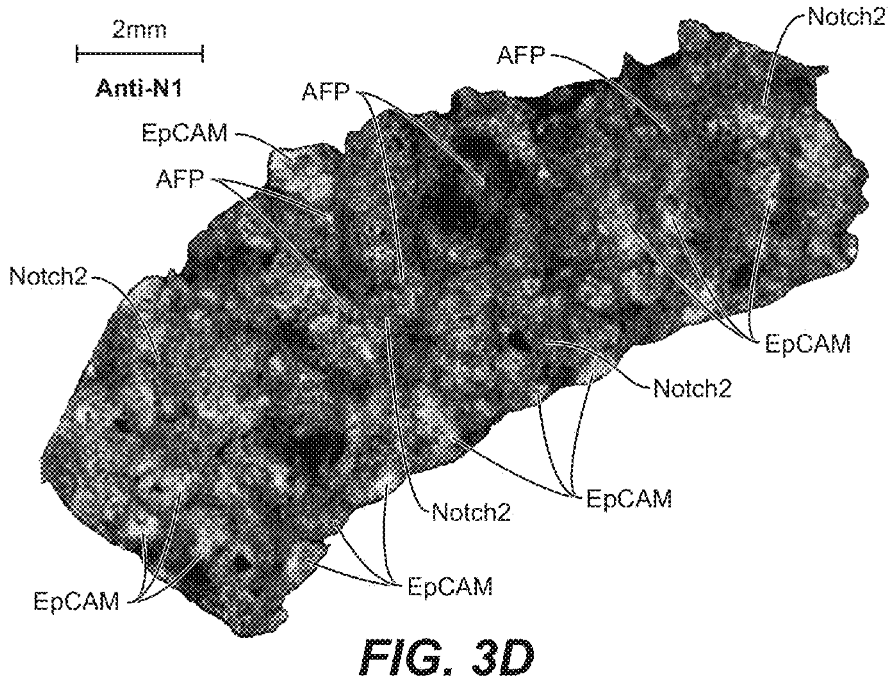
Figure 3B:
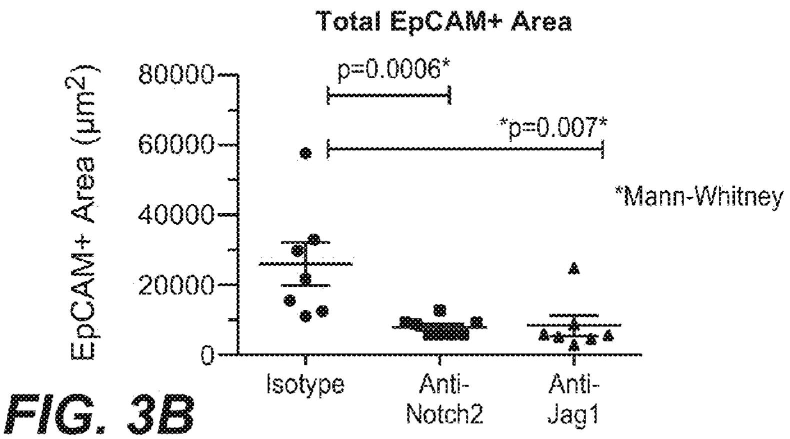
Figure 3C:
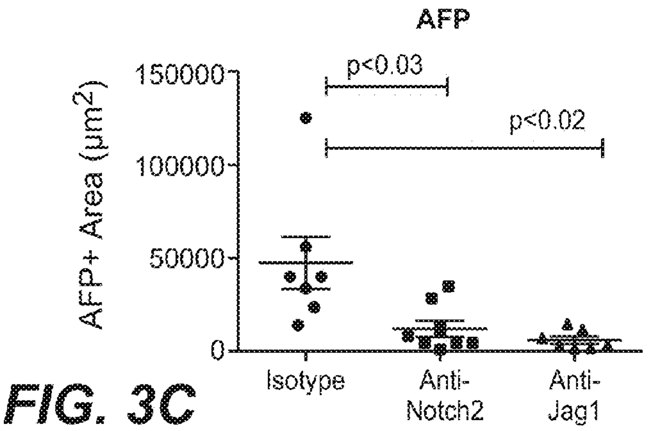

$EpCAM^+$ and $AFP^+/EpCAM^+$ subsets of tumors (FIG. 1E), in which Notch2 signaling was more highly activated than in $EpCAM^-$ tumors as determined by detection of nuclear Notch2 by immunofluorescence, were highly susceptible to Notch2 pathway inhibition. $EpCAM^+$ tumors ($AFP^-/EpCAM^+$ and $AFP^+/EpCAM^+$ tumors) were significantly reduced in area following treatment with either anti-Notch2 antibody or anti-Jag1 antibody (FIG. 3A, FIG. 3B). Notch2 signaling was not as highly activated in $AFP^+/EpCAM^-$ tumors (FIG. 1E), suggesting that these tumors might not be affected by Notch2 pathway inhibition. However, contrary to expectation, both anti-Notch2 treatment and anti-Jag1 treatment led to significant reduction in $AFP^+$ tumor area (FIG. 3C). Taken together, these results demonstrate that anti-Notch2 or anti-Jag1 antibody treatment blocks the development of a broad range of liver tumors in this model of liver cancer. Successful treatment with anti-Notch2 and anti-Jag1 antibodies resulted in reduction of overall tumor burden including both HCC-like and cholangiocarcinoma-like tumors as indicated by significant reductions in AFP and EpCAM staining following anti-Notch2 and anti-Jag1 antibody treatment.

Example 5

Inhibition of Notch1 and Notch3

Figure 2D:
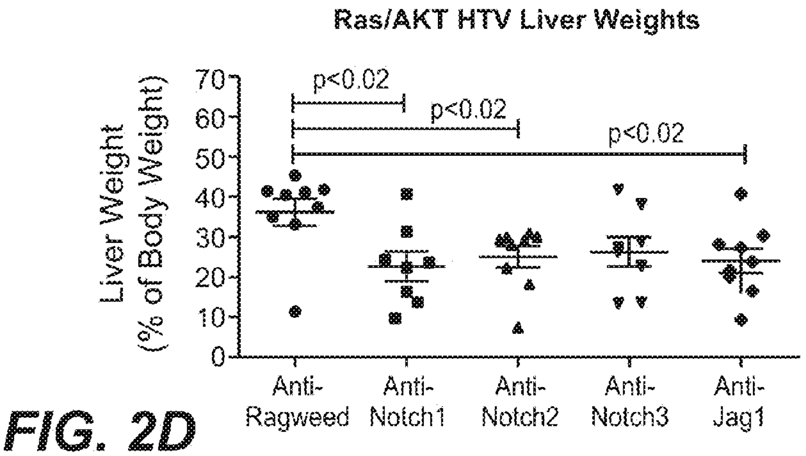
Figure 3E:
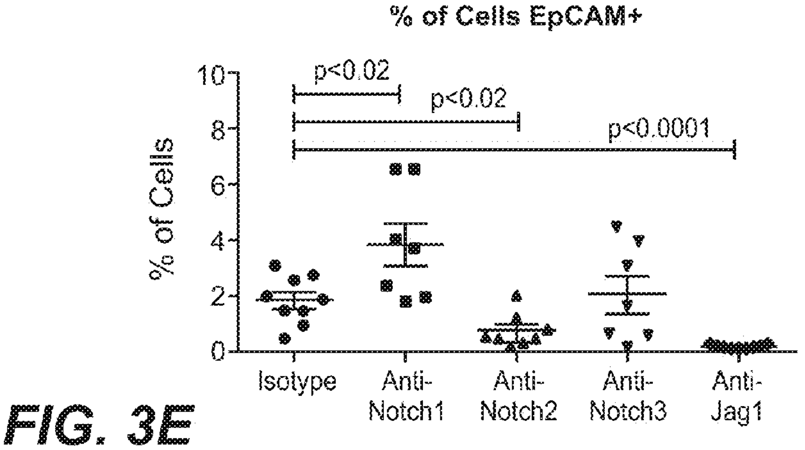
Figure 3F:
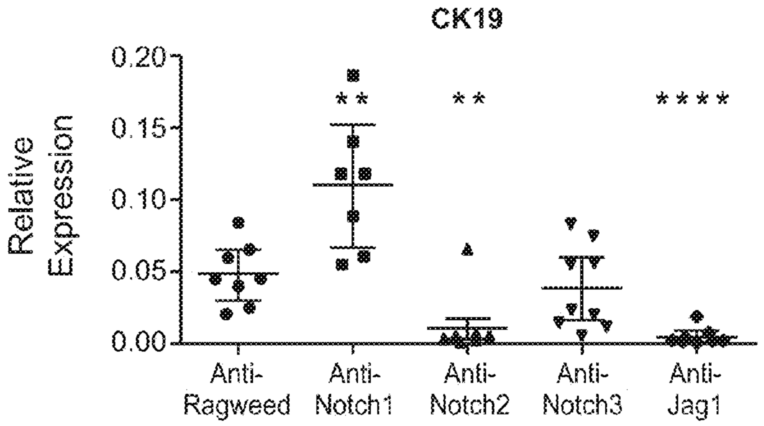
Figure 3G:
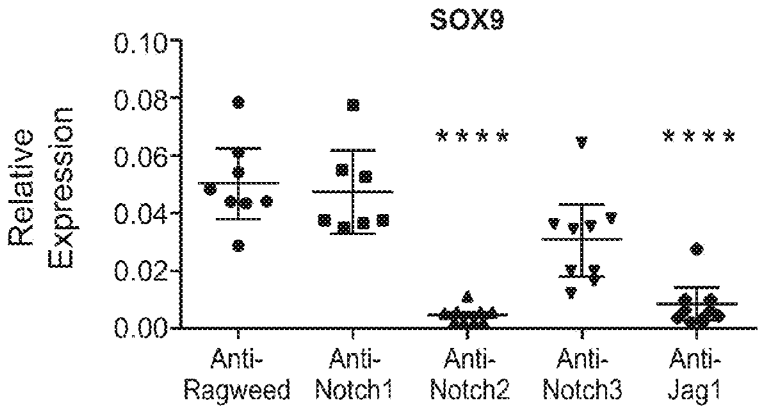
Figure 3H:
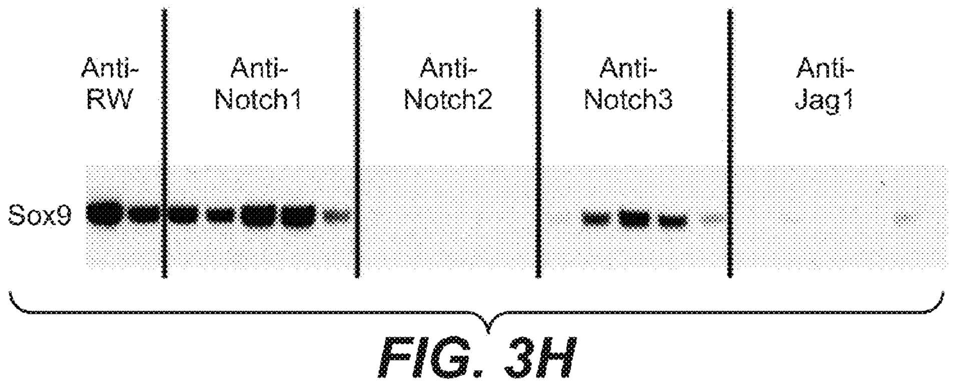

Inhibition of Jag1 had a similar effect as inhibition of Notch2, suggesting that Jag1 and Notch2 are acting in the same pathway, specifically, that Jag1 acts as the ligand for Notch2 in supporting tumor formation. To determine if inhibition of other Notch receptors could also reduce liver cancer formation or growth, mice were subjected to hydrodynamic tail vain injection with the Ras/AKT construct as described in Example 1 and treated with an anti-Notch1 antagonist antibody (10 mg/kg, 1×/week) or an anti-Notch3 antagonist antibody (30 mg/kg, 3×/week). Treatment with the anti-Notch1 antibody reduced liver weight in Ras/AKT HTV mice, compared to isotype controls, while treatment with an anti-Notch3 antibody did not significantly affect liver weight (FIG. 2D; $p<0.02$, $n\geq7$). While anti-Notch2 or anti-Jag1 treatment decreased the level of EpCAM transcript (FIG. 3E, $p<0.005$, $n\geq7$), inhibition of Notch1 increased the cross-sectional area of EpCAM positive tumors in the liver (FIG. 3D, FIG. 3E, $p<0.02$, $n \geq 7$) and increased the expression of the cholangiocarcinoma marker Cytokeratin 19 (CK19; FIG. 3F). Treatment with antagonist antibodies to anti-Notch1 or anti-Notch3 did not affect expression of Sox9, a liver progenitor cell and progenitor cell-like tumor marker and cholangiocarcinoma-like tumor marker, while treatment with an anti-Notch2 or anti-Jag1 antibody drastically decreased Sox9 at both the mRNA (FIG. 3G) and protein level (FIG. 3H).

Thus, treatment with anti-Notch1 or anti-Notch3 antibodies did not significantly decrease tumor burden. In fact, inhibition of Notch1 caused an increase in the number and cross-sectional area occupied by $EpCAM^+$ cholangiocarcinoma-like tumors. These results, taken together with the observation of increased cholangiocarcinoma-like lesions following anti-Notch1 treatment, further supported the conclusion that there are opposing roles for Notch2 and Notch1 in liver cancer.

Example 6

Anti-Notch2 or Anti-Jag1 Antibody Treatment Reduces Notch2 Activation

For immunohistochemical analysis, tissues were fixed in 10% Neutral Buffered Formalin, embedded in paraffin, and sectioned. 4 μm-thick formalin-fixed paraffin embedded human tissues were subject to staining. For Jag1 IHC staining, all steps were carried out on the Ventana Discovery XT autostainer using Ventana detection reagents (Ventana Medical Systems, Tucson, Ariz.). Tissue sections were deparaffinized in EZPrep solution and pretreatment was done with Cell Conditioner 1 using standard incubation time. Tissue sections were then incubated with goat polyclonal anti-Jag1 primary antibody (Santa Cruz Biotechnology Inc, Santa Cruz, Calif.; Cat# sc-6011) at 0.2 μg/ml for 32 minutes at room temperature followed by incubation with biotinylated rabbit anti-goat IgG antibody (Vector Labs, Burlingame, Calif.) at 7.5 μg/ml for 32 minutes at room temperature. Both primary and secondary antibodies were diluted in 10% normal human serum (Jackson ImmunoResearch) in 3% BSA. The sections were subsequently incubated with anti-Rabbit OmniMAP-HRP reagent for 16 minutes at room temperature.

For Notch 2 IHC, all steps were carried out on the Ventana Discovery XT Platform utilizing Ventana detection reagents (Ventana Medical Systems, Tuscon, Ariz.). Sections were deparaffinized using EZ Prep and pretreatment was accomplished with Cell Conditioner 1 using standard incubation time. Sections were then incubated with rabbit monoclonal anti-Notch2 primary antibody (Clone D76A6, Cell Signaling Technologies, Beverley, Mass.) at 8 μg/ml for 60 minutes at 37° C., followed by incubation with anti-Rabbit OMNI-MAP-HRP reagent for 32 minutes.

For Hes1, all steps were carried out on the Dako autostainer using DAKO wash buffer and DAKO Target Retrieval Solution. Sections were deparaffinized, re-hydrated then incubated with DAKO Target Retrieval Solution at 99° C. for 20 min, quenched with 3% H2O2 for 4 minutes then blocked with Avidin Biotin Blocking Kit (Vector Laboratories: cat# sp-2001). Sections were incubated 45 min at RT with 1 ug/ml anti-HES-1 (clone NM1; MBL International) then 5 ug/ml secondary antibody Bt-Dk anti-Rat (JacksonImmunoResearch) 15 minutes followed by Biotinylated-Tyramide (1:50) in amplification diluent for 3 minutes. Sections were subsequently incubated with DAB and Hematoxylin II reagents for chromogenic detection and counterstaining. Slides were dehydrated, cleared in xylenes and coverslipped. All Sections were subsequently incubated with DAB and Hematoxylin II reagents for chromogenic detection and counterstaining. Slides were dehydrated, cleared in xylenes and coverslipped. For image analysis, immunohistochemistry slides were scanned using the Nanozoomer slide scanning system (Hamamatsu).

Quantitative real-time PCR (QRTPCR) was performed using the TaqMan One-Step RT-PCR Kit for one step reactions using the 7900 HT RT-PCR system (Applied Biosystems) with TaqMan probes (Applied Biosystems). Probes used were Notch1 (Mm00435245_m1, Hs01062014_m1), Notch2 (Mm00803077_m1, Hs01050719_m1), Notch3 (Mm00435270_m1, Hs01128541_m1), Notch4 (Mm00440525), Jag1 (Mm00496902_m1), Jag2 (Mm01325629_m1), DLL1 (Mm01279269_m1), DLL3 (Mm00432854_m1), DLL4 (Mm00444619), Hey1 (Mm00516555_m1), CK19 (Mm00492980_m1) and Sox9 (Mm00448840_m1).

Figure 4A:
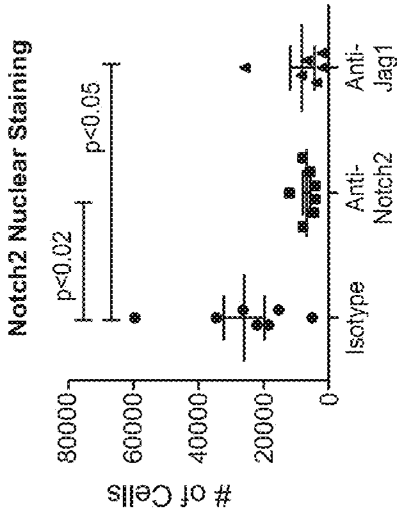
FIGS. 4A-E illustrate that treatment of AKT/Ras HTV mice with Notch inhibitory antibodies reduces Notch pathway activation in tumor-bearing livers.
Figure 4B:
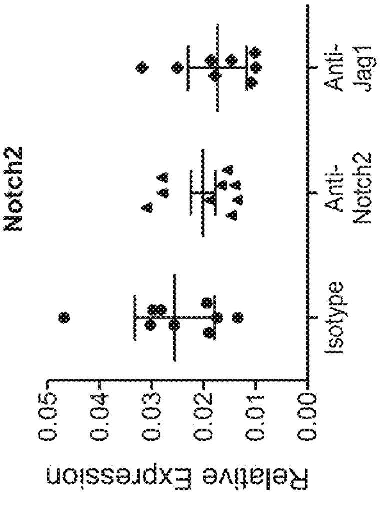
Figure 4C:
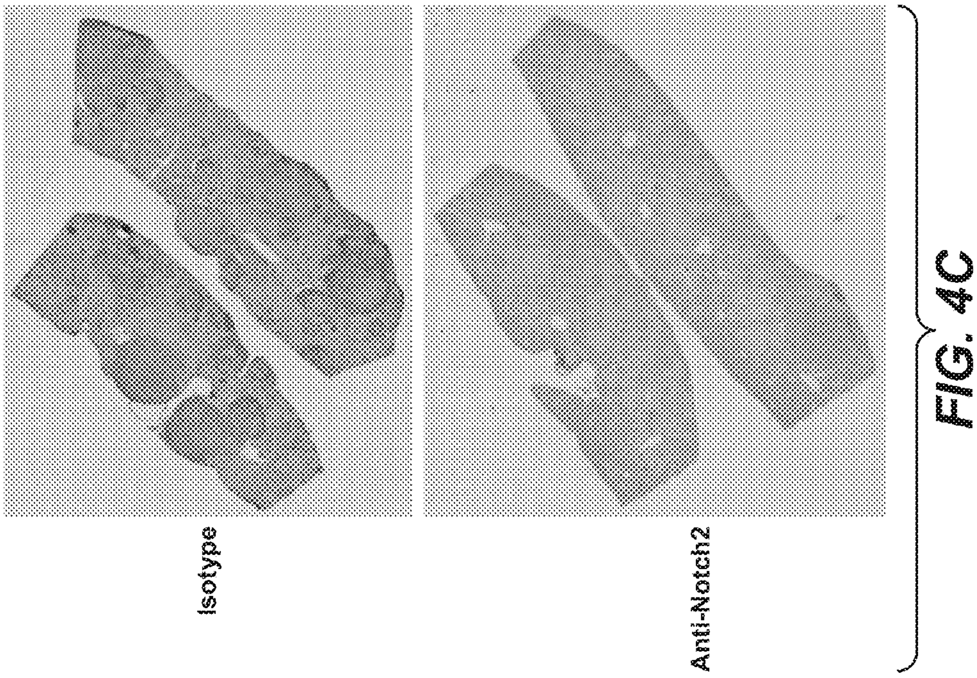
Figure 4D:
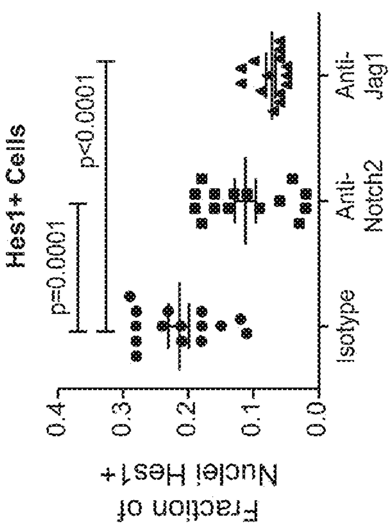
Figure 4E:
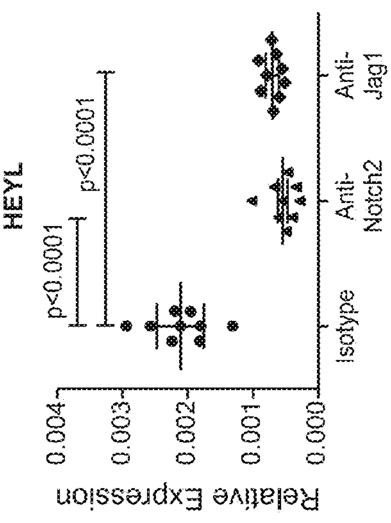

In keeping with the broader effect of Notch2 and Jag1 inhibition on tumor formation, Notch2 signaling, as determined by detection of nuclear Notch2 protein by immunofluorescence, was significantly reduced throughout the tumor-bearing livers following treatment with either anti-Notch2 or anti-Jag1 (FIG. 4A; $p<0.05$, $n \geq 7$). This reduction appeared to be due to a direct effect on activation of the Notch2 protein, as overall levels of Notch2 expression, as determined by quantitative RT-PCR, did not change. Consistent with anti-Notch2 or anti-Jag1 antibody treatment blocking Notch2 activation, immunostaining was reduced for Hes1, a downstream transcriptional target of the Notch2 signaling pathway. Control-treated Ras/AKT HTV livers showed high levels of Hes1 staining in (FIG. 4D). However, treatment with anti-Notch2 or anti-Jag1 antibody significantly reduced Hes1 staining, consistent with effective blockade of Notch2 signaling in the antibody-treated livers (FIG. 4C, FIG. 4D, $p \leq 0.0001$, $n>10$). Confirming that Notch2 signaling was blocked, quantitative RT-PCR analysis revealed that the Notch pathway target gene HeyL was also strongly decreased with either anti-Notch2 or anti-Jag1 antibody treatment (FIG. 4E, $p<0.0001$, $n>7$).

In each case, anti-Jag1 antibody treatment had the same effect as anti-Notch2 antibody treatment, further supporting the conclusion that Jag1 is acting primarily through, i.e. as a ligand for, Notch2 in supporting liver cancer formation and growth. Taken together, these results demonstrate that treatment with either anti-Notch2 or anti-Jag1 antibody resulted in a reduction of Notch2 activation.

Example 7

Effect of Notch Inhibitory Antibodies on Expression of Notch Signaling Pathway Components Mice subjected to AKT/Ras HTV were treated with antagonistic antibodies to Notch1 (10 mg/kg, 1×/week), Notch2 (10 mg/kg, 2×/week), Notch3 (30 mg/kg, 3×/week), or Jag1 (10 mg/kg, 1×/week). An anti-Ragweed antibody was administered at 30 mg/kg, 3×/week as a negative control. After 5 weeks, livers were harvested and quantitative real-time PCR was performed on the isolated RNA to determine the effect of treatment on transcripts of Notch signaling pathway components Inhibition of individual Notch family receptors did not lead to a compensatory increase in the expression of other Notch receptor family members.

Figure 5A:
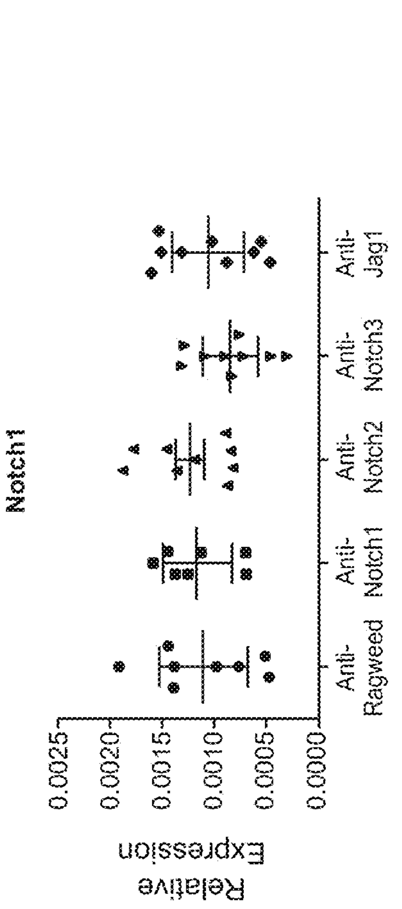
FIGS. 5A-I illustrate the effect of Notch inhibitory antibodies on expression of Notch signaling pathway components in the AKT/Ras model of liver cancer. Mice subjected to AKT/Ras HTV were treated with antagonistic antibodies to Notch1, Notch2, Notch3, or Jag1, or an anti-Ragweed negative control antibody and quantitative real-time PCR was performed on the isolated RNA from livers after 5 weeks for Notch1 (FIG. 5A), Notch2 (FIG. 5B), Notch3 (FIG. 5C), Notch4 (FIG. 5D), Jag1 (FIG. 5E), Jag2 (FIG. 5F), DLL1 (FIG. 5G), DLL3 (FIG. 5H), DLL4 (FIG. 5I).
Figure 5B:
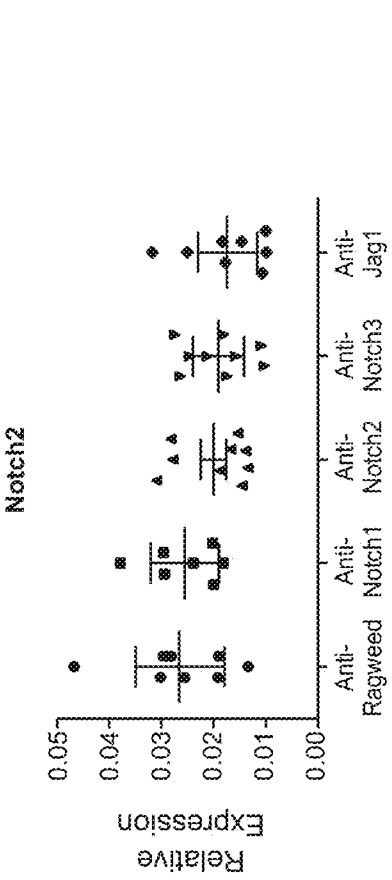
Figure 5C:
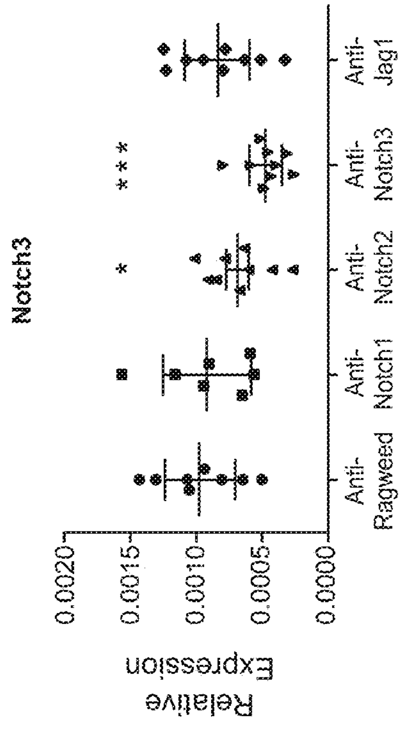
Figure 5D:
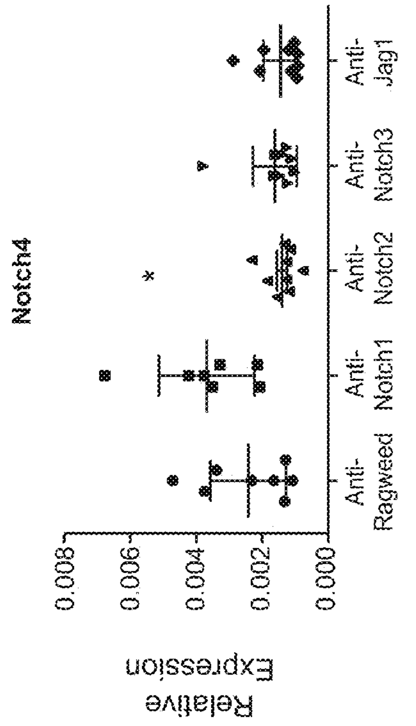
Figure 5E:
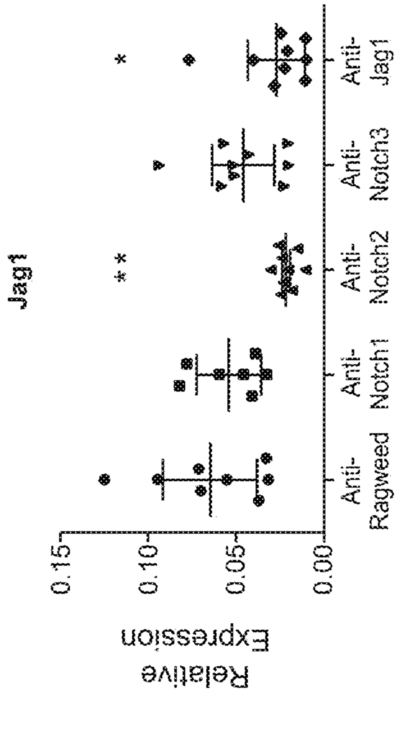
Figure 5F:
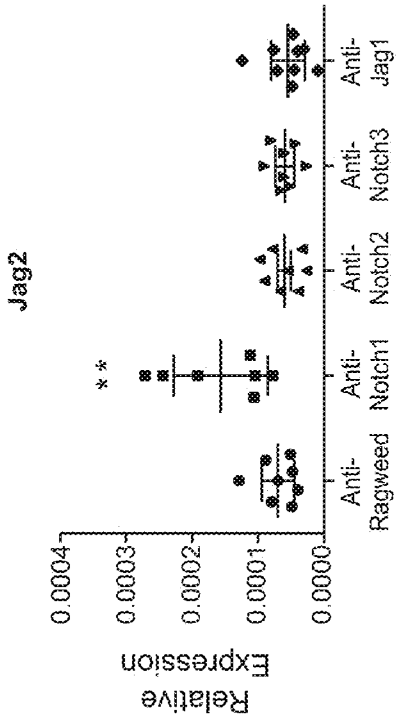
Figure 5G:
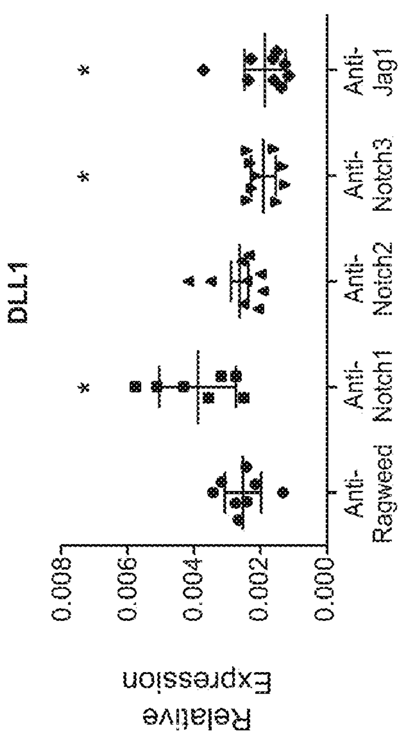
Figure 5H:
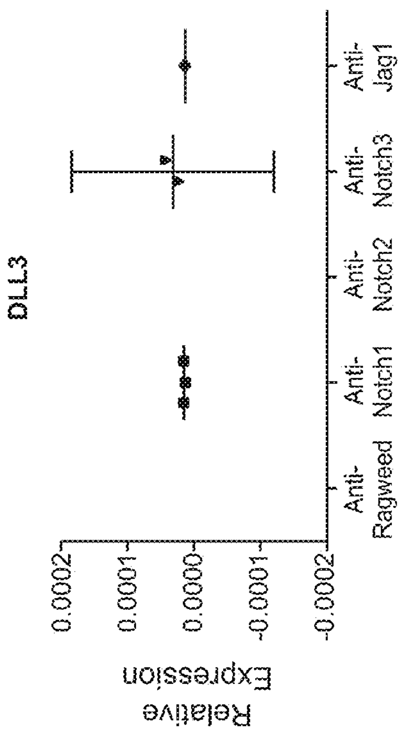
Figure 5I:
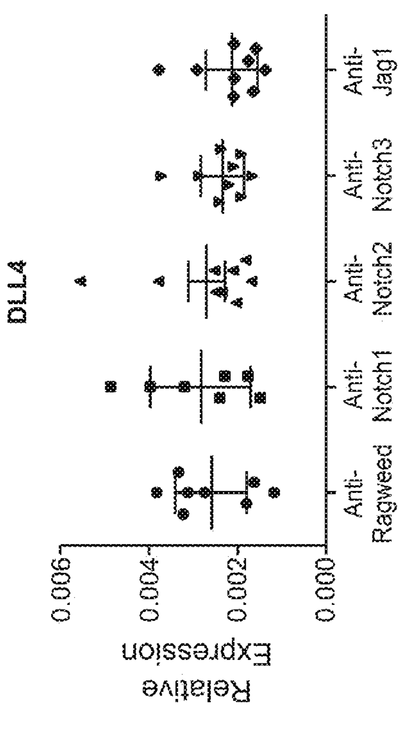

As described above, inhibition of individual Notch receptors, Notch1, Notch2, and Notch3, had distinct effects in the AKT/Ras model of liver tumor development. This result suggests that the individual Notch receptors do not necessarily compensate for one another in liver cancer. To determine the effect of inhibition of individual Notch receptors and ligands on expression of Notch receptor family members, expression was assessed following treatment of mice injection with the AKT/Ras construct as described in Example 1 with either an anti-Notch1, anti-Notch2, anti-Notch3, anti-Jag1 antibody or isotype control antibody. No increase in receptor transcript expression for any of the individual Notch receptors was observed upon inhibition with any of the three inhibitory antibodies (FIG. 5A-C). On the contrary Notch2 inhibition with a specific inhibitory antibody led to a significant decrease in expression levels of both Notch3 and Notch4 ($p<0.05$, $n\geq7$). Inhibition of Notch3 also led to a decrease in its own expression ($p<0.005$, $n\geq7$). This is consistent with previous observations that both Notch2 and Notch3 control the transcription of Notch3 (Wang et al., PLoS ONE 7:e37365 (2012); Liu et al., Circulation Research 107:860-870 (2010)). The effect of treatment with the antagonist antibodies was even greater with respect to expression of Notch ligands Jag1 and DLL1. Notch2 inhibition led to a significant decrease in Jag1 expression (FIG. 5E), likely as a result of the decrease in Jag1-expressing cholangiocarcinoma and progenitor-like tumors in these livers. Jag1 inhibition had a similar effect, further confirming that Jag1 and Notch2 are acting together in this tumor model. In contrast inhibition of Notch1 significantly increased the expression of the Notch ligands Jag2 and DLL1 (FIG. 5F, FIG. 5G). This result might, at least in part, help to explain the observed increase in cholangiocarcinoma-like lesions in livers treated with an anti-Notch1 antagonist antibody.

In summary, a compensatory increase in expression of other Notch receptors upon Notch2 inhibition was not observed, suggesting that successful treatment with anti-Notch2 or anti-Jag1 antibodies will not lead to resistance through upregulation of alternative Notch signaling components. In fact, treatment with either Notch2 or Jag1 antagonist antibodies actually led to a decrease in Jag1 ligand expression, and treatment with anti-Notch2 led to a decrease in Notch3 expression.

Example 8

Anti-Notch2 or Anti-Jag1 Antibody Treatment Blocks Progenitor-Like and Cholangiocarcinoma-Like Liver Tumor Growth To address the mechanisms by which Notch2 inhibition is leading to decreased tumor burden, high throughput RNA sequencing analysis was performed. Mice subjected to AKT/Ras HTV were treated with antagonistic antibodies to Notch2 (10 mg/kg, 2×/week), Jag1 (10 mg/kg, 1×/week), or anti-Ragweed control (30 mg/kg, 3×/week). After 5 weeks, livers were harvested and RNA was subjected to high-throughput sequencing.

Figure 6A:
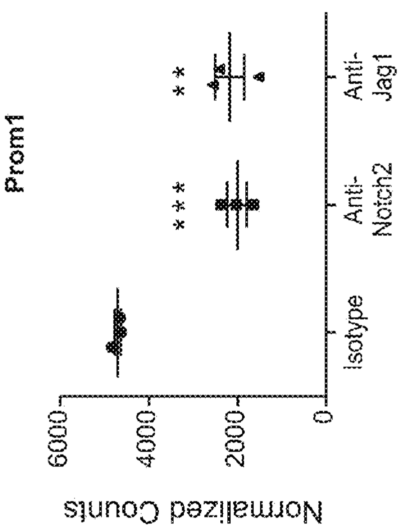
FIGS. 6A-I illustrate results from RNAseq analysis of livers from AKT/Ras HTV mice treated with isotype control, anti-Notch2 or anti-Jag1 antibody. Depicted are normalized counts for Prom1 (FIG. 6A), Spp1 (FIG. 6B), FoxM1 (FIG. 6C), Plk1 (FIG. 6D), ccnb1 (FIG. 6E), Aurkb (FIG. 6F), Wnt2 (FIG. 6G), Axin2 (FIG. 6H) and glutamine synthetase (Glul, FIG. 6I).
Figures 6B, 6C, 6D, 6E:
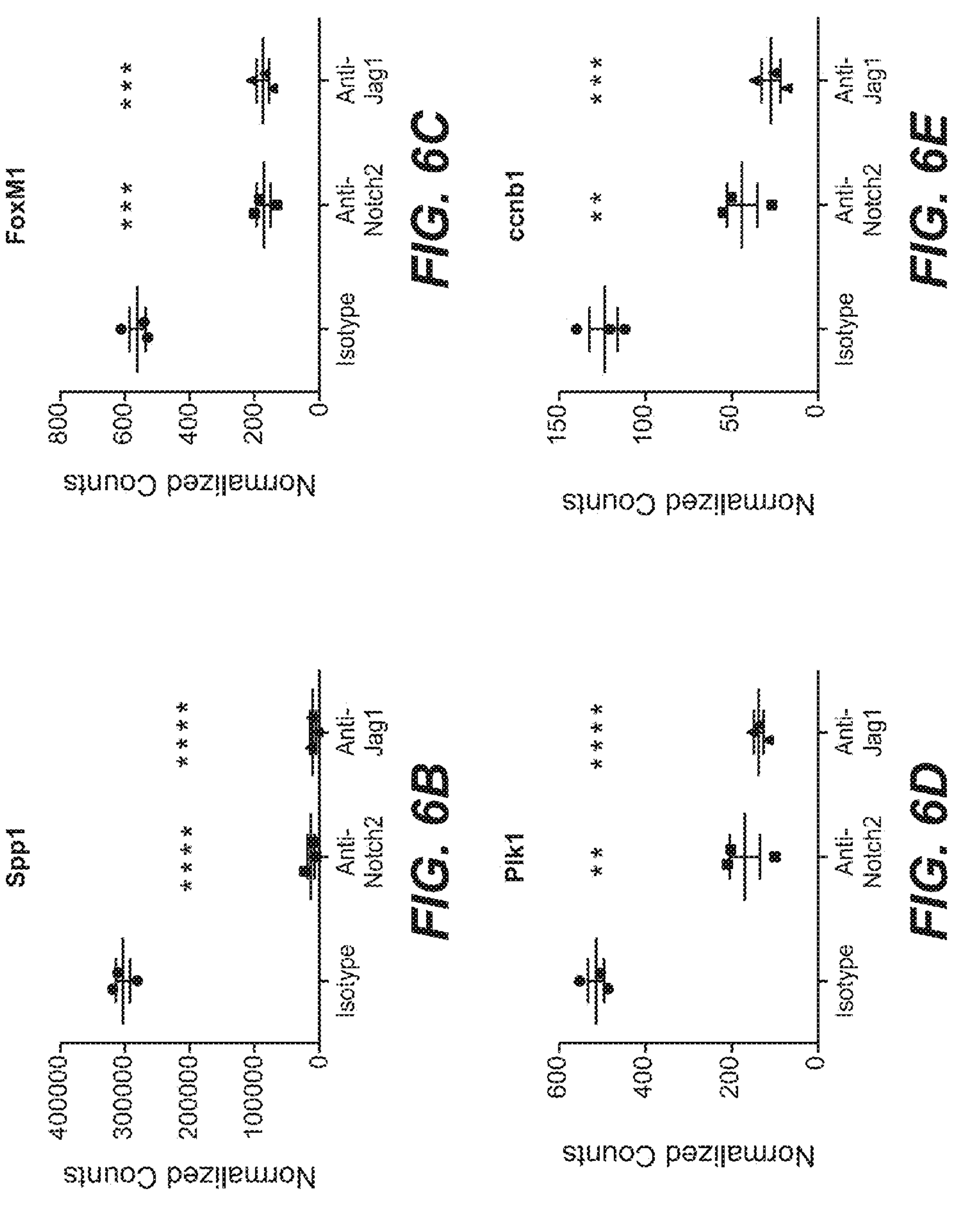
Figure 6F:
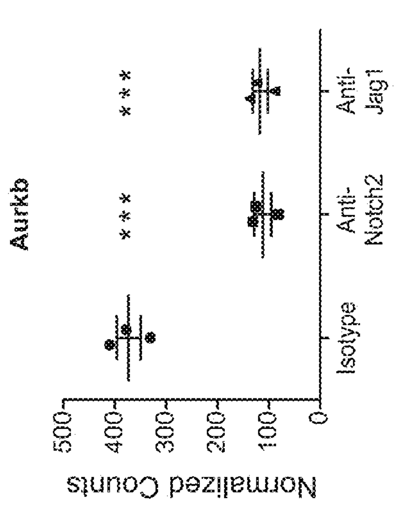
Figure 6G:
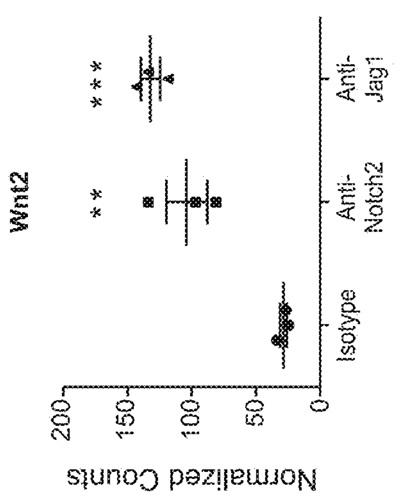
Figure 6H:
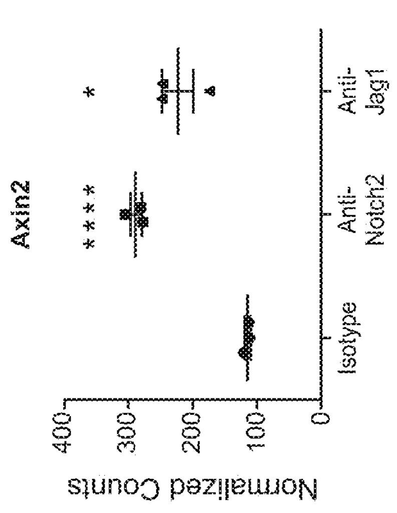
Figure 6I:
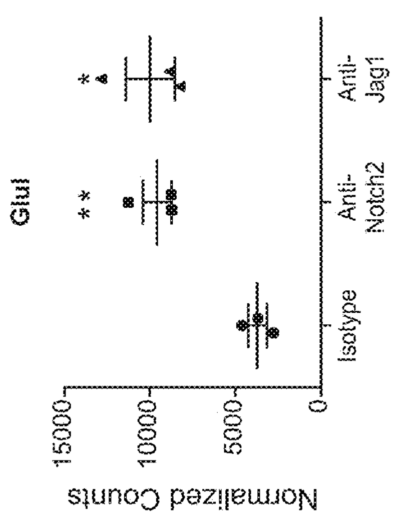

Progenitor-cell and cholangiocarcinoma-like HCC expression signature gene expression was down-regulated in tumor-bearing livers following anti-Notch2 and anti-Jag1 antibody treatment. EpCAM and CK19 expression was significantly down-regulated, as was expression of CD133/Prom1 (FIG. 6A and data not shown) and Spp1 (FIG. 6B), both markers of liver progenitor cells. Because FoxM1 has previously been shown to play a role in HCC proliferation in general (Xia et al., Carcinogenesis 33:2250-2259 (2012)) and in the Ras/Akt model of liver cancer specifically (Ho et al., Hepatology 55:833-845 (2012)), we examined its expression and were able to show that both Notch2 and Jag1 inhibition lead to a decrease in FoxM1 expression (FIG. 6C). Moreover, FoxM1 target genes (Laoukili et al., Nat Cell Biol 7:126-136 (2005)), PLK1 (FIG. 6D), Ccnb1 (FIG. 6E), and Aurkb (FIG. 6F) were also decreased in tumor-bearing livers treated with either anti-Notch2 or anti-Jag1 antibody compared to controls. Markers of Wnt signaling were increased upon Notch2 or Jag1 inhibition. Specifically, Wnt2 ligand was increased (FIG. 6G) as was the Wnt-pathway target geneAxin2 (FIG. 6H). The expression of Glutamine synthetase (Glul; FIG. 6I), a marker of a subset of terminally differentiated hepatocytes, was also increased in tumor-bearing livers treated with either anti-Notch2 or anti-Jag1 antibody compared to controls. These observations are consistent with Notch2 inhibition inducing a decrease in tumor cell proliferation through downregulation of FoxM1 and inducing a differentiated hepatocyte fate through induction of Wnt-signaling (Boulter et al., Nat. Med. 18(4):572 (2012)). It is possible that Notch2 signaling inhibition in liver cancer effects terminal differentiation of tumor cells into hepatocytes. Consistent with this hypothesis, Notch2 and Jag1 inhibition led to an increase in transcriptional markers of terminally differentiated hepatocytes as well as Wnt signaling, which is known to be important in differentiation of hepatocytes from progenitor cells (Boulter et al., Nat. Med. 18(4):572 (2012)). Notch2 and Jag1 inhibition may also be acting by decreasing proliferation and increasing tumor cell death.

Example 9

Expression and Activation of Notch2 in Human Hepatocellular Carcinoma

Human HCC cell lines and primary human HCC tumors were analyzed using quantitative reverse transcription polymerase chain reaction (qRT-PCR) for expression of Notch signaling components. HCC cell lines HepG2, Hep3B, PCL/PRF/5, Snu387, Snu398, Snu423, Snu449, Snu475 were acquired from ATCC (Manassas, Va.). HCC cell lines Huh-7, HLE, HLF, JHH1, JHH4, JHH5, JHH7 were acquired from the Japanese Collection of Bioresources Cell Bank (Osaka, Japan). Whole stained tissue sections were analyzed using Definiens software.

Figure 7A:
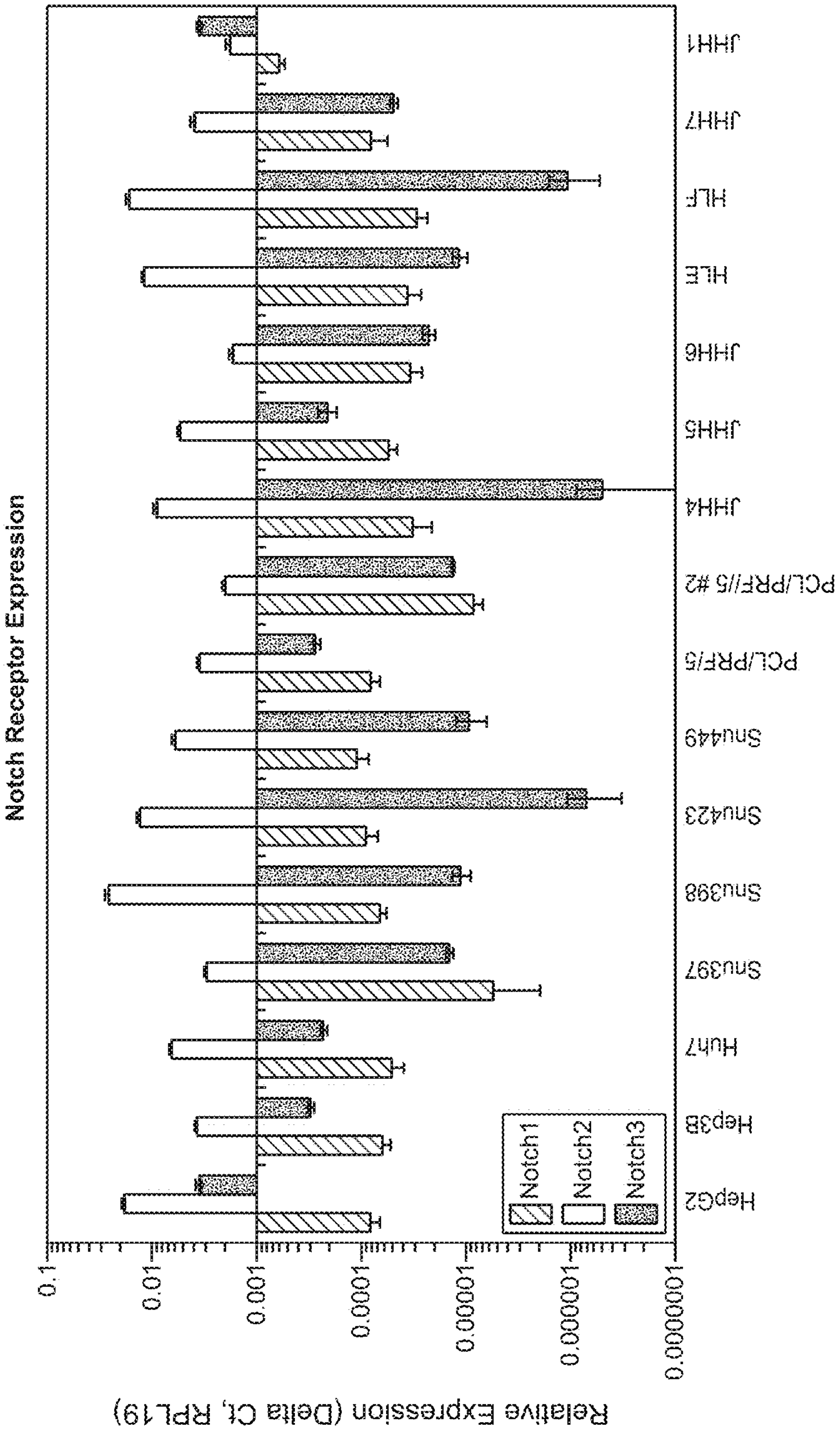

Notch2 was expressed at higher levels than either Notch1 or Notch3 in 15 of 16 cultured HCC cell lines (FIG. 7A). In many cases, Notch2 expression exceeded that of the other Notch family members by more than 10 fold when expression was normalized to a reference gene (RPL19, FIG. 7A). Consistent with this result, prominent expression of Notch2 was observed in 28 of 76 (37%) human primary HCC samples as determined by WIC. In 15 of these 28 human primary HCC samples (54%) Notch2 showed varying degrees of nuclear localization (FIG. 7B) indicating Notch2 pathway activation. Jag1 expression, evaluated by IHC, was observed in 34 of 59 (57%) human primary HCC samples examined (FIG. 7B). Of the 56 human primary HCC samples evaluated for both Notch2 and Jag1, 15 (27%) were found to have expression of both Notch2 and Jag1. Of those 15 tissues with overlapping expression, 11 (73%) showed some degree of Notch2 nuclear localization indicating active Notch2 signaling.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of treating a liver cancer in an individual in need thereof, comprising administering to the individual an effective amount of an anti-Jagged1 (anti-Jag1) antibody, wherein the liver cancer comprises cells that express EpCAM.

2. The method of claim 1, wherein the liver cancer is selected from the group consisting of hepatocellular carcinoma, hepatoma, cholangiocarcinoma, hepatoblastoma, hepatic carcinoma, hepatic angiosarcoma, and metastatic liver cancer.

3. The method of claim 1, wherein the anti-Jag1 antibody is a monoclonal antibody.

4. The method of claim 3, wherein the anti-Jag1 antibody is an IgG1 or IgG2a antibody.

5. The method of claim 3, wherein the anti-Jag1 antibody is a chimeric antibody, a humanized antibody, or a human antibody.

6. The method of claim 1, wherein the anti-Jag1 antibody comprises:

a) heavy chain hypervariable region 1 (HVR-H1) comprising the amino acid sequence of SEQ ID NO:81; heavy chain hypervariable region 2 (HVR-H2) comprising the amino acid sequence of SEQ ID NO:84; heavy chain hypervariable region 3 (HVR-H3) comprising the amino acid sequence of SEQ ID NO:87; light chain hypervariable region 1 (HVR-L1) comprising the amino acid sequence of SEQ ID NO:88; light chain hypervariable region 2 (HVR-L2) comprising the amino acid sequence of SEQ ID NO:89; and light chain hypervariable region 3 (HVR-L3) comprising the amino acid sequence of SEQ ID NO:92; or b) HVR-H1 comprising the amino acid sequence of SEQ ID NO:81; HVR-H2 comprising the amino acid sequence of SEQ ID NO:82; HVR-H3 comprising the amino acid sequence of SEQ ID NO:85; HVR-L1 comprising the amino acid sequence of SEQ ID NO:88; HVR-L2 comprising the amino acid sequence of SEQ ID NO:89; and HVR-L3 comprising the amino acid sequence of SEQ ID NO:90; or c) HVR-H1 comprising the amino acid sequence of SEQ ID NO:81; HVR-H2 comprising the amino acid sequence of SEQ ID NO:82; HVR-H3 comprising the amino acid sequence of SEQ ID NO:86; HVR-L1 comprising the amino acid sequence of SEQ ID NO:88; HVR-L2 comprising the amino acid sequence of SEQ ID NO:89; and HVR-L3 comprising the amino acid sequence of SEQ ID NO:91; or d) HVR-H1 comprising the amino acid sequence of SEQ ID NO:81; HVR-H2 comprising the amino acid sequence of SEQ ID NO:83; HVR-H3 comprising the amino acid sequence of SEQ ID NO:85; HVR-L1 comprising the amino acid sequence of SEQ ID NO:88; HVR-L2 comprising the amino acid sequence SEQ ID NO:89; and HVR-L3 comprising the amino acid sequence of SEQ ID NO:90.

7. The method of claim 1, wherein the anti-Jag1 antibody comprises:

a) a heavy chain variable region (VH) sequence of SEQ ID NO:93 and a light chain variable region (VL) sequence of SEQ ID NO:96; or b) a VH sequence of SEQ ID NO:94 and a VL sequence of SEQ ID NO:97; or c) a VH sequence of SEQ ID NO:95 and a VL sequence of SEQ ID NO:98.

8. The method of claim 1, wherein the anti-Jag1 antibody is conjugated to a cytotoxic agent.

9. The method of claim 8, wherein the cytotoxic agent is selected from toxins, antibiotics, radioactive isotopes and nucleolytic enzymes.

10. The method of claim 1, wherein the liver cancer comprises cells that express at least one of AFP, Notch2, Jag1, Sox9, CK19, Ras, Prom1, Spp1, FoxM1, Plk1, ccnb1, Aurkb, Wnt2, Axin2, or Glul.

11. The method of claim 1, wherein the liver cancer comprises cells having nuclear Notch2.

12. The method of claim 1, wherein the liver cancer comprises cells having activated Ras.

13. The method of claim 1, wherein administering the anti-Jag1 antibody results in a decrease in EpCAM expression in the cells.

14. The method of claim 1, wherein the liver cancer comprises cells that express AFP and wherein administering the anti-Jag1 antibody results in a decrease in AFP expression in the cells.

15. The method of claim 1, wherein administering the anti-Jag1 antibody results in a decrease in expression, compared to expression prior to administering the inhibitor, in the liver cancer of at least one of Prom1, Spp1, FoxM1, Plk1, ccnb1 and Aurkb.

16. The method of claim 1, wherein administering the anti-Jag1 antibody results in an increase in expression in the liver cancer of at least one of Wnt2, Axin2 and Glul.

17. The method of claim 1, wherein the liver cancer is at least in part dependent upon a growth potentiating effect of Notch2 signaling.

* * * * *

SEQUENCE LISTING

```
<160> NUMBER OF SEQ ID NOS: 107

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ser Phe Thr Ser Tyr Gly Met Ser
1               5                   10


<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Asp Leu Gly Ser
1               5


<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Tyr Ile Tyr Pro Tyr Ser Gly Ala Thr Tyr Tyr Ala Asp Ser Val
1               5                   10                  15

Lys Gly


<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Ser Gly Tyr Tyr Arg Ile Ser Ser Ala Met Asp Val
1               5                   10


<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Gln Ser Ile Ser Ser Tyr Leu Ala
```

1 5 10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Arg Ala Ser Gln Ser Asn Arg Arg Phe Leu Ala
1 5 10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Arg Ala Ser Gln Ser Val Arg Ser Phe Leu Ala
1 5 10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Arg Ala Ser Gln Asn Ile Lys Arg Phe Leu Ala
1 5 10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (6)..(6)
<223> OTHER INFORMATION: Ile, Asn or Val
<220> FEATURE:
<221> NAME/KEY: MOD_RES
<222> LOCATION: (7)..(7)
<223> OTHER INFORMATION: Ser, Arg or Lys
<220> FEATURE:
<221> NAME/KEY: MOD_RES
<222> LOCATION: (8)..(8)
<223> OTHER INFORMATION: Ser or Arg
<220> FEATURE:
<221> NAME/KEY: MOD_RES
<222> LOCATION: (9)..(9)
<223> OTHER INFORMATION: Tyr or Phe

<400> SEQUENCE: 9

Arg Ala Ser Gln Xaa Xaa Xaa Xaa Xaa Leu Ala
1 5 10

-continued

```
<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ala Ser Ser Arg Ala Ser
1               5


<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ala Ser Arg Arg Ala Ser
1               5


<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ala Ser Ile Arg Ala Ser
1               5


<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ala Ser Thr Arg Glu Ser
1               5


<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Arg
<220> FEATURE:
<221> NAME/KEY: MOD_RES
<222> LOCATION: (4)..(4)
<223> OTHER INFORMATION: Ser, Arg, Ile or Thr
<220> FEATURE:
<221> NAME/KEY: MOD_RES
<222> LOCATION: (6)..(6)
<223> OTHER INFORMATION: Ala or Glu

<400> SEQUENCE: 14

Xaa Ala Ser Xaa Arg Xaa Ser
```

1 5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Gln Gln Tyr Tyr Ser Ser Pro Leu Thr
1 5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Gln Gln Tyr Tyr Ile Ser Pro Leu Thr
1 5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Gln Gln Tyr Tyr Ile Ser Pro Ser Thr
1 5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Gln Gln Tyr Tyr Arg Ser Pro His Thr
1 5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Ser, Ile or Arg
<220> FEATURE:
<221> NAME/KEY: MOD_RES
<222> LOCATION: (8)..(8)
<223> OTHER INFORMATION: Leu, Ser or His

<400> SEQUENCE: 19

Gln Gln Tyr Tyr Xaa Ser Pro Xaa Thr
1 5

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Ser Tyr
            20                  25                  30

Gly Met Ser Trp Val Arg Gln Ala Pro Gly Lys Gly Leu Glu Trp Val
        35                  40                  45

Ser Tyr Ile Tyr Pro Tyr Ser Gly Ala Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Ser Gly Tyr Tyr Arg Ile Ser Ser Ala Met Asp Val Trp
            100                 105                 110

Gly Gln Gly Thr Leu Val Thr Val Ser Ser
        115                 120
```

<210> SEQ ID NO 21

<400> SEQUENCE: 21

000

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Ser Pro Leu
                85                  90                  95

Thr Phe Gly Gln Gly Thr Lys Val Glu Ile Lys
            100                 105
```

<210> SEQ ID NO 23
<211> LENGTH: 107
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Asn Arg Arg Phe
            20                  25                  30

Leu Ala Trp Tyr Gln Gln Lys Pro Gly Lys Ala Pro Lys Leu Leu Ile
        35                  40                  45

Tyr Gly Ala Ser Arg Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Ser Pro Leu
                85                  90                  95

Thr Phe Gly Gln Gly Thr Lys Val Glu Ile Lys
            100                 105
```

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Arg Ser Phe
            20                  25                  30

Leu Ala Trp Tyr Gln Gln Lys Pro Gly Lys Ala Pro Lys Leu Leu Ile
        35                  40                  45

Tyr Arg Ala Ser Ile Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Ser Pro Ser
                85                  90                  95

Thr Phe Gly Gln Gly Thr Lys Val Glu Ile Lys
            100                 105
```

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Lys Arg Phe
            20                  25                  30

Leu Ala Trp Tyr Gln Gln Lys Pro Gly Lys Ala Pro Lys Leu Leu Ile
        35                  40                  45
```

```
Tyr Gly Ala Ser Thr Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Arg Ser Pro His
                85                  90                  95

Thr Phe Gly Gln Gly Thr Lys Val Glu Ile Lys
            100                 105


<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Val Pro Arg Gly Ser
1               5


<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 27

His His His His His His
1               5


<210> SEQ ID NO 28
<211> LENGTH: 344
<212> TYPE: PRT
<213> ORGANISM: Homo sapiens

<400> SEQUENCE: 28

Gln Phe Glu Leu Glu Ile Leu Ser Met Gln Asn Val Asn Gly Glu Leu
1               5                   10                  15

Gln Asn Gly Asn Cys Cys Gly Gly Ala Arg Asn Pro Gly Asp Arg Lys
            20                  25                  30

Cys Thr Arg Asp Glu Cys Asp Thr Tyr Phe Lys Val Cys Leu Lys Glu
        35                  40                  45

Tyr Gln Ser Arg Val Thr Ala Gly Gly Pro Cys Ser Phe Gly Ser Gly
    50                  55                  60

Ser Thr Pro Val Ile Gly Gly Asn Thr Phe Asn Leu Lys Ala Ser Arg
65                  70                  75                  80

Gly Asn Asp Arg Asn Arg Ile Val Leu Pro Phe Ser Phe Ala Trp Pro
                85                  90                  95

Arg Ser Tyr Thr Leu Leu Val Glu Ala Trp Asp Ser Ser Asn Asp Thr
            100                 105                 110

Val Gln Pro Asp Ser Ile Ile Glu Lys Ala Ser His Ser Gly Met Ile
        115                 120                 125

Asn Pro Ser Arg Gln Trp Gln Thr Leu Lys Gln Asn Thr Gly Val Ala
    130                 135                 140

His Phe Glu Tyr Gln Ile Arg Val Thr Cys Asp Asp Tyr Tyr Tyr Gly
145                 150                 155                 160
```

```
Phe Gly Cys Asn Lys Phe Cys Arg Pro Arg Asp Asp Phe Phe Gly His
                165                 170                 175

Tyr Ala Cys Asp Gln Asn Gly Asn Lys Thr Cys Met Glu Gly Trp Met
            180                 185                 190

Gly Pro Glu Cys Asn Arg Ala Ile Cys Arg Gln Gly Cys Ser Pro Lys
        195                 200                 205

His Gly Ser Cys Lys Leu Pro Gly Asp Cys Arg Cys Gln Tyr Gly Trp
    210                 215                 220

Gln Gly Leu Tyr Cys Asp Lys Cys Ile Pro His Pro Gly Cys Val His
225                 230                 235                 240

Gly Ile Cys Asn Glu Pro Trp Gln Cys Leu Cys Glu Thr Asn Trp Gly
                245                 250                 255

Gly Gln Leu Cys Asp Lys Asp Leu Asn Tyr Cys Gly Thr His Gln Pro
            260                 265                 270

Cys Leu Asn Gly Gly Thr Cys Ser Asn Thr Gly Pro Asp Lys Tyr Gln
        275                 280                 285

Cys Ser Cys Pro Glu Gly Tyr Ser Gly Pro Asn Cys Glu Ile Ala Glu
    290                 295                 300

His Ala Cys Leu Ser Asp Pro Cys His Asn Arg Gly Ser Cys Lys Glu
305                 310                 315                 320

Thr Ser Leu Gly Phe Glu Cys Glu Cys Ser Pro Gly Trp Thr Gly Pro
                325                 330                 335

Thr Cys Ser Thr Asn Ile Asp Asp
            340


<210> SEQ ID NO 29
<211> LENGTH: 314
<212> TYPE: PRT
<213> ORGANISM: Homo sapiens

<400> SEQUENCE: 29

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190
```

```
Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310
```

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

```
Phe Gly Gln Gly Thr Lys Val Glu Ile Lys
1               5                   10
```

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30
```

<210> SEQ ID NO 33
<211> LENGTH: 14
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 33

Trp Val Arg Gln Ala Pro Gly Gln Gly Leu Glu Trp Met Gly
1 5 10

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 34

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Trp Gly Gln Gly Thr Leu Val Thr Val Ser Ser
1 5 10

<210> SEQ ID NO 36
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Gln Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Trp Val Arg Gln Ala Pro Gly Gln Gly Leu Glu Trp Met
1 5 10

<210> SEQ ID NO 38
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 38

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys Ala
20 25 30

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys
20 25 30

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Val Ser
20 25 30

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Trp Ile Arg Gln Pro Pro Gly Lys Gly Leu Glu Trp Ile Gly
1 5 10

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Arg Val Thr Ile Ser Val Asp Thr Ser Lys Asn Gln Phe Ser Leu Lys
1 5 10 15

Leu Ser Ser Val Thr Ala Ala Asp Thr Ala Val Tyr Tyr Cys Ala Arg
20 25 30

<210> SEQ ID NO 43
<211> LENGTH: 25
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 43

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Trp Ile Arg Gln Pro Pro Gly Lys Gly Leu Glu Trp Ile
1               5                   10

<210> SEQ ID NO 45
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 45

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 46

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 48
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Trp Val Arg Gln Ala Pro Gly Lys Gly Leu Glu Trp Val Ser
1 5 10

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala Arg
20 25 30

<210> SEQ ID NO 50
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Glu Val Gln Leu Val Glu Ser Gly Gly Gly Leu Val Gln Pro Gly Gly
1 5 10 15

Ser Leu Arg Leu Ser Cys Ala Ala Ser
20 25

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Trp Val Arg Gln Ala Pro Gly Lys Gly Leu Glu Trp Val
1 5 10

<210> SEQ ID NO 52
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala
20 25 30

<210> SEQ ID NO 53
<211> LENGTH: 30

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys
20 25 30

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 54

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys
20 25 30

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 55

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ser Arg
20 25 30

<210> SEQ ID NO 56
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 56

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ser
20 25 30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 57

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ala Arg
20 25 30

<210> SEQ ID NO 58
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ala
20 25 30

<210> SEQ ID NO 59
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys
20 25 30

<210> SEQ ID NO 60
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Trp Tyr Gln Gln Lys Pro Gly Lys Ala Pro Lys Leu Leu Ile Tyr
1 5 10 15

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

-continued

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30


<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe Gly Gln Gly Thr Lys Val Glu Ile Lys
1               5                   10


<210> SEQ ID NO 64
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys
            20


<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Trp Tyr Leu Gln Lys Pro Gly Gln Ser Pro Gln Leu Leu Ile Tyr
1               5                   10                  15


<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30


<210> SEQ ID NO 67
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67
```

Glu Ile Val Leu Thr Gln Ser Pro Gly Thr Leu Ser Leu Ser Pro Gly
1 5 10 15

Glu Arg Ala Thr Leu Ser Cys
20

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Trp Tyr Gln Gln Lys Pro Gly Gln Ala Pro Arg Leu Leu Ile Tyr
1 5 10 15

<210> SEQ ID NO 69
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Gly Ile Pro Asp Arg Phe Ser Gly Ser Gly Ser Gly Thr Asp Phe Thr
1 5 10 15

Leu Thr Ile Ser Arg Leu Glu Pro Glu Asp Phe Ala Val Tyr Tyr Cys
20 25 30

<210> SEQ ID NO 70
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Asp Ile Val Met Thr Gln Ser Pro Asp Ser Leu Ala Val Ser Leu Gly
1 5 10 15

Glu Arg Ala Thr Ile Asn Cys
20

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Trp Tyr Gln Gln Lys Pro Gly Gln Pro Pro Lys Leu Leu Ile Tyr
1 5 10 15

<210> SEQ ID NO 72
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30


<210> SEQ ID NO 73
<211> LENGTH: 256
<212> TYPE: PRT
<213> ORGANISM: Homo sapiens

<400> SEQUENCE: 73

Pro Ala Thr Cys Leu Ser Gln Tyr Cys Ala Asp Lys Ala Arg Asp Gly
1               5                   10                  15

Val Cys Asp Glu Ala Cys Asn Ser His Ala Cys Gln Trp Asp Gly Gly
            20                  25                  30

Asp Cys Ser Leu Thr Met Glu Asn Pro Trp Ala Asn Cys Ser Ser Pro
        35                  40                  45

Leu Pro Cys Trp Asp Tyr Ile Asn Asn Gln Cys Asp Glu Leu Cys Asn
    50                  55                  60

Thr Val Glu Cys Leu Phe Asp Asn Phe Glu Cys Gln Gly Asn Ser Lys
65                  70                  75                  80

Thr Cys Lys Tyr Asp Lys Tyr Cys Ala Asp His Phe Lys Asp Asn His
                85                  90                  95

Cys Asp Gln Gly Cys Asn Ser Glu Glu Cys Gly Trp Asp Gly Leu Asp
            100                 105                 110

Cys Ala Ala Asp Gln Pro Glu Asn Leu Ala Glu Gly Thr Leu Val Ile
        115                 120                 125

Val Val Leu Met Pro Pro Glu Gln Leu Leu Gln Asp Ala Arg Ser Phe
    130                 135                 140

Leu Arg Ala Leu Gly Thr Leu Leu His Thr Asn Leu Arg Ile Lys Arg
145                 150                 155                 160

Asp Ser Gln Gly Glu Leu Met Val Tyr Pro Tyr Tyr Gly Glu Lys Ser
                165                 170                 175

Ala Ala Met Lys Lys Gln Arg Met Thr Arg Arg Ser Leu Pro Gly Glu
            180                 185                 190

Gln Glu Gln Glu Val Ala Gly Ser Lys Val Phe Leu Glu Ile Asp Asn
        195                 200                 205

Arg Gln Cys Val Gln Asp Ser Asp His Cys Phe Lys Asn Thr Asp Ala
    210                 215                 220

Ala Ala Ala Leu Leu Ala Ser His Ala Ile Gln Gly Thr Leu Ser Tyr
225                 230                 235                 240

Pro Leu Val Ser Val Val Ser Glu Ser Leu Thr Pro Glu Arg Thr Gln
                245                 250                 255


<210> SEQ ID NO 74
<211> LENGTH: 258
<212> TYPE: PRT
<213> ORGANISM: Mus sp.

<400> SEQUENCE: 74

Pro Ala Thr Cys Gln Ser Gln Tyr Cys Ala Asp Lys Ala Arg Asp Gly
1               5                   10                  15

Ile Cys Asp Glu Ala Cys Asn Ser His Ala Cys Gln Trp Asp Gly Gly
            20                  25                  30

Asp Cys Ser Leu Thr Met Glu Asp Pro Trp Ala Asn Cys Thr Ser Thr
        35                  40                  45
```

```
Leu Arg Cys Trp Glu Tyr Ile Asn Asn Gln Cys Asp Glu Gln Cys Asn
    50                  55                  60

Thr Ala Glu Cys Leu Phe Asp Asn Phe Glu Cys Gln Arg Asn Ser Lys
65                  70                  75                  80

Thr Cys Lys Tyr Asp Lys Tyr Cys Ala Asp His Phe Lys Asp Asn His
                85                  90                  95

Cys Asp Gln Gly Cys Asn Ser Glu Glu Cys Gly Trp Asp Gly Leu Asp
            100                 105                 110

Cys Ala Ser Asp Gln Pro Glu Asn Leu Ala Glu Gly Thr Leu Ile Ile
        115                 120                 125

Val Val Leu Leu Pro Pro Glu Gln Leu Leu Gln Asp Ser Arg Ser Phe
    130                 135                 140

Leu Arg Ala Leu Gly Thr Leu Leu His Thr Asn Leu Arg Ile Lys Gln
145                 150                 155                 160

Asp Ser Gln Gly Ala Leu Met Val Tyr Pro Tyr Phe Gly Glu Lys Ser
                165                 170                 175

Ala Ala Met Lys Lys Gln Lys Met Thr Arg Arg Ser Leu Pro Glu Glu
            180                 185                 190

Gln Glu Gln Glu Gln Glu Val Ile Gly Ser Lys Ile Phe Leu Glu Ile
        195                 200                 205

Asp Asn Arg Gln Cys Val Gln Asp Ser Asp Gln Cys Phe Lys Asn Thr
    210                 215                 220

Asp Ala Ala Ala Ala Leu Leu Ala Ser His Ala Ile Gln Gly Thr Leu
225                 230                 235                 240

Ser Tyr Pro Leu Val Ser Val Phe Ser Glu Leu Glu Ser Pro Arg Asn
                245                 250                 255

Ala Gln


<210> SEQ ID NO 75
<211> LENGTH: 2471
<212> TYPE: PRT
<213> ORGANISM: Homo sapiens

<400> SEQUENCE: 75

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160
```

-continued

```
Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
```

-continued

```
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
        835                 840                 845

Lys Glu Ser Pro Asn Phe Glu Ser Tyr Thr Cys Leu Cys Ala Pro Gly
    850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
        915                 920                 925

Gly Val Asn Thr Phe Ser Cys Leu Cys Leu Pro Gly Phe Thr Gly Asp
    930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
                965                 970                 975

Ala Gly Phe Asp Gly Val His Cys Glu Asn Asn Ile Asn Glu Cys Thr
            980                 985                 990

Glu Ser Ser Cys Phe Asn Gly Gly  Thr Cys Val Asp Gly  Ile Asn Ser
        995                 1000                1005
```

```
Phe Ser  Cys Leu Cys Pro Val  Gly Phe Thr Gly Ser  Phe Cys Leu
    1010                 1015                 1020

His Glu  Ile Asn Glu Cys Ser  Ser His Pro Cys Leu  Asn Glu Gly
    1025                 1030                 1035

Thr Cys  Val Asp Gly Leu Gly  Thr Tyr Arg Cys Ser  Cys Pro Leu
    1040                 1045                 1050

Gly Tyr  Thr Gly Lys Asn Cys  Gln Thr Leu Val Asn  Leu Cys Ser
    1055                 1060                 1065

Arg Ser  Pro Cys Lys Asn Lys  Gly Thr Cys Val Gln  Lys Lys Ala
    1070                 1075                 1080

Glu Ser  Gln Cys Leu Cys Pro  Ser Gly Trp Ala Gly  Ala Tyr Cys
    1085                 1090                 1095

Asp Val  Pro Asn Val Ser Cys  Asp Ile Ala Ala Ser  Arg Arg Gly
    1100                 1105                 1110

Val Leu  Val Glu His Leu Cys  Gln His Ser Gly Val  Cys Ile Asn
    1115                 1120                 1125

Ala Gly  Asn Thr His Tyr Cys  Gln Cys Pro Leu Gly  Tyr Thr Gly
    1130                 1135                 1140

Ser Tyr  Cys Glu Glu Gln Leu  Asp Glu Cys Ala Ser  Asn Pro Cys
    1145                 1150                 1155

Gln His  Gly Ala Thr Cys Ser  Asp Phe Ile Gly Gly  Tyr Arg Cys
    1160                 1165                 1170

Glu Cys  Val Pro Gly Tyr Gln  Gly Val Asn Cys Glu  Tyr Glu Val
    1175                 1180                 1185

Asp Glu  Cys Gln Asn Gln Pro  Cys Gln Asn Gly Gly  Thr Cys Ile
    1190                 1195                 1200

Asp Leu  Val Asn His Phe Lys  Cys Ser Cys Pro Pro  Gly Thr Arg
    1205                 1210                 1215

Gly Leu  Leu Cys Glu Glu Asn  Ile Asp Asp Cys Ala  Arg Gly Pro
    1220                 1225                 1230

His Cys  Leu Asn Gly Gly Gln  Cys Met Asp Arg Ile  Gly Gly Tyr
    1235                 1240                 1245

Ser Cys  Arg Cys Leu Pro Gly  Phe Ala Gly Glu Arg  Cys Glu Gly
    1250                 1255                 1260

Asp Ile  Asn Glu Cys Leu Ser  Asn Pro Cys Ser Ser  Glu Gly Ser
    1265                 1270                 1275

Leu Asp  Cys Ile Gln Leu Thr  Asn Asp Tyr Leu Cys  Val Cys Arg
    1280                 1285                 1290

Ser Ala  Phe Thr Gly Arg His  Cys Glu Thr Phe Val  Asp Val Cys
    1295                 1300                 1305

Pro Gln  Met Pro Cys Leu Asn  Gly Gly Thr Cys Ala  Val Ala Ser
    1310                 1315                 1320

Asn Met  Pro Asp Gly Phe Ile  Cys Arg Cys Pro Pro  Gly Phe Ser
    1325                 1330                 1335

Gly Ala  Arg Cys Gln Ser Ser  Cys Gly Gln Val Lys  Cys Arg Lys
    1340                 1345                 1350

Gly Glu  Gln Cys Val His Thr  Ala Ser Gly Pro Arg  Cys Phe Cys
    1355                 1360                 1365

Pro Ser  Pro Arg Asp Cys Glu  Ser Gly Cys Ala Ser  Ser Pro Cys
    1370                 1375                 1380

Gln His  Gly Gly Ser Cys His  Pro Gln Arg Gln Pro  Pro Tyr Tyr
    1385                 1390                 1395
```

-continued

```
Ser Cys  Gln Cys Ala Pro Pro  Phe Ser Gly Ser Arg  Cys Glu Leu
    1400                 1405                 1410

Tyr Thr  Ala Pro Pro Ser Thr  Pro Pro Ala Thr Cys  Leu Ser Gln
    1415                 1420                 1425

Tyr Cys  Ala Asp Lys Ala Arg  Asp Gly Val Cys Asp  Glu Ala Cys
    1430                 1435                 1440

Asn Ser  His Ala Cys Gln Trp  Asp Gly Gly Asp Cys  Ser Leu Thr
    1445                 1450                 1455

Met Glu  Asn Pro Trp Ala Asn  Cys Ser Ser Pro Leu  Pro Cys Trp
    1460                 1465                 1470

Asp Tyr  Ile Asn Asn Gln Cys  Asp Glu Leu Cys Asn  Thr Val Glu
    1475                 1480                 1485

Cys Leu  Phe Asp Asn Phe Glu  Cys Gln Gly Asn Ser  Lys Thr Cys
    1490                 1495                 1500

Lys Tyr  Asp Lys Tyr Cys Ala  Asp His Phe Lys Asp  Asn His Cys
    1505                 1510                 1515

Asp Gln  Gly Cys Asn Ser Glu  Glu Cys Gly Trp Asp  Gly Leu Asp
    1520                 1525                 1530

Cys Ala  Ala Asp Gln Pro Glu  Asn Leu Ala Glu Gly  Thr Leu Val
    1535                 1540                 1545

Ile Val  Val Leu Met Pro Pro  Glu Gln Leu Leu Gln  Asp Ala Arg
    1550                 1555                 1560

Ser Phe  Leu Arg Ala Leu Gly  Thr Leu Leu His Thr  Asn Leu Arg
    1565                 1570                 1575

Ile Lys  Arg Asp Ser Gln Gly  Glu Leu Met Val Tyr  Pro Tyr Tyr
    1580                 1585                 1590

Gly Glu  Lys Ser Ala Ala Met  Lys Lys Gln Arg Met  Thr Arg Arg
    1595                 1600                 1605

Ser Leu  Pro Gly Glu Gln Glu  Gln Glu Val Ala Gly  Ser Lys Val
    1610                 1615                 1620

Phe Leu  Glu Ile Asp Asn Arg  Gln Cys Val Gln Asp  Ser Asp His
    1625                 1630                 1635

Cys Phe  Lys Asn Thr Asp Ala  Ala Ala Ala Leu Leu  Ala Ser His
    1640                 1645                 1650

Ala Ile  Gln Gly Thr Leu Ser  Tyr Pro Leu Val Ser  Val Val Ser
    1655                 1660                 1665

Glu Ser  Leu Thr Pro Glu Arg  Thr Gln Leu Leu Tyr  Leu Leu Ala
    1670                 1675                 1680

Val Ala  Val Val Ile Ile Leu  Phe Ile Ile Leu Leu  Gly Val Ile
    1685                 1690                 1695

Met Ala  Lys Arg Lys Arg Lys  His Gly Ser Leu Trp  Leu Pro Glu
    1700                 1705                 1710

Gly Phe  Thr Leu Arg Arg Asp  Ala Ser Asn His Lys  Arg Arg Glu
    1715                 1720                 1725

Pro Val  Gly Gln Asp Ala Val  Gly Leu Lys Asn Leu  Ser Val Gln
    1730                 1735                 1740

Val Ser  Glu Ala Asn Leu Ile  Gly Thr Gly Thr Ser  Glu His Trp
    1745                 1750                 1755

Val Asp  Asp Glu Gly Pro Gln  Pro Lys Lys Val Lys  Ala Glu Asp
    1760                 1765                 1770

Glu Ala  Leu Leu Ser Glu Glu  Asp Asp Pro Ile Asp  Arg Arg Pro
    1775                 1780                 1785

Trp Thr  Gln Gln His Leu Glu  Ala Ala Asp Ile Arg  Arg Thr Pro
```

```
    1790                1795                1800

Ser Leu  Ala Leu Thr Pro Pro  Gln Ala Glu Gln Glu  Val Asp Val
    1805                1810                1815

Leu Asp  Val Asn Val Arg Gly  Pro Asp Gly Cys Thr  Pro Leu Met
    1820                1825                1830

Leu Ala  Ser Leu Arg Gly Gly  Ser Ser Asp Leu Ser  Asp Glu Asp
    1835                1840                1845

Glu Asp  Ala Glu Asp Ser Ser  Ala Asn Ile Ile Thr  Asp Leu Val
    1850                1855                1860

Tyr Gln  Gly Ala Ser Leu Gln  Ala Gln Thr Asp Arg  Thr Gly Glu
    1865                1870                1875

Met Ala  Leu His Leu Ala Ala  Arg Tyr Ser Arg Ala  Asp Ala Ala
    1880                1885                1890

Lys Arg  Leu Leu Asp Ala Gly  Ala Asp Ala Asn Ala  Gln Asp Asn
    1895                1900                1905

Met Gly  Arg Cys Pro Leu His  Ala Ala Val Ala Ala  Asp Ala Gln
    1910                1915                1920

Gly Val  Phe Gln Ile Leu Ile  Arg Asn Arg Val Thr  Asp Leu Asp
    1925                1930                1935

Ala Arg  Met Asn Asp Gly Thr  Thr Pro Leu Ile Leu  Ala Ala Arg
    1940                1945                1950

Leu Ala  Val Glu Gly Met Val  Ala Glu Leu Ile Asn  Cys Gln Ala
    1955                1960                1965

Asp Val  Asn Ala Val Asp Asp  His Gly Lys Ser Ala  Leu His Trp
    1970                1975                1980

Ala Ala  Ala Val Asn Asn Val  Glu Ala Thr Leu Leu  Leu Leu Lys
    1985                1990                1995

Asn Gly  Ala Asn Arg Asp Met  Gln Asp Asn Lys Glu  Glu Thr Pro
    2000                2005                2010

Leu Phe  Leu Ala Ala Arg Glu  Gly Ser Tyr Glu Ala  Ala Lys Ile
    2015                2020                2025

Leu Leu  Asp His Phe Ala Asn  Arg Asp Ile Thr Asp  His Met Asp
    2030                2035                2040

Arg Leu  Pro Arg Asp Val Ala  Arg Asp Arg Met His  His Asp Ile
    2045                2050                2055

Val Arg  Leu Leu Asp Glu Tyr  Asn Val Thr Pro Ser  Pro Pro Gly
    2060                2065                2070

Thr Val  Leu Thr Ser Ala Leu  Ser Pro Val Ile Cys  Gly Pro Asn
    2075                2080                2085

Arg Ser  Phe Leu Ser Leu Lys  His Thr Pro Met Gly  Lys Lys Ser
    2090                2095                2100

Arg Arg  Pro Ser Ala Lys Ser  Thr Met Pro Thr Ser  Leu Pro Asn
    2105                2110                2115

Leu Ala  Lys Glu Ala Lys Asp  Ala Lys Gly Ser Arg  Arg Lys Lys
    2120                2125                2130

Ser Leu  Ser Glu Lys Val Gln  Leu Ser Glu Ser Ser  Val Thr Leu
    2135                2140                2145

Ser Pro  Val Asp Ser Leu Glu  Ser Pro His Thr Tyr  Val Ser Asp
    2150                2155                2160

Thr Thr  Ser Ser Pro Met Ile  Thr Ser Pro Gly Ile  Leu Gln Ala
    2165                2170                2175

Ser Pro  Asn Pro Met Leu Ala  Thr Ala Ala Pro Pro  Ala Pro Val
    2180                2185                2190
```

His Ala Gln His Ala Leu Ser Phe Ser Asn Leu His Glu Met Gln
2195 2200 2205

Pro Leu Ala His Gly Ala Ser Thr Val Leu Pro Ser Val Ser Gln
2210 2215 2220

Leu Leu Ser His His His Ile Val Ser Pro Gly Ser Gly Ser Ala
2225 2230 2235

Gly Ser Leu Ser Arg Leu His Pro Val Pro Val Pro Ala Asp Trp
2240 2245 2250

Met Asn Arg Met Glu Val Asn Glu Thr Gln Tyr Asn Glu Met Phe
2255 2260 2265

Gly Met Val Leu Ala Pro Ala Glu Gly Thr His Pro Gly Ile Ala
2270 2275 2280

Pro Gln Ser Arg Pro Pro Glu Gly Lys His Ile Thr Thr Pro Arg
2285 2290 2295

Glu Pro Leu Pro Pro Ile Val Thr Phe Gln Leu Ile Pro Lys Gly
2300 2305 2310

Ser Ile Ala Gln Pro Ala Gly Ala Pro Gln Pro Gln Ser Thr Cys
2315 2320 2325

Pro Pro Ala Val Ala Gly Pro Leu Pro Thr Met Tyr Gln Ile Pro
2330 2335 2340

Glu Met Ala Arg Leu Pro Ser Val Ala Phe Pro Thr Ala Met Met
2345 2350 2355

Pro Gln Gln Asp Gly Gln Val Ala Gln Thr Ile Leu Pro Ala Tyr
2360 2365 2370

His Pro Phe Pro Ala Ser Val Gly Lys Tyr Pro Thr Pro Pro Ser
2375 2380 2385

Gln His Ser Tyr Ala Ser Ser Asn Ala Ala Glu Arg Thr Pro Ser
2390 2395 2400

His Ser Gly His Leu Gln Gly Glu His Pro Tyr Leu Thr Pro Ser
2405 2410 2415

Pro Glu Ser Pro Asp Gln Trp Ser Ser Ser Ser Pro His Ser Ala
2420 2425 2430

Ser Asp Trp Ser Asp Val Thr Thr Ser Pro Thr Pro Gly Gly Ala
2435 2440 2445

Gly Gly Gly Gln Arg Gly Pro Gly Thr His Met Ser Glu Pro Pro
2450 2455 2460

His Asn Asn Met Gln Val Tyr Ala
2465 2470

<210> SEQ ID NO 76
<211> LENGTH: 1180
<212> TYPE: PRT
<213> ORGANISM: Homo sapiens

<400> SEQUENCE: 76

Met Pro Asp Leu Arg Pro Ala Ala Leu Arg Ala Leu Leu Trp Leu Trp
1 5 10 15

Leu Cys Gly Ala Gly Pro Ala His Ala Leu Gln Cys Arg Gly Gly Gln
20 25 30

Glu Pro Cys Val Asn Glu Gly Thr Cys Val Thr Tyr His Asn Gly Thr
35 40 45

Gly Phe Cys Arg Cys Pro Glu Gly Phe Leu Gly Glu Tyr Cys Gln His
50 55 60

Arg Asp Pro Cys Glu Lys Asn Arg Cys Gln Asn Gly Gly Thr Cys Val

-continued

```
65                  70                  75                  80

Pro Gln Gly Met Leu Gly Lys Ala Thr Cys Arg Cys Ala Pro Gly Phe
                85                  90                  95

Thr Gly Glu Asp Cys Gln Tyr Ser Thr Ser His Pro Cys Phe Val Ser
            100                 105                 110

Arg Pro Cys Gln Asn Gly Gly Thr Cys His Met Leu Ser Arg Asp Thr
        115                 120                 125

Tyr Glu Cys Thr Cys Gln Val Gly Phe Thr Gly Lys Gln Cys Gln Trp
    130                 135                 140

Thr Asp Ala Cys Leu Ser His Pro Cys Glu Asn Gly Ser Thr Cys Thr
145                 150                 155                 160

Ser Val Ala Ser Gln Phe Ser Cys Lys Cys Pro Ala Gly Leu Thr Gly
                165                 170                 175

Gln Lys Cys Glu Ala Asp Ile Asn Glu Cys Asp Ile Pro Gly Arg Cys
            180                 185                 190

Gln His Gly Gly Thr Cys Leu Asn Leu Pro Gly Ser Tyr Arg Cys Gln
        195                 200                 205

Cys Gly Gln Gly Phe Thr Gly Gln His Cys Asp Ser Pro Tyr Val Arg
    210                 215                 220

Gly Leu Pro Cys Val Asn Gly Gly Thr Cys Arg Gln Thr Gly Asp Phe
225                 230                 235                 240

Thr Leu Glu Cys Asn Cys Leu Pro Gly Phe Glu Gly Ser Thr Cys Glu
                245                 250                 255

Arg Asn Ile Asp Asp Cys Pro Asn His Lys Cys Gln Asn Gly Gly Val
            260                 265                 270

Cys Val Asp Gly Val Asn Thr Tyr Asn Cys Arg Cys Pro Pro Gln Trp
        275                 280                 285

Thr Gly Gln Phe Cys Thr Glu Asp Val Asp Glu Cys Leu Leu Gln Pro
    290                 295                 300

Asn Ala Cys Gln Asn Gly Gly Thr Cys Thr Asn Arg Asn Gly Gly Tyr
305                 310                 315                 320

Gly Cys Val Cys Val Asn Gly Trp Ser Gly Asp Asp Cys Ser Glu Asn
                325                 330                 335

Ile Asp Asp Cys Ala Tyr Ala Ser Cys Thr Pro Gly Ser Thr Cys Ile
            340                 345                 350

Asp Arg Val Ala Ser Phe Ser Cys Leu Cys Pro Glu Gly Lys Ala Gly
        355                 360                 365

Leu Leu Cys His Leu Asp Asp Ala Cys Ile Ser Asn Pro Cys His Lys
    370                 375                 380

Gly Ala Leu Cys Asp Thr Asn Pro Leu Asn Gly Gln Tyr Ile Cys Thr
385                 390                 395                 400

Cys Pro Gln Gly Tyr Lys Gly Ala Asp Cys Thr Glu Asp Val Asp Glu
                405                 410                 415

Cys Ala Met Ala Asn Ser Asn Pro Cys Glu His Ala Gly Lys Cys Val
            420                 425                 430

Asn Thr Asp Gly Ala Phe His Cys Glu Cys Leu Lys Gly Tyr Ala Gly
        435                 440                 445

Pro Arg Cys Glu Met Asp Ile Asn Glu Cys His Ser Asp Pro Cys Gln
    450                 455                 460

Asn Asp Ala Thr Cys Leu Asp Lys Ile Gly Gly Phe Thr Cys Leu Cys
465                 470                 475                 480

Met Pro Gly Phe Lys Gly Val His Cys Glu Leu Glu Val Asn Glu Cys
                485                 490                 495
```

```
Gln Ser Asn Pro Cys Val Asn Asn Gly Gln Cys Val Asp Lys Val Asn
            500                 505                 510

Arg Phe Gln Cys Leu Cys Pro Pro Gly Phe Thr Gly Pro Val Cys Gln
        515                 520                 525

Ile Asp Ile Asp Asp Cys Ser Ser Thr Pro Cys Leu Asn Gly Ala Lys
    530                 535                 540

Cys Ile Asp His Pro Asn Gly Tyr Glu Cys Gln Cys Ala Thr Gly Phe
545                 550                 555                 560

Thr Gly Ile Leu Cys Asp Glu Asn Ile Asp Asn Cys Asp Pro Asp Pro
                565                 570                 575

Cys His His Gly Gln Cys Gln Asp Gly Ile Asp Ser Tyr Thr Cys Ile
            580                 585                 590

Cys Asn Pro Gly Tyr Met Gly Ala Ile Cys Ser Asp Gln Ile Asp Glu
        595                 600                 605

Cys Tyr Ser Ser Pro Cys Leu Asn Asp Gly Arg Cys Ile Asp Leu Val
    610                 615                 620

Asn Gly Tyr Gln Cys Asn Cys Gln Pro Gly Thr Ser Gly Leu Asn Cys
625                 630                 635                 640

Glu Ile Asn Phe Asp Asp Cys Ala Ser Asn Pro Cys Met His Gly Val
                645                 650                 655

Cys Val Asp Gly Ile Asn Arg Tyr Ser Cys Val Cys Ser Pro Gly Phe
            660                 665                 670

Thr Gly Gln Arg Cys Asn Ile Asp Ile Asp Glu Cys Ala Ser Asn Pro
        675                 680                 685

Cys Arg Lys Gly Ala Thr Cys Ile Asn Asp Val Asn Gly Phe Arg Cys
    690                 695                 700

Ile Cys Pro Glu Gly Pro His His Pro Ser Cys Tyr Ser Gln Val Asn
705                 710                 715                 720

Glu Cys Leu Ser Asn Pro Cys Ile His Gly Asn Cys Thr Gly Gly Leu
                725                 730                 735

Ser Gly Tyr Lys Cys Leu Cys Asp Ala Gly Trp Val Gly Val Asn Cys
            740                 745                 750

Glu Val Asp Lys Asn Glu Cys Leu Ser Asn Pro Cys Gln Asn Gly Gly
        755                 760                 765

Thr Cys Asn Asn Leu Val Asn Gly Tyr Arg Cys Thr Cys Lys Lys Gly
    770                 775                 780

Phe Lys Gly Tyr Asn Cys Gln Val Asn Ile Asp Glu Cys Ala Ser Asn
785                 790                 795                 800

Pro Cys Leu Asn Gln Gly Thr Cys Phe Asp Asp Val Ser Gly Tyr Thr
                805                 810                 815

Cys His Cys Met Leu Pro Tyr Thr Gly Lys Asn Cys Gln Thr Val Leu
            820                 825                 830

Ala Pro Cys Ser Pro Asn Pro Cys Glu Asn Ala Ala Val Cys Lys Glu
        835                 840                 845

Ala Pro Asn Phe Glu Ser Phe Ser Cys Leu Cys Ala Pro Gly Trp Gln
    850                 855                 860

Gly Lys Arg Cys Thr Val Asp Val Asp Glu Cys Ile Ser Lys Pro Cys
865                 870                 875                 880

Met Asn Asn Gly Val Cys His Asn Thr Gln Gly Ser Tyr Val Cys Glu
                885                 890                 895

Cys Pro Pro Gly Phe Ser Gly Met Asp Cys Glu Glu Asp Ile Asn Asp
            900                 905                 910
```

-continued

```
Cys Leu Ala Asn Pro Cys Gln Asn Gly Gly Ser Cys Val Asp His Val
        915                 920                 925

Asn Thr Phe Ser Cys Gln Cys His Pro Gly Phe Ile Gly Asp Lys Cys
    930                 935                 940

Gln Thr Asp Met Asn Glu Cys Leu Ser Glu Pro Cys Lys Asn Gly Gly
945                 950                 955                 960

Thr Cys Ser Asp Tyr Val Asn Ser Tyr Thr Cys Thr Cys Pro Ala Gly
                965                 970                 975

Phe His Gly Val His Cys Glu Asn Asn Ile Asp Glu Cys Thr Glu Ser
            980                 985                 990

Ser Cys Phe Asn Gly Gly Thr Cys  Val Asp Gly Ile Asn  Ser Phe Ser
        995                 1000                1005

Cys Leu  Cys Pro Val Gly Phe  Thr Gly Pro Phe Cys  Leu His Asp
    1010                 1015                1020

Ile Asn  Glu Cys Ser Ser Asn  Pro Cys Leu Asn Ala  Gly Thr Cys
    1025                 1030                1035

Val Asp  Gly Leu Gly Thr Tyr  Arg Cys Ile Cys Pro  Leu Gly Tyr
    1040                 1045                1050

Thr Gly  Lys Asn Cys Gln Thr  Leu Val Asn Leu Cys  Ser Arg Ser
    1055                 1060                1065

Pro Cys  Lys Asn Lys Gly Thr  Cys Val Gln Glu Lys  Ala Arg Pro
    1070                 1075                1080

His Cys  Leu Cys Pro Pro Gly  Trp Asp Gly Ala Tyr  Cys Asp Val
    1085                 1090                1095

Leu Asn  Val Ser Cys Lys Ala  Ala Ala Leu Gln Lys  Gly Val Pro
    1100                 1105                1110

Val Glu  His Leu Cys Gln His  Ser Gly Ile Cys Ile  Asn Ala Gly
    1115                 1120                1125

Asn Thr  His His Cys Gln Cys  Pro Leu Gly Tyr Thr  Gly Ser Tyr
    1130                 1135                1140

Cys Glu  Glu Gln Leu Asp Glu  Cys Ala Ser Asn Pro  Cys Gln His
    1145                 1150                1155

Gly Ala  Thr Cys Asn Asp Phe  Ile Gly Gly Tyr Arg  Cys Glu Cys
    1160                 1165                1170

Val Pro  Gly Tyr Gln Gly Val
    1175                 1180
```

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

```
Phe Gly Gln Gly Thr Lys Val Glu Ile Lys Arg
1               5                   10
```

<210> SEQ ID NO 78
<211> LENGTH: 1218
<212> TYPE: PRT
<213> ORGANISM: Homo sapiens

<400> SEQUENCE: 78

```
Met Arg Ser Pro Arg Thr Arg Gly Arg Ser Gly Arg Pro Leu Ser Leu
1               5                   10                  15
```

```
Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
```

-continued

```
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860
```

```
Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile  Ala Cys Glu Pro Ser  Pro Ser Ala
        995                 1000                1005

Asn Asn  Glu Ile His Val Ala  Ile Ser Ala Glu Asp  Ile Arg Asp
    1010                1015                1020

Asp Gly  Asn Pro Ile Lys Glu  Ile Thr Asp Lys Ile  Ile Asp Leu
    1025                1030                1035

Val Ser  Lys Arg Asp Gly Asn  Ser Ser Leu Ile Ala  Ala Val Ala
    1040                1045                1050

Glu Val  Arg Val Gln Arg Arg  Pro Leu Lys Asn Arg  Thr Asp Phe
    1055                1060                1065

Leu Val  Pro Leu Leu Ser Ser  Val Leu Thr Val Ala  Trp Ile Cys
    1070                1075                1080

Cys Leu  Val Thr Ala Phe Tyr  Trp Cys Leu Arg Lys  Arg Arg Lys
    1085                1090                1095

Pro Gly  Ser His Thr His Ser  Ala Ser Glu Asp Asn  Thr Thr Asn
    1100                1105                1110

Asn Val  Arg Glu Gln Leu Asn  Gln Ile Lys Asn Pro  Ile Glu Lys
    1115                1120                1125

His Gly  Ala Asn Thr Val Pro  Ile Lys Asp Tyr Glu  Asn Lys Asn
    1130                1135                1140

Ser Lys  Met Ser Lys Ile Arg  Thr His Asn Ser Glu  Val Glu Glu
    1145                1150                1155

Asp Asp  Met Asp Lys His Gln  Gln Lys Ala Arg Phe  Ala Lys Gln
    1160                1165                1170

Pro Ala  Tyr Thr Leu Val Asp  Arg Glu Glu Lys Pro  Pro Asn Gly
    1175                1180                1185

Thr Pro  Thr Lys His Pro Asn  Trp Thr Asn Lys Gln  Asp Asn Arg
    1190                1195                1200

Asp Leu  Glu Ser Ala Gln Ser  Leu Asn Arg Met Glu  Tyr Ile Val
    1205                1210                1215


<210> SEQ ID NO 79
<211> LENGTH: 1218
<212> TYPE: PRT
<213> ORGANISM: Mus sp.

<400> SEQUENCE: 79

Met Arg Ser Pro Arg Thr Arg Gly Arg Pro Gly Arg Pro Leu Ser Leu
```

-continued

```
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Val Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Ile Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Ile
                165                 170                 175

Ala His Phe Glu Tyr Gln Ile Arg Val Thr Cys Asp Asp His Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Asp Cys Asn Lys Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Thr Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Arg Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Ser Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Arg Ser Cys Lys Asn Leu Ile Ala
            420                 425                 430
```

```
Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Thr Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Lys Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala His Cys Glu Asn Asn Ile Asn Asp Cys Ser
            660                 665                 670

Gln Asn Pro Cys His Tyr Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Val Asp Thr Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Asp Ser Phe Thr Cys
        755                 760                 765

Val Cys Lys Glu Gly Trp Glu Gly Pro Ile Cys Thr Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Gln Cys Ile Cys Pro Pro
        835                 840                 845
```

```
Gly His Ser Gly Ala Lys Cys His Glu Val Ser Gly Arg Ser Cys Ile
    850                 855                 860

Thr Met Gly Arg Val Ile Leu Asp Gly Ala Lys Trp Asp Asp Asp Cys
865                 870                 875                 880

Asn Thr Cys Gln Cys Leu Asn Gly Arg Val Ala Cys Ser Lys Val Trp
                885                 890                 895

Cys Gly Pro Arg Pro Cys Arg Leu His Lys Ser His Asn Glu Cys Pro
            900                 905                 910

Ser Gly Gln Ser Cys Ile Pro Val Leu Asp Asp Gln Cys Phe Val Arg
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile  Ala Cys Glu Pro Ser  Leu Ser Ala
        995                 1000                1005

Asn Asn  Glu Ile His Val Ala  Ile Ser Ala Glu Asp  Ile Arg Asp
    1010                1015                1020

Asp Gly  Asn Pro Val Lys Glu  Ile Thr Asp Lys Ile  Ile Asp Leu
    1025                1030                1035

Val Ser  Lys Arg Asp Gly Asn  Ser Ser Leu Ile Ala  Ala Val Ala
    1040                1045                1050

Glu Val  Arg Val Gln Arg Arg  Pro Leu Lys Asn Arg  Thr Asp Phe
    1055                1060                1065

Leu Val  Pro Leu Leu Ser Ser  Val Leu Thr Val Ala  Trp Val Cys
    1070                1075                1080

Cys Leu  Val Thr Ala Phe Tyr  Trp Cys Val Arg Lys  Arg Arg Lys
    1085                1090                1095

Pro Ser  Ser His Thr His Ser  Ala Pro Glu Asp Asn  Thr Thr Asn
    1100                1105                1110

Asn Val  Arg Glu Gln Leu Asn  Gln Ile Lys Asn Pro  Ile Glu Lys
    1115                1120                1125

His Gly  Ala Asn Thr Val Pro  Ile Lys Asp Tyr Glu  Asn Lys Asn
    1130                1135                1140

Ser Lys  Met Ser Lys Ile Arg  Thr His Asn Ser Glu  Val Glu Glu
    1145                1150                1155

Asp Asp  Met Asp Lys His Gln  Gln Lys Val Arg Phe  Ala Lys Gln
    1160                1165                1170

Pro Val  Tyr Thr Leu Val Asp  Arg Glu Glu Lys Ala  Pro Ser Gly
    1175                1180                1185

Thr Pro  Thr Lys His Pro Asn  Trp Thr Asn Lys Gln  Asp Asn Arg
    1190                1195                1200

Asp Leu  Glu Ser Ala Gln Ser  Leu Asn Arg Met Glu  Tyr Ile Val
    1205                1210                1215
```

<210> SEQ ID NO 80
<211> LENGTH: 365
<212> TYPE: PRT
<213> ORGANISM: Mus sp.

<400> SEQUENCE: 80

```
Ala Asp Leu Gly Ser Gln Phe Glu Leu Glu Ile Leu Ser Met Gln Asn
1               5                   10                  15

Val Asn Gly Glu Leu Gln Asn Gly Asn Cys Cys Gly Gly Val Arg Asn
            20                  25                  30

Pro Gly Asp Arg Lys Cys Thr Arg Asp Glu Cys Asp Thr Tyr Phe Lys
        35                  40                  45

Val Cys Leu Lys Glu Tyr Gln Ser Arg Val Thr Ala Gly Gly Pro Cys
    50                  55                  60

Ser Phe Gly Ser Gly Ser Thr Pro Val Ile Gly Gly Asn Thr Phe Asn
65                  70                  75                  80

Leu Lys Ala Ser Arg Gly Asn Asp Arg Asn Arg Ile Val Leu Pro Phe
                85                  90                  95

Ser Phe Ala Trp Pro Arg Ser Tyr Thr Leu Leu Val Glu Ala Trp Asp
            100                 105                 110

Ser Ser Asn Asp Thr Ile Gln Pro Asp Ser Ile Ile Glu Lys Ala Ser
        115                 120                 125

His Ser Gly Met Ile Asn Pro Ser Arg Gln Trp Gln Thr Leu Lys Gln
    130                 135                 140

Asn Thr Gly Ile Ala His Phe Glu Tyr Gln Ile Arg Val Thr Cys Asp
145                 150                 155                 160

Asp His Tyr Tyr Gly Phe Gly Cys Asn Lys Phe Cys Arg Pro Arg Asp
                165                 170                 175

Asp Phe Phe Gly His Tyr Ala Cys Asp Gln Asn Gly Asn Lys Thr Cys
            180                 185                 190

Met Glu Gly Trp Met Gly Pro Asp Cys Asn Lys Ala Ile Cys Arg Gln
        195                 200                 205

Gly Cys Ser Pro Lys His Gly Ser Cys Lys Leu Pro Gly Asp Cys Arg
    210                 215                 220

Cys Gln Tyr Gly Trp Gln Gly Leu Tyr Cys Asp Lys Cys Ile Pro His
225                 230                 235                 240

Pro Gly Cys Val His Gly Thr Cys Asn Glu Pro Trp Gln Cys Leu Cys
                245                 250                 255

Glu Thr Asn Trp Gly Gly Gln Leu Cys Asp Lys Asp Leu Asn Tyr Cys
            260                 265                 270

Gly Thr His Gln Pro Cys Leu Asn Arg Gly Thr Cys Ser Asn Thr Gly
        275                 280                 285

Pro Asp Lys Tyr Gln Cys Ser Cys Pro Glu Gly Tyr Ser Gly Pro Asn
    290                 295                 300

Cys Glu Ile Ala Glu His Ala Cys Leu Ser Asp Pro Cys His Asn Arg
305                 310                 315                 320

Gly Ser Cys Lys Glu Thr Ser Ser Gly Phe Glu Cys Glu Cys Ser Pro
                325                 330                 335

Gly Trp Thr Gly Pro Thr Cys Ser Thr Asn Ile Asp Asp Glu Phe Gly
            340                 345                 350

Leu Val Pro Arg Gly Ser Gly His His His His His His
        355                 360                 365
```

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Gly Phe Thr Phe Ser Asn Tyr Gly Ile His
1 5 10

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Trp Ile Thr Pro Asp Gly Gly Tyr Thr Asp Tyr Ala Asp Ser Val Lys
1 5 10 15

Gly

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Trp Ile Thr Gly Asn Gly Gly Tyr Ser Asp Tyr Ala Asp Ser Val Lys
1 5 10 15

Gly

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Pro or Gly
<220> FEATURE:
<221> NAME/KEY: MOD_RES
<222> LOCATION: (5)..(5)
<223> OTHER INFORMATION: Asp or Asn
<220> FEATURE:
<221> NAME/KEY: MOD_RES
<222> LOCATION: (9)..(9)
<223> OTHER INFORMATION: Thr or Ser

<400> SEQUENCE: 84

Trp Ile Thr Xaa Xaa Gly Gly Tyr Xaa Asp Tyr Ala Asp Ser Val Lys
1 5 10 15

Gly

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Ala Gly Ser Trp Phe Ala Tyr
1 5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Ala Gly Ser Leu Phe Ala Tyr
1 5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(4)
<223> OTHER INFORMATION: Trp or Leu

<400> SEQUENCE: 87

Ala Gly Ser Xaa Phe Ala Tyr
1 5

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Arg Ala Ser Gln Asp Val Ser Thr Ala Val Ala
1 5 10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Ser Ala Ser Phe Leu Tyr Ser
1 5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Gln Gln Ser Tyr Thr Thr Pro Pro Thr
1 5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Gln Gln Tyr Tyr Thr Thr Ala Thr Thr
1 5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Pro or Thr

<400> SEQUENCE: 92

Gln Gln Xaa Tyr Thr Thr Xaa Xaa Thr
1 5

<210> SEQ ID NO 93
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Gly Ile His Trp Val Arg Gln Ala Pro Gly Lys Gly Leu Glu Trp Val
35 40 45

Gly Trp Ile Thr Pro Asp Gly Gly Tyr Thr Asp Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Ala Gly Ser Trp Phe Ala Tyr Trp Gly Gln Gly Thr Leu Val
100 105 110

Thr Val Ser Ser
115

<210> SEQ ID NO 94
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Pro Asp Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Ser Leu Phe Ala Tyr Trp Gly Gln Gly Thr Leu Val
            100                 105                 110

Thr Val Ser Ser
        115

<210> SEQ ID NO 95
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Gly Asn Gly Gly Tyr Ser Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Ser Trp Phe Ala Tyr Trp Gly Gln Gly Thr Leu Val
            100                 105                 110

Thr Val Ser Ser
        115

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile

```
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105


<210> SEQ ID NO 97
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Ala Thr
                85                  90                  95

Thr Phe Gly Gln Gly Thr Lys Val Glu Ile Lys
            100                 105


<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105
```

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

```
Trp Val Arg Gln Ala Pro Gly Lys Gly Leu Glu Trp Val Gly
1               5                   10
```

<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Lys Arg Phe
            20                  25                  30

Leu Ala Trp Tyr Gln Gln Lys Pro Gly Lys Ala Pro Lys Leu Leu Ile
        35                  40                  45

Tyr Gly Ala Ser Thr Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Arg Ser Pro His
                85                  90                  95

Thr Phe Gly Gln Gly Thr Lys Val Glu Ile Lys
            100                 105
```

<210> SEQ ID NO 101
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Thr Thr Pro Ser
                85                  90                  95

Thr Phe Gly Gln Gly Thr Lys Val Glu Ile Lys
            100                 105
```

<210> SEQ ID NO 102

<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 102

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Tyr
20 25 30

Val Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Trp Asn Ser Tyr Pro Phe
85 90 95

Thr Phe Gly Gln Gly Thr Lys Val Glu Ile Lys
100 105

<210> SEQ ID NO 103
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 103

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Thr Thr Pro Pro
85 90 95

Thr Phe Gly Gln Gly Thr Lys Val Glu Ile Lys
100 105

<210> SEQ ID NO 104
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 104

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Phe Thr Ser Tyr
20 25 30

Gly Met Ser Trp Val Arg Gln Ala Pro Gly Lys Gly Leu Glu Trp Val
35 40 45

Ser Tyr Ile Tyr Pro Tyr Ser Gly Ala Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg His Ser Gly Tyr Tyr Arg Ile Ser Ser Ala Met Asp Val Trp
100 105 110

Gly Gln Gly Thr Leu Val Thr Val Ser Ser
115 120

<210> SEQ ID NO 105
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Ile His Trp Val Arg Gln Ala Pro Gly Lys Gly Leu Glu Trp Val
35 40 45

Ala Arg Ile Asn Pro Pro Asn Arg Ser Asn Gln Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Gly Ser Gly Phe Arg Trp Val Met Asp Tyr Trp Gly Gln Gly
100 105 110

Thr Leu Val Thr Val Ser Ser
115

<210> SEQ ID NO 106
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Trp Met Ser Trp Val Arg Gln Ala Pro Gly Lys Gly Leu Glu Trp Val
35 40 45

Gly Ala Ile Ser Ser Ser Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

-continued

```
Leu Gln Met Asn Ser Leu Arg Ala Glu Asp Thr Ala Val Tyr Tyr Cys
                85                  90                  95

Ala Arg Gln Tyr Tyr Arg Asp Met Asp Val Trp Gly Gln Gly Thr Leu
            100                 105                 110

Val Thr Val Ser Ser
        115


<210> SEQ ID NO 107
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Gly Asn Gly Gly Tyr Ser Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Ser Trp Phe Ala Tyr Trp Gly Gln Gly Thr Leu Val
            100                 105                 110

Thr Val Ser Ser
        115
```

UNITED STATES PATENT AND TRADEMARK OFFICE
CERTIFICATE OF CORRECTION

PATENT NO.          : 9,550,829 B2                                    Page 1 of 1
APPLICATION NO.     : 14/208523
DATED               : January 24, 2017
INVENTOR(S)         : French et al.

It is certified that error appears in the above-identified patent and that said Letters Patent is hereby corrected as shown below:

In the Specification

In Column 20, Line 57, "customarily included in Field Code Changed commercial" should read --customarily included in commercial--

In Column 20, Line 63, "to a reference polypeptide Field Code Changed sequence is" should read --to a reference polypeptide sequence is--

Signed and Sealed this
Fourth Day of April, 2017

Michelle K. Lee
*Director of the United States Patent and Trademark Office*